(12) United States Patent  (10) Patent No.: US 8,071,082 B2
Zugates et al. (45) Date of Patent: Dec. 6, 2011

(54) END-MODIFIED POLY(BETA-AMINO ESTERS) AND USES THEREOF

(75) Inventors: Gregory T. Zugates, Cambridge, MA (US); Andreas Zumbuehl, Bern (CH); Robert S. Langer, Newton, MA (US); Daniel G. Anderson, Sudbury, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1046 days.

(21) Appl. No.: 11/780,754

(22) Filed: Jul. 20, 2007

(65) Prior Publication Data

US 2008/0242626 A1 Oct. 2, 2008

Related U.S. Application Data

(60) Provisional application No. 60/832,517, filed on Jul. 21, 2006.

(51) Int. Cl.
*A61K 31/765* (2006.01)
*A61K 9/00* (2006.01)
*A61K 48/00* (2006.01)
*C12N 15/11* (2006.01)
*C08F 26/00* (2006.01)

(52) U.S. Cl. ........ 424/78.37; 424/400; 514/44; 526/312
(58) Field of Classification Search ............... 424/78.37, 424/401, 400; 514/44; 526/312
See application file for complete search history.

(56) References Cited

U.S. PATENT DOCUMENTS

| 2,759,913 | A | 8/1956 | Hulse |
| 3,963,771 | A | 6/1976 | Robson et al. |
| 4,224,365 | A | 9/1980 | Ali-Zaidi |
| 4,348,511 | A | 9/1982 | Haug |
| 5,180,424 | A | 1/1993 | Hutter |
| 5,364,634 | A | 11/1994 | Lew |
| 5,462,990 | A | 10/1995 | Hubbell et al. |
| 5,705,188 | A | 1/1998 | Junichi et al. |
| 5,770,637 | A | 6/1998 | Vanderlaan et al. |
| 5,858,746 | A | 1/1999 | Hubbell et al. |
| 5,904,927 | A | 5/1999 | Amiji |

(Continued)

FOREIGN PATENT DOCUMENTS

DE 19626567 A1 1/1998

(Continued)

OTHER PUBLICATIONS

Anderson et al. ("Structure/Property Studies of Polymeric Gene Delivery Using a Library of Poly(_-amino esters", in Molecular Therapy, vol. 11, No. 3, Mar. 2005).*

(Continued)

*Primary Examiner* — Blessing Fubara
(74) *Attorney, Agent, or Firm* — Wolf, Greenfield & Sacks, P.C.; C. Hunter Baker; Robin A. Weatherhead

(57) ABSTRACT

Poly(beta-amino esters) are end-modified to form materials useful in the medical as well as non-medical field. An amine-terminated poly(beta-amino ester) is reacted with an electrophile, or an acrylate-terminated poly(beta-amino ester) is reacted with a nucleophile. The inventive end-modified polymers may be used in any field where polymers have been found useful including the drug delivery arts. The end-modified polymers are particularly useful in delivery nucleic acids such as DNA or RNA. The invention also provides compositions including the inventive end-modified polymers, methods of preparing the inventive polymers, and method of using the inventive polymers.

68 Claims, 10 Drawing Sheets

U.S. PATENT DOCUMENTS

| | | | |
|---|---|---|---|
| 5,962,520 A | 10/1999 | Smith et al. | |
| 6,060,582 A | 5/2000 | Hubbell et al. | |
| 6,998,115 B2 * | 2/2006 | Langer et al. | 424/78.37 |
| 7,427,394 B2 * | 9/2008 | Anderson et al. | 424/78.37 |
| 2002/0131951 A1 | 9/2002 | Langer et al. | |
| 2004/0071654 A1 | 4/2004 | Anderson et al. | |
| 2005/0238716 A1 | 10/2005 | Verrijk et al. | |
| 2005/0265961 A1 | 12/2005 | Langer et al. | |
| 2008/0145338 A1 | 6/2008 | Anderson et al. | |
| 2010/0036084 A1 | 2/2010 | Langer et al. | |

FOREIGN PATENT DOCUMENTS

| | | |
|---|---|---|
| EP | 0959092 A1 | 11/1999 |
| JP | 52-045327 | 4/1977 |
| JP | 08092369 A | 4/1996 |
| JP | 2004-506000 | 2/2004 |
| WO | WO 98/16202 A2 | 4/1998 |
| WO | WO 02/13767 A2 | 2/2002 |
| WO | WO 02/31025 A2 | 4/2002 |
| WO | WO 2004/106411 A2 * | 12/2004 |

OTHER PUBLICATIONS

U.S. Appl. No. 60/239,330, filed Oct. 10, 2000, Langer et al.
U.S. Appl. No. 60/305,337, filed Jul. 13, 2001, Langer et al.
International Search Report and Written Opinion for PCT/US2004/016521 mailed Dec. 8, 2004.
International Preliminary Report on Patentability for PCT/US2004/016521 mailed Dec. 15, 2005.
International Search Report for PCT/US2001/031270 mailed May 22, 2002.
Written Opinion for PCT/US2001/031270 mailed Jan. 2, 2003.
International Preliminary Examination Report for PCT/US2001/031270 mailed Aug. 19, 2003.
International Search Report and Written Opinion for PCT/US2007/073976 mailed Sep. 29, 2008.
International Preliminary Report on Patentability for PCT/US2007/073976 mailed Feb. 5, 2009.
International Search Report and Written Opinion for PCT/US2007/070430 mailed Dec. 13, 2007.
International Preliminary Report on Patentability for PCT/US2007/070430 mailed Dec. 24, 2008.
Office Communication mailed Jan. 26, 2007 for U.S. Appl. No. 10/446,444.
Office Communication mailed Oct. 3, 2007 for U.S. Appl. No. 10/446,444.
Notice of Allowance mailed May 21, 2008 for U.S. Appl. No. 10/446,444.
Office Communication mailed May 20, 2003 for U.S. Appl. No. 09/969,431.
Office Communication mailed Oct. 2, 2003 for U.S. Appl. No. 09/969,431.
Office Communication mailed May 13, 2004 for U.S. Appl. No. 09/969,431.
Notice of Allowance mailed Nov. 18, 2004 for U.S. Appl. No. 09/969,431.
Office Communication mailed Jul. 9, 2009 for U.S. Appl. No. 11/099,886.
Akinc et al., Measuring the pH environment of DNA delivered using nonviral vectors: implications for lysosomal trafficking. Biotechnol Bioeng. Jun. 5, 2002;78(5):503-8.
Akinc et al., Parallel synthesis and biophysical characterization of a degradable polymer library for gene delivery. J Am Chem Soc. May 7, 2003;125(18):5316-23.
Allison, The mode of action of immunological adjuvants. Dev Biol Stand. 1998;92:3-11.
Anderson, Human gene therapy. Nature. Apr. 30, 1998;392(6679 Suppl):25-30.
Anderson et al., A polymer library approach to suicide gene therapy for cancer. Proc Natl Acad Sci USA. Nov. 9, 2004;101(45):16028-33. Epub Nov. 1, 2004.
Anderson et al., Biodegradation and biocompatibility of PLA and PLGA microspheres. Adv Drug Deliv Rev. Oct. 13, 1997;28(1):5-24.

Anderson et al., Nanoliter-scale synthesis of arrayed biomaterials and application to human embryonic stem cells. Nat Biotechnol. Jul. 2004;22(7):863-6. Epub Jun. 13, 2004.
Anderson et al., Semi-automated synthesis and screening of a large library of degradable cationic polymers for gene delivery. Angew Chem Int Ed Engl. Jul. 14, 2003;42(27):3153-8.
Anderson et al., Structure/property studies of polymeric gene delivery using a library of poly(beta-amino esters). Mol Ther. Mar. 2005;11(3):426-34.
Ando et al., PLGA microspheres containing plasmid DNA: preservation of supercoiled DNA via cryopreparation and carbohydrate stabilization. J Pharm Sci. Jan. 1999;88(1):126-30.
Angeloni et al., Liquid crystalline poly (β-aminoester)s containing different mesogenic groups. Makromlekulare Chemie. 1985;186:977-97.
Anseth et al., In situ forming degradable networks and their application in tissue engineering and drug delivery. J Control Release. Jan. 17, 2002;78(1-3):199-209.
Anseth et al., New Directions in Photopolymerizable Biomaterials. Mrs Bull. 2002;27:130-136.
Anseth et al., Photopolymerizable degradable polyanhydrides with osteocompatibility. Nat Biotechnol. Feb. 1999;17(2):156-9.
Anseth et al., Polymeric Dental Composites: Properties and Reaction Behavior of Multimethacrylate Dental Restorations. Advances in Polymer Science. 1995;122:177-217.
Barbucci et al. Macroinorganics. 7. Property-Structure Relationships for Polymeric Bases Whose Monomeric Units Behave Independently towards Protonation. Macromolecules 1981;14:1203-09.
Barbucci et al., Protonation studies of multifunctional polymers with a poly(amido-amine) structure. Polymer. 1978;19:1329-34.
Barbucci et al., Thermodynamic ad $^{13}C$ n.m.r. data on the protonation of polymeric bases whose repeating units behave independently towards protonation. Polymer. 1980;21:81-85.
Barrera et al., Synthesis and RGD Peptide Modification of a New Biodegradable Copolymer: Poly(lactic acid-*co*-lysine). J Am Chem Soc. 1993;115:11010-11.
Beebe et al., Microfluidic tectonics: a comprehensive construction platform for microfluidic systems. Proc Natl Acad Sci U S A. Dec. 5, 2000;97(25):13488-93.
Behr, Synthetic Gene-Transfer Vectors. Acc Chem Res. 1993;26:274-78.
Behr, The Proton Sponge: a Trick to Enter Cells the Viruses Did Not Exploit. Chimia. 1997;51:34-36.
Benns et al., pH-sensitive cationic polymer gene delivery vehicle: N-Ac-poly(L-histidine)-graft-poly(L-lysine) comb shaped polymer. Bioconjug Chem. Sep.-Oct. 2000;11(5):637-45.
Boussif et al., A versatile vector for gene and oligonucleotide transfer into cells in culture and in vivo: polyethylenimine. Proc Natl Acad Sci U S A. Aug. 1, 1995;92(16):7297-301.
Brazeau et al., In vitro myotoxicity of selected cationic macromolecules used in non-viral gene delivery. Pharm Res. May 1998;15(5):680-4.
Brocchini et al., A Combinatorial Approach for Polymer Designs. J Am Chem Soc. 1997;119:4553-54.
Brocchini, Combinatorial chemistry and biomedical polymer development. Adv Drug Deliv Rev. Dec. 3, 2001;53(1):123-30.
Bryant et al., Cytocompatibility of UV and visible light photoinitiating systems on cultured NIH/3T3 fibroblasts in vitro. J Biomater Sci Polym Ed. 2000;11(5):439-57.
Burdick et al., Photoencapsulation of osteoblasts in injectable RGD-modified PEG hydrogels for bone tissue engineering. Biomaterials. Nov. 2002;23(22):4315-23.
Burdick et al., Stimulation of neurite outgrowth by neurotrophins delivered from degradable hydrogels. Biomaterials. Jan. 2006;27(3):452-9. Epub Aug. 22, 2005.
Byloos et al., Phase Transitions of Alkanethiol Self-Assembled Monolayers at an Electrified Gold Surface. J Phys Chem B. 2001;105:5900-05.
Caminschi et al., Molecular cloning of F4/80-like-receptor, a seven-span membrane protein expressed differentially by dendritic cell and monocyte-macrophage subpopulations. J Immunol. Oct. 1, 2001;167(7):3570-6.

Capan et al., Preparation and characterization of poly (D,L-lactide-co-glycolide) microspheres for controlled release of poly(L-lysine) complexed plasmid DNA. Pharm Res. Apr. 1999;16(4):509-13.

Casimiro et al., Vaccine-induced immunity in baboons by using DNA and replication-incompetent adenovirus type 5 vectors expressing a human immunodeficiency virus type 1 gag gene. J Virol. Jul. 2003;77(13):7663-8.

Chan et al., Triplex DNA: fundamentals, advances, and potential applications for gene therapy. J Mol Med. Apr. 1997;75(4):267-82.

Cho et al., A proposed mechanism for the induction of cytotoxic T lymphocyte production by heat shock fusion proteins. Immunity. Mar. 2000;12(3):263-72.

Cho et al., Homeostasis-stimulated proliferation drives cotton T cells to differentiate directly into memory T cells. J Exp Med. Aug. 21, 2000;192(4):549-56.

Choksakulnimitr et al., In vitro cytotoxicity of macromolecules in different cell culture systems. J Control Rel. 1995;34:233-41.

Cotten et al., Receptor-mediated transport of DNA into eukaryotic cells. Methods Enzymol.1993;217:618-44.

Crooke, Evaluating the mechanism of action of antiproliferative antisense drugs. Antisense Nucleic Acid Drug Dev. Apr. 2000;10(2):123-6; discussion 127.

Crooke, Molecular mechanisms of action of antisense drugs. Biochim Biophys Acta. Dec. 10, 1999;1489(1):31-44.

Crystal, Transfer of genes to humans: early lessons and obstacles to success. Science. Oct. 20, 1995;270(5235):404-10.

Danusso et al., Nuovi alti polimeri da poliaddizione di piperazina o 2-metilpiperazina a diesteri acrilici o divinilsolfone. Chim Ind (Milan). 1967;49:826-30. Italian.

Danusso et al., Synthesis of tertiary amine polymers. Polymer. 1970;11:88-113.

De Smedt et al., Cationic polymer based gene delivery systems. Pharm Res. Feb. 2000;17(2):113-26.

Demeneix et al., Chapter 14. The Proton Sponge: A Trick the Viruses Did Not Exploit. Artificial Self Assembly Systems for Gene Delivery (Felgner et al Eds). 1996:146-51.

Deshmukh et al., Liposome and polylysine mediated gene transfer. New J Chem. 1997;21:113-24.

Eddington et al., Flow control with hydrogels. Adv Drug Deliv Rev. Feb. 10, 2004;56(2):199-210.

Elisseeff et al., Transdermal photopolymerization for minimally invasive implantation. Proc Natl Acad Sci U S A. Mar. 16, 1999;96(6):3104-7.

Ferruti et al., A novel modification of poly(L-lysine) leading to a soluble cationic polymer with reduced toxicity and with potential as a transfection agent. Macromol Chem Phys 1998;199:2565-75.

Ferruti et al., Linear Amino Polymers: Synthesis, Protonation and Complex Formation. Advances in Polymer Sci. 1984;58:55-92.

Ferruti et al., Recent results on functional polymers and macromonomers of interest as biomaterials or for biomaterial modification. Biomaterials. Dec. 1994;15(15):1235-41.

Ferruti et al., Synthesis, characterisation and antitumour activity of platinum (II) complexes of novel functionalised poly(amido amine)s. Macromol Chem Phys. 1999;200:1644-54.

Ferruti et al., Synthesis, physico-chemical properties and biomedical applications of poly(amido-amine)s. Polymyer. 1985;26:1336-48.

Field et al., A simple predictive model for spherical indentation. J Mater Res. 1993;8(2):297-306.

Fire et al., Potent and specific genetic interference by double-stranded RNA in Caenorhabditis elegans. Nature. Feb. 19, 1998;391(6669):806-11.

Fisher et al., Photoinitiated Polymerization of Biomaterials. Annu Rev Mater Res. 2001;31:171-181.

Fisher et al., Synthesis and properties of photocross-linked poly(propylene fumarate) scaffolds. J Biomater Sci Polym Ed. 2001;12(6):673-87.

Fominaya et al., Target cell-specific DNA transfer mediated by a chimeric multidomain protein. Novel non-viral gene delivery system. J Biol Chem. May 3, 1996;271(18):10560-8.

Friedmann, Human gene therapy—an immature genie, but certainly out of the bottle. Nat Med. Feb. 1996;2(2):144-7.

Fritz et al., Gene transfer into mammalian cells using histone-condensed plasmid DNA. Hum Gene Ther. Aug. 1, 1996;7(12):1395-404.

Fu et al., Visual Evidence of Acidic Environment Within Degrading Poly(lactic-co-glycolic acid) (PLGA) Microspheres. Pharma Res. 2000;17(1):100-06.

Garg et al., Genetic tagging shows increased frequency and longevity of antigen-presenting, skin-derived dendritic cells in vivo. Nat Immunol. Sep. 2003;4(9):907-12. Epub Aug. 10, 2003.

Gebhart et al., Evaluation of polyplexes as gene transfer agents. J Control Release. Jun. 15, 2001;73(2-3):401-16.

Gerasimov et al., Cytosolic drug delivery using pH- and light-sensitive liposomes. Adv Drug Deliv Rev. Aug. 20, 1999;38(3):317-338.

Gonzalez et al., New class of polymers for the delivery of macromolecular therapeutics. Bioconjug Chem. Nov.-Dec. 1999;10(6):1068-74.

Haensler et al., Polyamidoamine cascade polymers mediate efficient transfection of cells in culture. Bioconjug Chem. Sep.-Oct. 1993;4(5):372-9.

Hanes et al., New advances in microsphere-based single-dose vaccines. Adv Drug Deliv Rev. Oct. 13, 1997;28(1):97-119.

Hansen et al., Re-examination and further development of a precise and rapid dye method for measuring cell growth/cell kill. J Immunol Methods. May 12, 1989;119(2):203-10.

He et al., Experimental Investigation into One-Step and Two-Steps Polymerization Via Michael Addition from Primary Amine. Polymer Preprints. 2001;42(2):335-36.

Hill et al., In vitro cytotoxicity of poly(amidoamine)s: relevance to DNA delivery. Biochim Biophys Acta. Apr. 19, 1999;1427(2):161-74.

Hope et al., Cationic lipids, phosphatidylethanolamine and the intracellular delivery of polymeric, nucleic acid-based drugs (review). Mol Membr Biol. Jan.-Mar. 1998;15(1):1-14.

Huang et al., Long-term in vivo gene expression via delivery of PEI-DNA condensates from porous polymer scaffolds. Hum Gene Ther. May 2005;16(5):609-17.

Hutchison et al., Robust polymer microfluidic device fabrication via contact liquid photolithographic polymerization (CLiPP). Lab Chip. 2004;4:658-662.

Hwang et al., Effects of structure of beta-cyclodextrin-containing polymers on gene delivery. Bioconjug Chem. Mar.-Apr. 2001;12(2):280-90.

Kabanov et al., DNA complexes with polycations for the delivery of genetic material into cells. Bioconjug Chem. Jan.-Feb. 1995;6(1):7-20.

Kabanov, Taking polycation gene delivery systems from in vitro to in vivo. Pharm Sci Technolo Today. Sep. 1999;2(9):365-372.

Kargina et al., Self-Splitted Water-Soluble Ionogenic Polymers. Vysokomol Soedin Seriya. 1986;28:1139-44. (Abstract Only).

Kawata et al., Finer features for functional microdevices. Nature. Aug. 16, 2001;412(6848):697-8.

Khademhosseini et al., Molded polyethylene glycol microstructures for capturing cells within microfluidic channels. Lab Chip. Oct. 2004;4(5):425-30. Epub Jul. 26, 2004.

Korshak et al., Water-soluble anion exchange resins based on methacrylic beta-aminoesters. Vysokomolekulyarnye Soedineniya, Seriya B: Kratkie Soobscheniya. 1975;17(5):401-04.

Kukowska-Latallo et al., Efficient transfer of genetic material into mammalian cells using Starburst polyamidoamine dendrimers. Proc Natl Acad Sci U S A. May 14, 1996;93(10):4897-902.

Kwon et al., Pseudopoly(amino acids): A Study of the Synthesis and Characterization of Poly(*trans*-4-hydroxy-*N*-acyl-L-proline esters). Macromolecules. 1989;22:3250-55.

Leach et al., Bone engineering by controlled delivery of osteoinductive molecules and cells. Expert Opin Biol Ther. Jul. 2004;4(7):1015-27.

Leach et al., Photocrosslinked hyaluronic acid hydrogels: natural, biodegradable tissue engineering scaffolds. Biotechnology and Bioengineering. 2003;82:578-589.

Ledley, Nonviral gene therapy: the promise of genes as pharmaceutical products. Hum Gene Ther. Sep. 1995;6(9):1129-44.

Lim et al., A Self-Destroying Polycationic Polymer: Biodegradable Poly(4-hydroxy-L-proline ester). J Am Chem Soc. 1999;121:5633-39.

Lim et al., Biodegradable, endosome disruptive, and cationic network-type polymer as a highly efficient and nontoxic gene delivery carrier. Bioconjug Chem. Sep.-Oct. 2002;13(5):952-7.

Lim et al., Cationic hyperbranched poly(amino ester): a novel class of DNA condensing molecule with cationic surface, biodegradable three-dimensional structure, and tertiary amine groups in the interior. J Am Chem Soc. Mar. 14, 2001;123(10):2460-1.

Lim et al., Development of a Safe Gene Delivery System Using Biodegradable Polymer, Poly[α-(4-aminobutyl)-L-glycolic acid].J Am Chem Soc. 2000;122:6524-25.

Lim et al., Self-assembled ternary complex of cationic dendrimer, cucurbituril, and DNA: noncovalent strategy in developing a gene delivery carrier. Bioconjug Chem. Nov.-Dec. 2002;13(6):1181-5.

Linhardt et al., Free-Radical Synthesis of Poly(2-ethylacrylic acid) Fractions of Low Polydispersity: Effects of Molecular Weight and Polydispersity on the pH-Dependent Conformational Transition in Aqueous Solutions. Macromolecules. 1999;32:4457-59.

Linhardt et al., pH-Induced Fusion and Lysis of Phosphatidylcholine Vesicles by the Hydrophobic Polyelectrolyte Poly(2-ethylacrylic Acid). Langmuir. 2000;16:122-27.

Liu et al., Three-dimensional photopatterning of hydrogels containing living cells. Biomedical Microdevices. 2002;4:257-266.

Loan et al., Oligoamidoamines and oligoesteramines based on antibiotics containing β-lactam ring. Euro Poly J. 1996;32:957-62.

Loan et al., Poly(amdio amine)s and poly(ester amine)s based on aromatic amines containg carboxyl groups. Macromolecular Chem and Phys. 1995;11:3525-33.

Luman et al., The convergent synthesis of poly(glycerol-succinic acid) dendritic macromolecules. Chemistry. Nov. 21, 2003;9(22):5618-26.

Luo et al., Synthetic DNA delivery systems. Nat Biotechnol. Jan. 2000;18(1):33-7.

Lynn et al., Accelerated discovery of synthetic transfection vectors: parallel synthesis and screening of a degradable polymer library. J Am Chem Soc. Aug. 22, 2001;123(33):8155-6.

Lynn et al., Degradable poly (β-amino eaters): synthesis, characterization, and self-assembly with plasmid DNA. J Am Chem Soc. 2000;122:10761-68.

Lynn et al., pH-Responsive Polymer Microspheres: Rapid Release of Encapsulated Material within the Range of Intracellular pH. Angew Chem Int Ed Engl. May 4, 2001;40(9):1707-1710.

Mann et al., Smooth muscle cell growth in photopolymerized hydrogels with cell adhesive and proteolytically degradable domains: synthetic ECM analogs for tissue engineering. Biomaterials. Nov. 2001;22(22):3045-51.

Maruo et al., Three-dimensional microfabrication with two-photon-absorbed photopolymerization. Opt Lett. Jan. 15, 1997;22(2):132-4.

Mathiowitz et al., Novel Mircocapsules for Delivery Sytems. Reactive Polymers. 1987;6:27-283.

Mathiowitz et al., Polyanhydride Microspheres as Drug Carriers. I. Hot-Melt Microencapsulation. J Control Rel. 1987;5:13-22.

Mathiowitz et al., Polyanhydride Microspheres as Drug Carriers. II. Microencapsulation by Solvent Removal. J Appl Polymer Sci. 1988;35:755-74.

Midoux et al., Efficient gene transfer by histidylated polylysine/pDNA complexes. Bioconjug Chem. May-Jun. 1999;10(3):406-11.

Miller, Cationic Liposomes for Gene Therapy. Angew Chem Int Ed. 1998;37:1769-85.

Mulligan, The basic science of gene therapy. Science. May 14, 1993;260(5110):926-32.

Murphy et al., A combinatorial approach to the discovery of efficient cationic peptoid reagents for gene delivery. Proc Natl Acad Sci U S A. Feb. 17, 1998;95(4):1517-22.

Nguyen et al., Photopolymerizable hydrogels for tissue engineering applications. Biomaterials. Nov. 2002;23(22):4307-14.

O'Donnell et al., Preparation of microspheres by the solvent evaporation technique. Adv Drug Delivery Rev. 1997;28:25-42.

O'Hagan et al., Induction of potent immune responses by cationic microparticles with adsorbed human immunodeficiency virus DNA vaccines. J Virol. Oct. 2001;75(19):9037-43.

Okada, One- and three-month release injectable microspheres of the LH-RH superagonist leuprorelin acetate. Adv Drug Deliv Rev. Oct. 13, 1997;28(1):43-70.

Pack et al., Design of imidazole-containing endosomolytic biopolymers for gene delivery. Biotechnol Bioeng. Jan. 20, 2000;67(2):217-23.

Phillips et al., Enhanced antibody response to liposome-associated protein antigens: preferential stimulation of IgG2a/b production. Vaccine. 1992;10(3):151-8.

Prabha et al., Size-dependency of nanoparticle-mediated gene transfection: studies with fractionated nanoparticles. Int J Pharm. Sep. 5, 2002;244(1-2):105-15.

Putnam et al., Poly(4-hydroxy-L-proline ester): Low-Temperature Polycondensation and Plasmid DNA Complexation. Macromolecules 1999;32:3658-62.

Putnam et al., Polymer-based gene delivery with low cytotoxicity by a unique balance of side-chain termini. Proc Natl Acad Sci U S A. Jan. 30, 2001;98(3):1200-5. Epub Jan. 23, 2001.

Rao et al., Poly(butanediol Spermate): A Hydrolytically Labile Polyester-Based Nitric Oxide Carrier. J Bioactive Compatible Polymers. 1999;14:54-63.

Remy et al., Gene transfer with lipospermines and polyethylenimines. Adv Drug Deliv Rev. Mar. 2, 1998;30(1-3):85-95.

Roberts et al., Preliminary biological evaluation of polyamidoamine (PAMAM) Starburst dendrimers. J Biomed Mater Res. Jan. 1996;30(1):53-65.

Sahoo et al., Residual polyvinyl alcohol associated with poly (D,L-lactide-co-glycolide) nanoparticles affects their physical properties and cellular uptake. J Control Release. Jul. 18, 2002;82(1):105-14.

Sanford, The biolistic process. Trends Biotechnol. 1988;6:299-302.

Schaffer et al., Vector unpacking as a potential barrier for receptor-mediated polyplex gene delivery. Biotechnol Bioeng. Mar. 5, 2000;67(5):598-606.

Schweikl et al., Triethylene glycol dimethacrylate induces large deletions in the hprt gene of V79 cells. Mutat Res. Jan. 2, 1999;438(1):71-8.

Shchori, Poly(secondary Amine)s from Diacrylates and Diamines. J Polym Sci Polymer. 1983;21:413-15.

Singh et al., Cationic microparticles: A potent delivery system for DNA vaccines. Proc Natl Acad Sci U S A. Jan. 18, 2000;97(2):811-6.

Smeds et al., Photocrosslinkable polysaccharides for in situ hydrogel formation. J Biomed Mater Res. Jan. 2001;54(1):115-21.

Somia et al., Gene therapy: trials and tribulations. Nat Rev Genet. Nov. 2000;1(2):91-9.

Strong et al., A General. Synthetic Route to Defined, Biologically Active Multivalent Arrays. J Am Chem Soc. 1999;121:6193-96.

Tang et al., In vitro gene delivery by degraded polyamidoamine dendrimers. Bioconjug Chem. Nov.-Dec. 1996;7(6):703-14.

Trubetskoy et al., Recharging cationic DNA complexes with highly charged polyanions for in vitro and in vivo gene delivery. Gene Ther. Feb. 2003;10(3):261-71.

Tweedie et al., Combinatorial material mechanics: high-throughput polymer synthesis and nanomechanical screening. Adv Mater. 2005;17:2599-2604.

Uhrich, Hyperbranched Polymers for Drug Discovery. Trends Polymer Sci. 1997;5:388-93.

Unal et al., Influence of filler addition on the mechanical properties of nylon-6 polymer. Journal of Reinforced Plastics and Composites. 2004;23(5):461-469.

Unkeless et al., Structure and function of human and murine receptors for IgG. Annu Rev Immunol. 1988;6:251-81.

Van De Wetering et al., Structure-activity relationships of water-soluble cationic methacrylate/methacrylamide polymers for nonviral gene delivery. Bioconjug Chem. Jul.-Aug. 1999;10(4):589-97.

Vázquez et al., Construction of hydrolytically-degradable thin films via layer-by-layer deposition of degradable polyelectrolytes. J Am Chem Soc. Nov. 27, 2002;124(47):13992-3.

Wagner et al., Influenza virus hemagglutinin HA-2 N-terminal fusogenic peptides augment gene transfer by transferrin-polylysine-DNA complexes: toward a synthetic virus-like gene-transfer vehicle. Proc Natl Acad Sci U S A. Sep. 1, 1992;89(17):7934-8.

Walter et al., Microencapsulation of DNA using poly(DL-lactide-co-glycolide): stability issues and release characteristics. J Control Release. Sep. 20, 1999;61(3):361-74.

Wang et al., Mechanical and rheological properties of HDPE/graphite composite with enhanced thermal conductivity. Polymer Composites. 2001;22(1):97-103.

West et al., Photopolymerized hydrogel materials for drug delivery applications. Reactive Polymers. 1995; 25:139-147.

Yang et al., A new approach to identifying genotoxic carcinogens: p53 induction as an indicator of genotoxic damage. Carcinogenesis. Jun. 1998;19(6):1117-25.

Zauner et al., Polylysine-based transfection systems utilizing receptor-mediated delivery. Adv Drug Deliv Rev. Mar. 2, 1998;30(1-3):97-113.

Zhou et al., Preparation of Poly(L-serine ester): A Structural Analogue of Conventional Poly(L-serine). Macromolecules. 1990;23:3399-406.

Extended European Search Report, mailed Oct. 5, 2009, for EP 07813156.2.

Office Action, mailed Apr. 6, 2010, for U.S. Appl. No. 12/568,481.
Office Action, mailed Jan. 22, 2010, for U.S. Appl. No. 11/099,886.
Office Action, mailed Dec. 4, 2009, for U.S. Appl. No. 11/758,078.
Office Action, mailed Jun. 24, 2010, for U.S. Appl. No. 11/758,078.

Flory et al., Principles of Polymer Chemistry. Cornell University Press. Ithaca, New York. 1953:40-46, 318-23.

Haugland, Handbook of Fluorescent Probes and Research Chemicals. 6$^{th}$ ed. Molecular Probes, Inc. 1996:29.

Hedley et al., Microspheres containing plasmid-encoded antigens elicit cytotoxic T-cell responses. Nat Med. Mar. 1998;4(3):365-8.

Odian et al., Step Polymerization. In: Principles of Polymerization. John Wiley & Sons, Inc. New York. 1991:73-89.

Schwartz et al., Peptide-mediated cellular delivery. Curr Opin Mol Ther. Apr. 2000;2(2):162-7.

Wiethoff et al., Barriers to nonviral gene delivery. J Pharm Sci. Feb. 2003;92(2):203-17.

\* cited by examiner

END-MODIFIED POLY(BETA-AMINO ESTERS) AND USES THEREOF

RELATED APPLICATIONS

The present application claims priority under 35 U.S.C. §119(e) to U.S. provisional patent application, U.S. Ser. No. 60/832,517, filed Jul. 21, 2006, which is incorporated herein by reference.

The present application is also related but does not claim priority to U.S. patent applications, U.S. Ser. No. 11/099,886, filed Apr. 6, 2005; U.S. Ser. No. 10/446,444, filed May 28, 2003; U.S. Ser. No. 09/969,431, filed Oct. 2, 2001; U.S. Ser. No. 60/305,337, filed Jul. 13, 2001; and U.S. Ser. No. 60/239,330, filed Oct. 10, 2000; each of which is incorporated herein by reference.

GOVERNMENT SUPPORT

This invention was made with United States Government support under Cooperative Agreement #ECC9843342 to the MIT Biotechnology Process Engineering Center by the National Science Foundation, under contract GM26698 and NRSA Fellowship # 1 F32 GM20227-01 by the National Institutes of Health, and under Cooperative Agreement DAMD 17-99-2-9-001 to the Center for Innovative Minimally Invasive Therapy by the Department of the Army. The United States Government has certain rights in the invention.

BACKGROUND OF THE INVENTION

The treatment of human diseases through the application of nucleotide-based drugs such as DNA and RNA has the potential to revolutionize the field of medicine (Anderson *Nature* 392(Suppl.):25-30, 1996; Friedman *Nature Med.* 2:144-147, 1996; Crystal *Science* 270:404-410, 1995; Mulligan *Science* 260:926-932, 1993; each of which is incorporated herein by reference). Thus far, the use of modified viruses as gene transfer vectors has generally represented the most clinically successful approach to gene therapy. While viral vectors are currently the most efficient gene transfer agents, concerns surrounding the overall safety of viral vectors, which include the potential for unsolicited immune responses, have resulted in parallel efforts to develop non-viral alternatives (for leading references, see: Luo et al. *Nat. Biotechnol.* 18:33-37, 2000; Behr Acc. *Chem. Res.* 26:274-278, 1993; each of which is incorporated herein by reference). Current alternatives to viral vectors include polymeric delivery systems (Zauner et al. *Adv. Drug Del. Rev.* 30:97-113, 1998; Kabanov et al. *Bioconjugate Chem.* 6:7-20, 1995; each of which is incorporated herein by reference), liposomal formulations (Miller *Angew. Chem. Int. Ed.* 37:1768-1785, 1998; Hope et al. *Molecular Membrane Technology* 15:1-14, 1998; Deshmukh et al. *New J. Chem.* 21:113-124, 1997; each of which is incorporated herein by reference), and "naked" DNA injection protocols (Sanford *Trends Biotechnol.* 6:288-302, 1988; incorporated herein by reference). While these strategies have yet to achieve the clinical effectiveness of viral vectors, the potential safety, processing, and economic benefits offered by these methods (Anderson *Nature* 392(Suppl.):25-30, 1996; incorporated herein by reference) have ignited interest in the continued development of non-viral approaches to gene therapy (Boussif et al *Proc. Natl. Acad. Sci. USA* 92:7297-7301, 1995; Putnam et al *Macromolecules* 32:3658-3662, 1999; Lim et al. *J. Am. Chem. Soc.* 121:5633-5639, 1999; Gonzalez et al. *Bioconjugate Chem.* 10:1068-1074, 1999; Kukowska-Latallo et al. *Proc. Natl. Acad. Sci. USA* 93:4897-4902, 1996; Tang et al. *Bioconjugate Chem.* 7:703-714, 1996; Haensler et al. *Bioconjugate Chem.* 4:372-379, 1993; each of which is incorporated herein by reference).

Cationic polymers have been widely used as transfection vectors due to the facility with which they condense and protect negatively charged strands of DNA. Amine-containing polymers such as poly(lysine) (Zauner et al. *Adv. Drug Del. Rev.* 30:97-113, 1998; Kabanov et al. *Bioconjugate Chem.* 6:7-20, 1995; each of which is incorporated herein by reference), poly(ethylene imine) (PEI) (Boussif et al *Proc. Natl. Acad. Sci. USA* 92:7297-7301, 1995; incorporated herein by reference), and poly(amidoamine) dendrimers (Kukowska-Latallo et al. *Proc. Natl. Acad. Sci. USA* 93:4897-4902, 1996; Tang et al. *Bioconjugate Chem.* 7:703-714, 1996; Haensler et al. *Bioconjugate Chem.* 4:372-379, 1993; each of which is incorporated herein by reference) are positively-charged at physiological pH, form ion pairs with nucleic acids, and mediate transfection in a variety of cell lines. Despite their common use, however, cationic polymers such as poly(lysine) and PEI can be significantly cytotoxic (Zauner et al. *Adv. Drug Del. Rev.* 30:97-113, 1998; Deshmukh et al. *New J. Chem.* 21:113-124, 1997; Choksakulnimitr et al. *Controlled Release* 34:233-241, 1995; Brazeau et al. *Pharm. Res.* 15:680-684, 1998; each of which is incorporated herein by reference). As a result, the choice of cationic polymer for a gene transfer application generally requires a trade-off between transfection efficiency and short- and long-term cytotoxicity. Additionally, the long-term biocompatibility of these polymers remains an important issue for use in therapeutic applications in vivo, since several of these polymers are not readily biodegradable (Uhrich *Trends Polym. Sci.* 5:388-393, 1997; Roberts et al. *J. Biomed. Mater. Res.* 30:53-65, 1996; each of which is incorporated herein by reference).

In order to develop safe alternatives to existing polymeric vectors and other functionalized biomaterials, degradable polyesters bearing cationic side chains have been developed (Putnam et al. *Macromolecules* 32:3658-3662, 1999; Barrera et al. *J. Am. Chem. Soc.* 115:11010-11011, 1993; Kwon et al. *Macromolecules* 22:3250-3255, 1989; Lim et al. *J. Am. Chem. Soc.* 121:5633-5639, 1999; Zhou et al. *Macromolecules* 23:3399-3406, 1990; each of which is incorporated herein by reference). Examples of these polyesters include poly(L-lactide-co-L-lysine) (Barrera et al. *J. Am. Chem. Soc.* 115:11010-11011, 1993; incorporated herein by reference), poly(serine ester) (Zhou et al. *Macromolecules* 23:3399-3406, 1990; each of which is incorporated herein by reference), poly(4-hydroxy-L-proline ester) (Putnam et al. *Macromolecules* 32:3658-3662, 1999.; Lim et al. *J. Am. Chem. Soc.* 121:5633-5639, 1999; each of which is incorporated herein by reference), and more recently, poly[α-(4-aminobutyl)-L-glycolic acid]. Poly(4-hydroxy-L-proline ester) and poly[α-(4-aminobutyl)-L-glycolic acid] were recently demonstrated to condense plasmid DNA through electrostatic interactions, and to mediate gene transfer (Putnam et al. *Macromolecules* 32:3658-3662, 1999; Lim et al. *J. Am. Chem. Soc.* 121:5633-5639, 1999; each of which is incorporated herein by reference). Importantly, these new polymers are significantly less toxic than poly(lysine) and PEI, and they degrade into non-toxic metabolites. It is clear from these investigations that the rational design of amine-containing polyesters can be a productive route to the development of safe, effective transfection vectors. Unfortunately, however, present syntheses of these polymers require either the independent preparation of specialized monomers (Barrera et al. *J. Am. Chem. Soc.* 115:11010-11011, 1993; incorporated herein by reference), or the use of stoichiometric amounts of expensive coupling reagents (Putnam et al. *Macromolecules* 32:3658-3662, 1999; incorporated herein by reference). Additionally, the amine functionalities in the monomers must be protected prior to polymerization (Putnam et al. *Macromolecules* 32:3658-3662, 1999; Lim et al. *J. Am. Chem. Soc.* 121:5633-5639, 1999; Gonzalez et al *Bioconjugate Chem.* 10:1068-1074, 1999; Barrera et al. *J. Am. Chem. Soc.* 115:11010-11011, 1993; Kwon et al. *Macromolecules* 22:3250-3255, 1989; each of which is incorporated herein by reference), necessitating additional post-polymerization deprotection steps before the polymers can be used as transfection agents.

There exists a continuing need for non-toxic, biodegradable, biocompatible polymers that can be used to transfect nucleic acids and that are easily prepared efficiently and economically. Such polymers would have several uses, including the delivery of nucleic acids in gene therapy as well as in the packaging and/or delivery of diagnostic, therapeutic, and prophylactic agents.

SUMMARY OF THE INVENTION

The present invention provides novel end-modified poly (beta-amino esters) useful in a variety of medical applications including drug delivery, tissue engineering, and biomaterials and non-medical applications including coatings, plastics, paints, and films. In certain embodiments, the inventive end-modified poly(beta-amino esters) are prepared by the addition of a nucleophilic reagent (e.g., an amine) to an acrylate-terminated poly(beta-amino ester). In other embodiments, the inventive end-modified poly(beta-amino esters) are prepared by the addition of an electrophilic reagent (e.g., acrylate, acrylamide) to an acrylate-terminated poly(beta-amino ester). Any acrylate-terminated poly(beta-amino ester) or nucleophilic reagent may be used to prepare an end-modified poly(beta-amino ester). In addition to poly(beta-amino esters), poly(beta-amino amides) as well as other polymers with reactive end moieties may be end-modified. The resulting end-modified polymers are useful in drug delivery, particularly in the delivery of polynucleotides. The invention also provides complexes of the inventive end-modified polymers with polynucleotides, drug delivery devices (e.g., microparticles, nanoparticles) including the inventive polymers, methods of preparing end-modified poly(beta-amino esters), and methods of using the inventive end-modified polymers.

In one aspect, the invention provides end-terminated poly (beta-amino esters). The inventive polymers are generally of one of the formulae:

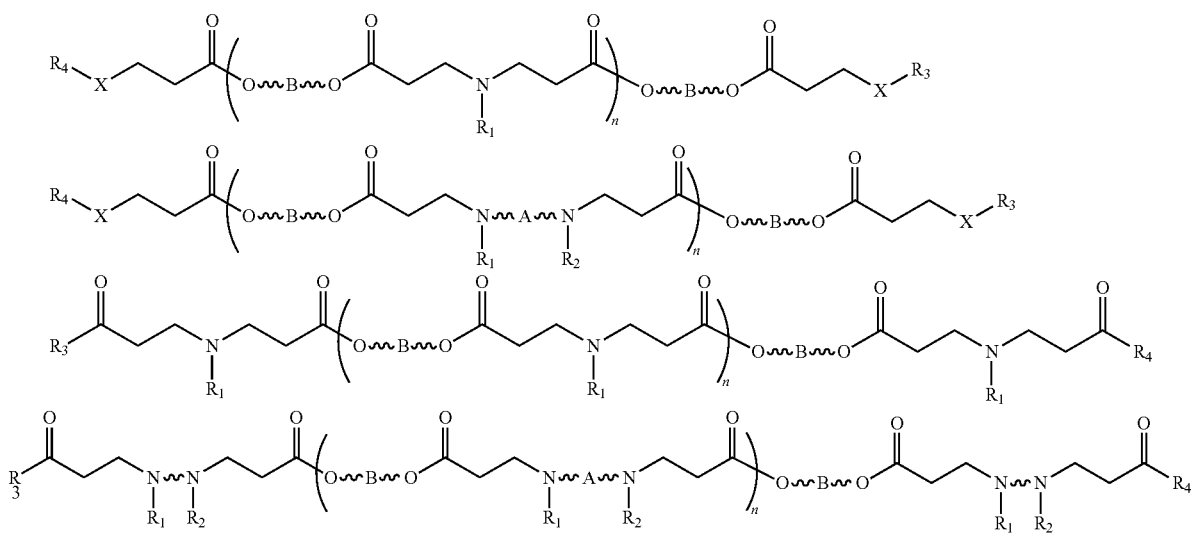

wherein A and B are linkers which may be any substituted or unsubstituted, branched or unbranched, cyclic or acyclic aliphatic or heteroaliphatic moiety; or substituted or unsubstituted aryl or heteroaryl moieties;

each of $R_1$, $R_2$, $R_3$, and $R_4$ are independently a hydrogen; halogen; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic or acyclic acyl; substituted or unsubstituted aryl; or substituted or unsubstituted heteroaryl; and X is O, S, NH, or $NR_X$, wherein $R_X$ is halogen; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic or acyclic acyl; substituted or unsubstituted aryl; or substituted or unsubstituted heteroaryl. In certain embodiments, the terminal groups of the end-modified polymers are the same. In other embodiments, the terminal groups are different. Any of the poly(beta-amino esters) described in U.S. patent applications U.S. Ser. No. 09/969,431 and U.S. Ser. No. 10/446,444, each of which is incorporated herein by reference, could be used to prepare an end-modified polymer. The molecular weights of the inventive polymers may range from 1000 g/mol to 20,000 g/mol, preferably from 5,000 g/mol to 15,000 g/mol.

In another aspect, the invention provides end-terminated poly(beta-amino amides). The inventive polymers are generally of one of the formulae:

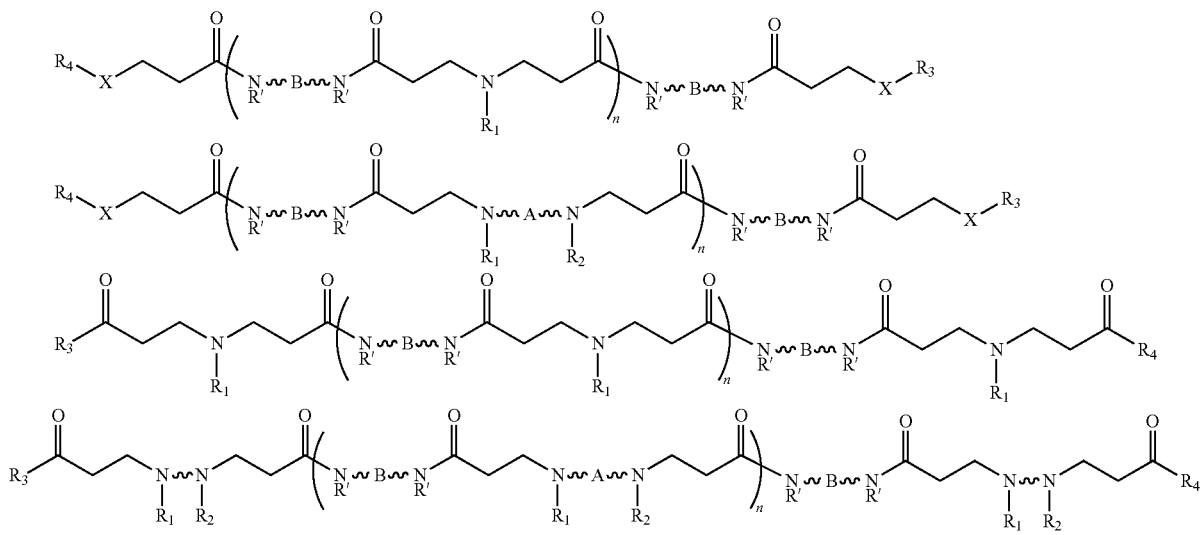

wherein A and B are linkers which may be any substituted or unsubstituted, branched or unbranched, cyclic or acyclic aliphatic or heteroaliphatic moiety; or substituted or unsubstituted aryl or heteroaryl moieties;

each R' is independently a hydrogen; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic or acyclic acyl; substituted or unsubstituted aryl; or substituted or unsubstituted heteroaryl;

each of $R_1$, $R_2$, $R_3$, and $R_4$ are independently a hydrogen; halogen; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic or acyclic acyl; substituted or unsubstituted aryl; or substituted or unsubstituted heteroaryl; and each X is independently O, S, NH, or $NR_X$, wherein $R_X$ is halogen; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic or acyclic acyl; substituted or unsubstituted aryl; or substituted or unsubstituted heteroaryl; and salts thereof. In certain embodiments, the terminal groups of the end-modified polymers are the same. In other embodiments, the terminal groups are different. In certain embodiments, all R' are hydrogen. In other embodiments, all R' are $C_1$-$C_6$ alkyl. The molecular weights of the inventive polymers may range from 1000 g/mol to 20,000 g/mol, preferably from 5,000 g/mol to 15,000 g/mol. In certain embodiments, a salt of the inventive end-modified polymers is used, for example, cationic salts such as sodium, magnesium, potassium, zinc, calcium, etc., or anionic salts such chloride, bromide, iodide, sulfate, phosphate, etc.

The present invention also provides end-modified polymers wherein the ends of the polymers are serially modified. For example, in certain embodiments, an acrylate-terminated poly(beta-amino ester) or poly(beta-amino amide) is reacted with a nucleophile which results in another reactive moiety (e.g., an amino group, hydroxyl group, thiol group) being placed at the end of the polymer. This reactive moiety is subsequently modified. For example, a terminal amino group may be subsequently modified by the addition of an electrophile (e.g., an acrylate, acrylamide, alkyl halide, etc.). To give but another example, in certain embodiments, an amine-terminated poly(beta-amino ester) or poly(beta-amino amide) is reacted with an electrophile which results in another reactive moiety (e.g., an amino group, hydroxyl group, thiol group) being placed at the end of the polymer. This process of serially modifying the end of a polymer can be continued for any number of rounds. In certain embodiments, the process is continued for at least 2, 3, 4, 5, 6, 7, 8, 9, 10, 15, 20, or more rounds. The desired polymer may optionally be purified after each round of end-modification.

The present invention also provides methods of preparing the inventive end-modified poly(beta-amino esters) and poly (beta-amino esters). In certain embodiments, the methods begins by starting with an acylate-terminated polymer or by preparing such a polymer from a bisacrylate and an amine, or a bisacrylamide and an amine. The acrylate-terminated polymer is reacted with a nucleophile under conditions suitable for the nucleophile to add to the terminal acrylate moieties of the polymer. In certain other embodiments, the methods begins by starting with an amine-terminated polymer or by preparing such a polymer from a bisacrylate and an amine, or a bisacrylamide and an amine. The amine-terminated polymer is reacted with an electrophile under conditions suitable for the nucleophile to add to the terminal amine moieties of the polymer. The resulting end-modified polymers may then be optionally purified or characterized. The inventive polymer may find use in drug delivery or other biomedical applications. The inventive polymers may also be used in the myriad of ways other polymers are used. For example, the inventive polymers may be used in manufacturing materials, coatings, nanodevices, etc.

In certain aspects of the invention, the inventive polymers are used to encapsulate therapeutic, diagnostic, and/or prophylactic agents including polynucleotides, peptides, proteins, cells, biomolecules, small molecules, etc. For example, the end-modified polymers may be used to form particles, microparticles, nanoparticles, or other drug delivery devices. The end-modified polymers terminated with an amine or other group that is easily ionizable to form a positive ion are particularly useful in complexing or delivering negatively-charged payloads such as polynucleotides. Other larger particles or devices may also be prepared from the inventive polymers.

In yet another aspect, the invention provides a system for synthesizing and screening a collection of the inventive end-modified polymers. In certain embodiments, the system takes advantage of techniques known in the art of automated liquid handling and robotics. The system of synthesizing and screening is used with various end-modified poly(beta-amino esters) and end-modified poly(beta-amino amides). Various modifications may be made to these polymers found in the collection including the bisacrylates, bisacrylamides, or amines used in preparing the core polymer and the nucleophile used to modify the terminal acrylate or amino moieties. Hundreds to thousands of the inventive end-modified polymers may be synthesized and screened in parallel using the inventive system. In certain embodiments, the polymers are screened for properties useful in the field of drug delivery, ability to complex polynucleotides, ability to form particles, biocompatibility, biodegradability, mechanical properties, etc.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry, Thomas Sorrell, University Science Books, Sausalito,* 1999; Smith and March *March's Advanced Organic Chemistry,* 5 th Edition, John Wiley & Sons, Inc., New York, 2001; Larock, *Comprehensive Organic Transformations,* VCH Publishers, Inc., New York, 1989; Carruthers, *Some Modern Methods of Organic Synthesis, 3$^{rd}$* Edition, Cambridge University Press, Cambridge, 1987; the entire contents of each of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

It will be appreciated that the polymers, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term acyl as used herein refers to a group having the general formula —C(=O)R, where R is alkyl, alkenyl, alkynyl, aryl, alkoxy, hydroxy, thiol. alkylthioxy, amino, alkylamino, dialkylamino, carbocylic, heterocyclic, or aromatic heterocyclic. An example of an acyl group is acetyl.

The term aliphatic, as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

The term alkyl as used herein refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-10 carbon atoms. In another embodiment, the alkyl group employed contains 1-8 carbon atoms. In still other embodiments, the alkyl group contains 1-6 carbon atoms. In yet another embodiments, the alkyl group contains 1-4 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substitutents.

The term alkoxy as used herein refers to a saturated (i.e., alkyl-O—) or unsaturated (i.e., alkenyl-O— and alkynyl-O—) group attached to the parent molecular moiety through an oxygen atom. In certain embodiments, the alkyl group contains 1-20 aliphatic carbon atoms. In certain other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples include, but are not limited to, methoxy, ethoxy, propoxy, isopropoxy, n-butoxy, tert-butoxy, i-butoxy, sec-butoxy, neopentoxy, n-hexoxy, and the like.

The term alkenyl denotes a monovalent group derived from a hydrocarbon moiety having at least one carbon-carbon double bond by the removal of a single hydrogen atom. In certain embodiments, the alkenyl group employed in the invention contains 1-20 carbon atoms. In some embodiments, the alkenyl group employed in the invention contains 1-10 carbon atoms. In another embodiment, the alkenyl group employed contains 1-8 carbon atoms. In still other embodiments, the alkenyl group contains 1-6 carbon atoms. In yet another embodiments, the alkenyl group contains 1-4 carbons. Alkenyl groups include, for example, ethenyl, propenyl, butenyl, 1-methyl-2-buten-1-yl, and the like.

The term alkynyl as used herein refers to a monovalent group derived form a hydrocarbon having at least one carbon-carbon triple bond by the removal of a single hydrogen atom. In certain embodiments, the alkynyl group employed in the invention contains 1-20 carbon atoms. In some embodiments, the alkynyl group employed in the invention contains 1-10 carbon atoms. In another embodiment, the alkynyl group employed contains 1-8 carbon atoms. In still other embodiments, the alkynyl group contains 1-6 carbon atoms. Representative alkynyl groups include, but are not limited to, ethynyl, 2-propynyl (propargyl), 1-propynyl, and the like.

The term alkylamino, dialkylamino, and trialkylamino as used herein refers to one, two, or three, respectively, alkyl groups, as previously defined, attached to the parent molecular moiety through a nitrogen atom. The term alkylamino refers to a group having the structure —NHR' wherein R' is an alkyl group, as previously defined; and the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. In certain embodiments, the alkyl group contain 1-20 aliphatic carbon atoms. In certain other embodiments, the alkyl group contains 1-10 aliphatic carbon atoms. In yet other embodiments, the alkyl group contains 1-8 aliphatic carbon atoms. In still other embodiments, the alkyl group contain 1-6 aliphatic carbon atoms. In yet other embodiments, the alkyl group contain 1-4 aliphatic carbon atoms. Additionally, R', R", and/or R'" taken together may optionally be —$(CH_2)_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of thioalkoxyl moieties include, but are not limited to, methylthio, ethylthio, propylthio, isopropylthio, n-butylthio, and the like.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms aryl and heteroaryl, as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, aryl refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term heteroaryl, as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$;

—OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term carboxylic acid as used herein refers to a group of formula —CO$_2$H.

The terms halo and halogen as used herein refer to an atom selected from fluorine, chlorine, bromine, and iodine.

The term haloalkyl denotes an alkyl group, as defined above, having one, two, or three halogen atoms attached thereto and is exemplified by such groups as chloromethyl, bromoethyl, trifluoromethyl, and the like.

The term heteroaliphatic, as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term heterocyclic, as used herein, refers to an aromatic or non-aromatic, partially unsaturated or fully saturated, 3- to 10-membered ring system, which includes single rings of 3 to 8 atoms in size and bi- and tri-cyclic ring systems which may include aromatic five- or six-membered aryl or aromatic heterocyclic groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring.

The term aromatic heterocyclic, as used herein, refers to a cyclic aromatic radical having from five to ten ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. Aromatic heterocyclic groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide.

Specific heterocyclic and aromatic heterocyclic groups that may be included in the compounds of the invention include: 3-methyl-4-(3-methylphenyl)piperazine, 3 methylpiperidine, 4-(bis-(4-fluorophenyl)methyl)piperazine, 4-(diphenylmethyl)piperazine, 4-(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl)amino)ethyl)piperazine, 4-(2-(diethylamino)ethyl)piperazine, 4-(2-chlorophenyl)piperazine, 4-(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl)piperazine, 4-(2-nitrophenyl)piperazine, 4-(2-nitrophenyl)piperazine, 4-(2-phenylethyl)piperazine, 4-(2-pyridyl)piperazine, 4-(2-pyrimidinyl)piperazine, 4-(2,3-dimethylphenyl)piperazine, 4-(2,4-difluorophenyl)piperazine, 4-(2,4-dimethoxyphenyl)piperazine, 4-(2,4-dimethylphenyl)piperazine, 4-(2,5-dimethylphenyl)piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-3,4-dimethoxyphenyl)piperazine, 4-(3,4-dimethylphenyl)piperazine, 4-(3,4-methylenedioxyphenyl)piperazine, 4-(3,4,5-trimethoxyphenyl)piperazine, 4-(3,5-dichlorophenyl)piperazine, 4-(3,5-dimethoxyphenyl)piperazine, 4-(4-(phenylmethoxy)phenyl)piperazine, 4-(4-(3,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl)piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl)piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine, 6-fluoro-1,2,3,4-tetrahydro-2-methylquinoline, 1,4-diazacylcloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole.

The term carbamoyl, as used herein, refers to an amide group of the formula —$CONH_2$.

The term carbonyldioxyl, as used herein, refers to a carbonate group of the formula
—O—CO—OR.

The term hydrocarbon, as used herein, refers to any chemical group comprising hydrogen and carbon. The hydrocarbon may be substituted or unsubstituted. The hydrocarbon may be unsaturated, saturated, branched, unbranched, cyclic, polycyclic, or heterocyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents may also be further substituted (e.g., an aryl group substituent may have another substituent off it, such as another aryl group, which is further substituted with fluorine at one or more positions).

The term thiohydroxyl or thiol, as used herein, refers to a group of the formula —SH.

The following are more general terms used throughout the present application:

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a domesticated animal. An animal may be a transgenic animal.

"Associated with": When two entities are "associated with" one another as described herein, they are linked by a direct or indirect covalent or non-covalent interaction. In certain embodiments, the association is covalent. In other embodiments, the association is non-covalent. Desirable non-covalent interactions include hydrogen bonding, van der Waals interactions, hydrophobic interactions, magnetic interactions, electrostatic interactions, etc.

"Biocompatible": The term "biocompatible", as used herein is intended to describe compounds that are not toxic to cells. Compounds are "biocompatible" if their addition to cells in vitro results in less than or equal to 20% cell death, and their administration in vivo does not induce inflammation or other such adverse effects.

"Biodegradable": As used herein, "biodegradable" compounds are those that, when introduced into cells, are broken down by the cellular machinery or by hydrolysis into components that the cells can either reuse or dispose of without significant toxic effects on the cells (i.e., fewer than about 20% of the cells are killed when the components are added to cells in vitro). The components preferably do not induce inflammation or other adverse effects in vivo. In certain preferred embodiments, the chemical reactions relied upon to break down the biodegradable compounds are uncatalyzed. For example, the inventive materials may be broken down in part by the hydrolysis of the ester bonds found in cross-linked material.

"Peptide" or "protein": According to the present invention, a "peptide" or "protein" comprises a string of at least three amino acids linked together by peptide bonds. The terms "protein" and "peptide" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polynucleotide" or "oligonucleotide": Polynucleotide or oligonucleotide refers to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Small molecule": As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

DETAILED DESCRIPTION OF CERTAIN PREFERRED EMBODIMENTS OF THE INVENTION

Figure 1:
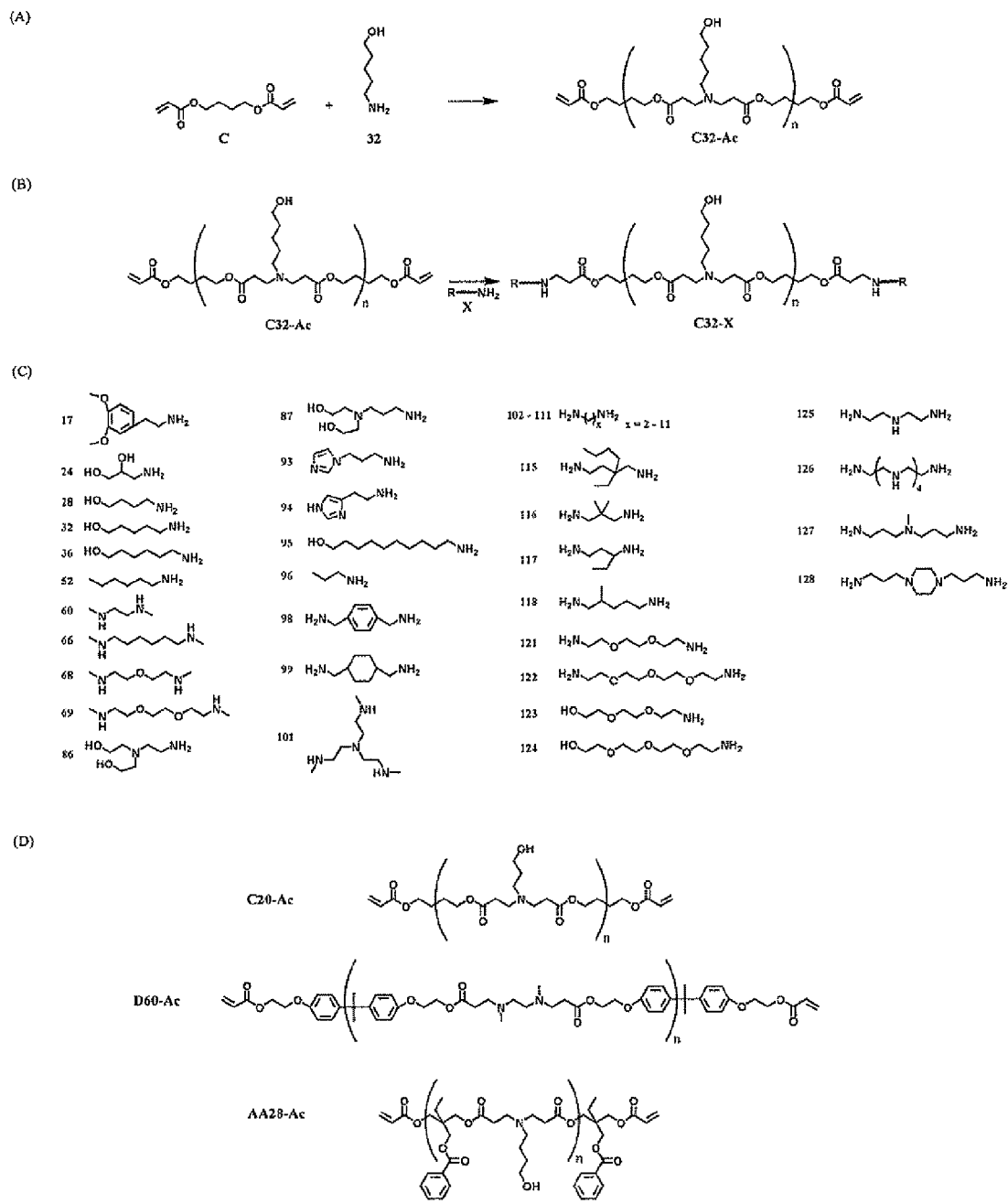
FIG. 1. (A) Synthesis of acrylate-terminated C32 polymer (C32-Ac). (B) Synthesis of end-modified C32 polymers (C32-X). (C) Amine capping molecules. (D) Structures of the acrylate-terminated C20 and D60 poly(beta-amino esters) used to demonstrate the combined effects of interior polymer sequence and end-modification on DNA delivery. End-modified derivatives of AA28 were synthesized and tested for siRNA delivery.

The present invention provides novel end-modified poly(beta-amino esters), poly(beta-amino amides), and other polymers. In certain embodiments, the inventive polymers are prepared by reacting an acrylate-terminated poly(beta-amino ester) with a nucleophile under suitable conditions to have the nucleophile added to the terminal acrylate units of the polymer. In certain embodiments, the inventive polymers are prepared by reacting an acrylate-terminated poly(beta-amino amides) with a nucleophile under suitable conditions to have the nucleophile added to the terminal acrylate units of the polymer. In certain embodiments, the inventive polymers are prepared by reacting an amine-terminated poly(beta-amino ester) with a electrophile under suitable conditions to have the electrophile added to the terminal amino units of the polymer. In certain embodiments, the inventive polymers are prepared by reacting an amine-terminated poly(beta-amino amides) with an electrophile under suitable conditions to have the electrophile react to the terminal amino units of the polymer. The end-modified polymers are useful in many different areas including drug delivery and the biomedical arts. The invention also provides methods of preparing the inventive end-modified polymers, screening these polymers for specific properties, and using these materials in the medical field and non-medical fields. In certain embodiments, a system is provided for preparing and screening a library of the inventive end-modified polymers in parallel. High-throughput techniques and devices may be used in this system. The invention also provides compositions including the inventive end-modified polymers (e.g., drug delivery devices (e.g., complexes, nanoparticles, microparticles, macroparticles, capsules, tablets), microdevices, nanodevices, tissue engineering scaffolds, plastics, films, biomedical devices, etc.)

In certain embodiments, the inventive end-modified poly(beta-amino esters) are prepared from poly(beta-amino esters). The poly(beta-amino ester) is modified at its termini with a nucleophilic reagent. Preferably, the poly(beta-amino ester) is terminated with an electrophilic moiety such as an acrylate or methacrylate. Such $\alpha,\beta$-unsaturated esters are susceptible to 1,4-addition by a nucleophilic reagent thereby resulting in the end-modified poly(beta-amino ester). In certain embodiments, the reaction conditions and reagent are such that the 1,4-addition to the $\alpha,\beta$-unsaturated carbonyl is favored over the 1,2-addition. Poly(beta-amino esters) and the preparation of these polymers are described in U.S. patent applications U.S. Ser. No. 11/099,886, filed Apr. 6, 2005; U.S. Ser. No. 10/446,444, filed May 28, 2003; U.S. Ser. No. 09/969,431, filed Oct. 2, 2001; U.S. Ser. No. 60/305,337, filed Jul. 13, 2001; and U.S. Ser. No. 60/239,330, filed Oct. 10, 2000; each of which is incorporated herein by reference. These polymers are prepared by the conjugate addition of a primary amine or a bis(secondary amine) to diacrylates. Preferably, the polymers are terminated with an acrylate unit; therefore, the preparation of the polymer is done with an excess of acrylate. These polymers have already been shown to be particularly useful in drug delivery such as the delivery of polynucleotides due to the presence of tertiary amines in the backbone of the polymer. These polymers and their end-modified variants are also useful in the medical and non-medical arts because of the biodegradable nature of the ester linkages in the polymers. The inventive end-modified poly(beta-amino esters) are prepared by the addition of a nucleophile to the end(s) of the polymer. The resulting end-modified polymers are useful in a variety of applications including the medical and non-medical fields.

In other embodiments, poly(beta-amino amides) are similarly end-modified as described above for poly(beta-amino esters). In yet other embodiments, other polymers with reactive terminal moieties are end-modified by the inventive system. The resulting end-modified polymers, method of preparing the end-modified polymers, methods of using the end-modified polymers, and compositions comprising the end-modified polymers are considered part of the present invention.

Poly(Beta-Amino Esters)

Poly(beta-amino esters) are used as the starting material in preparing the inventive end-modified poly(beta-amino esters). Any size of polymer of poly(beta-amino esters) may be useful in the preparation of the inventive crosslinked materials. In certain embodiments, the molecular weights of the polymers range from 1,000 g/mol to over 100,000 g/mol, more preferably from 1,000 g/mol to 50,000 g/mol. In certain embodiments, the molecular weights of the polymers range from 500 g/mol to 10,000 g/mol. In other embodiments, the molecular weights of the polymers range from 1,000 g/mol to 25,000 g/mol. In certain embodiments, the molecular weights of the polymers range from 2,000 g/mol to 15,000 g/mol. In certain embodiments, the average molecular weight of the polymer is approximately 1,000 g/mol, 2,000 g/mol, 3,000 g/mol, 4,000 g/mol, 5,000 g/mol, 6,000 g/mol, 7,000 g/mol, 8,000 g/mol, 9,000 g/mol, 10,000 g/mol, 11,000 g/mol, 12,000 g/mol, 13,000 g/mol, 14,000 g/mol, 15,000 g/mol, 16,000 g/mol, 17,000 g/mol, 18,000 g/mol, 19,000 g/mol, or 20,000 g/mol. In certain embodiments, even smaller polymers are used. In other embodiments, even larger polymers are used. In a particularly preferred embodiment, the polymers are relatively non-cytotoxic. In another particularly preferred embodiment, the polymers are biocompatible and biodegradable. In another embodiment, the polymers of the present invention have p$K_a$s in the range of 5.5 to 7.5, more preferably between 6.0 and 7.0. In another embodiment, the polymer may be designed to have a desired p$K_a$ between 3.0 and 9.0, more preferably between 5.0 and 8.0. In certain embodiments, the polymer has more than one acidic and/or basic moiety resulting in more than one pKa.

The poly(beta-amino esters) useful in preparing the inventive end-modified polymers include a terminal electrophilic group suitable for addition of the nucleophile. The polymers typically have an acrylate or methacrylate group at each end of the polymer. Acrylate-terminated polymers are easily prepared by using an excess of acrylate in the synthesis of the poly(beta-amino ester). In certain embodiments, the polymer ends with a functional group of formula:

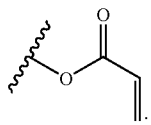

In other embodiments, the polymer ends with a functional group of formula:

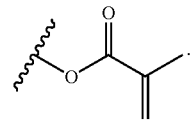

The acrylate-terminated poly(beta-amino ester) is reacted with a nucleophile to yield an end-modified polymer of formulae:

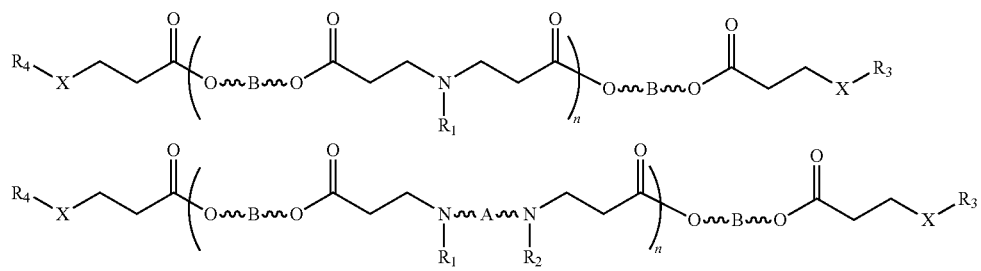

wherein

A and B are linkers which may be any substituted or unsubstituted, branched or unbranched, cyclic or acyclic aliphatic or heteroaliphatic moiety; or substituted or unsubstituted aryl or heteroaryl moieties;

each of $R_1$, $R_2$, $R_3$, and $R_4$ are independently a hydrogen; halogen; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic or acyclic acyl; substituted or unsubstituted aryl; or substituted or unsubstituted heteroaryl; and each X is independently O, S, NH, or $NR_X$, wherein $R_X$ is halogen; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic or acyclic acyl; substituted or unsubstituted aryl; or substituted or unsubstituted heteroaryl; and salts thereof.

The poly(beta-amino esters) useful in preparing the inventive end-modified polymers include a terminal nucleophile group suitable for reacting with an electrophile. In certain embodiments, the polymers have an amino group at each end of the polymer. Amine-terminated polymers are easily prepared by using an excess of amine in the synthesis of the poly(beta-amino ester). In certain embodiments, the polymer ends with a functional group of formula —$NH_2$. In other embodiments, the polymer ends with a functional group of formula —NR'H, wherein R' is substituted or unsubstituted, branched or unbranched, cyclic or acyclic aliphatic or heteroaliphatic; substituted or unsubstituted acyl; or substituted or unsubstituted aryl or heteroaryl. In certain embodiments, R' is $C_1$-$C_6$ alkyl.

The amine-terminated poly(beta-amino ester) is reacted with an electrophile to yield an end-modified polymer of formulae:

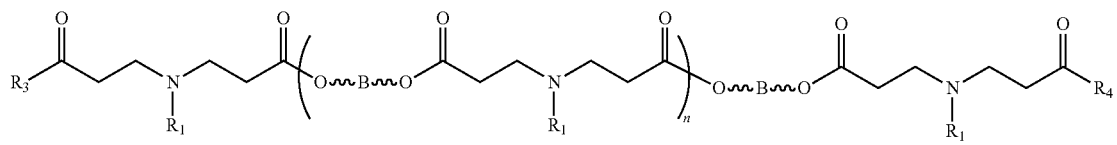

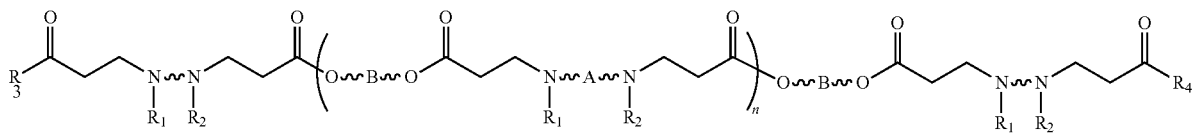

wherein

A and B are linkers which may be any substituted or unsubstituted, branched or unbranched, cyclic or acyclic aliphatic or heteroaliphatic moiety; or substituted or unsubstituted aryl or heteroaryl moieties;

each of $R_1$, $R_2$, $R_3$, and $R_4$ are independently a hydrogen; halogen; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic or acyclic acyl; substituted or unsubstituted aryl; or substituted or unsubstituted heteroaryl; and each X is independently O, S, NH, or $NR_X$, wherein $R_X$ is halogen; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic or acyclic acyl; substituted or unsubstituted aryl; or substituted or unsubstituted heteroaryl; and salts thereof In certain embodiments, an acrylate-terminated poly(beta-amino amide) is reacted with a nucleophile to yield an end-modified polymer of formulae:

each R' is independently a hydrogen; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic or acyclic acyl; substituted or unsubstituted aryl; or substituted or unsubstituted heteroaryl;

each of $R_1$, $R_2$, $R_3$, and $R_4$ are independently a hydrogen; halogen; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic or acyclic acyl; substituted or unsubstituted aryl; or substituted or unsubstituted heteroaryl; and each X is independently O, S, NH, or $NR_X$, wherein $R_X$ is halogen; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic

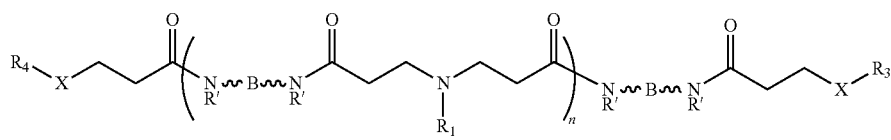

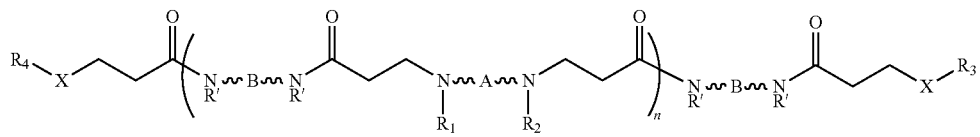

wherein

A and B are linkers which may be any substituted or unsubstituted, branched or unbranched, cyclic or acyclic aliphatic or heteroaliphatic moiety; or substituted or unsubstituted aryl or heteroaryl moieties;

or acyclic acyl; substituted or unsubstituted aryl; or substituted or unsubstituted heteroaryl; and salts thereof.

In other embodiments, an amine-terminated poly(beta-amino amide) is reacted with an electrophile to yield an end-modified polymer of formulae:

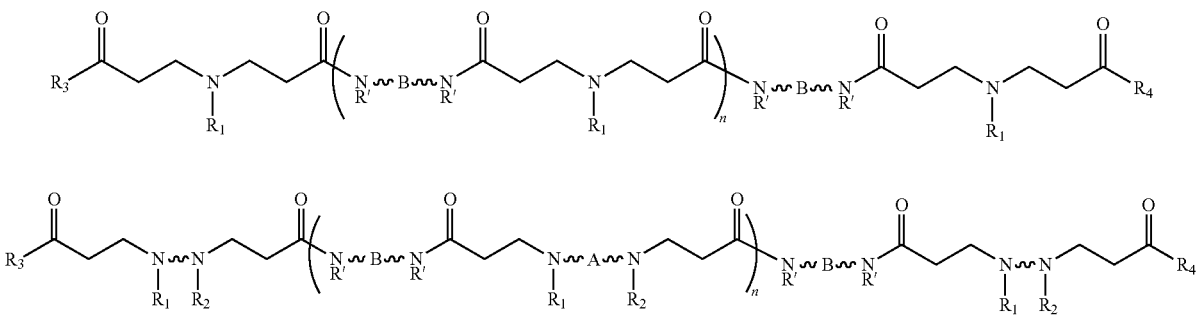

wherein

A and B are linkers which may be any substituted or unsubstituted, branched or unbranched, cyclic or acyclic aliphatic or heteroaliphatic moiety; or substituted or unsubstituted aryl or heteroaryl moieties;

each R' is independently a hydrogen; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic or acyclic acyl; substituted or unsubstituted aryl; or substituted or unsubstituted heteroaryl;

each of $R_1$, $R_2$, $R_3$, and $R_4$ are independently a hydrogen; halogen; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic or acyclic acyl; substituted or unsubstituted aryl; or substituted or unsubstituted heteroaryl; and each X is independently O, S, NH, or $NR_X$, wherein $R_X$ is halogen; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic or acyclic acyl; substituted or unsubstituted aryl; or substituted or unsubstituted heteroaryl; and salts thereof.

In certain embodiments, all R' are hydrogen. In other embodiments, all R' are $C_1$-$C_6$ alkyl. In yet other embodiments, all R' are methyl. In certain embodiments, all R' are acyl.

The linkers A and B are each a chain of atoms covalently linking the amino groups and ester groups, respectively. These linkers may contain carbon atoms or heteroatoms (e.g., nitrogen, oxygen, sulfur, etc.). Typically, these linkers are 1 to 30 atoms long, more preferably 1-15 atoms long. The linkers may contain cyclic structures including aromatic and non-aromatic structures. The linker may include aromatic structures including aryl and heteroaryl groups. The linkers may be substituted with various substituents including, but not limited to, hydrogen, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. In certain embodiments, the linker A or B is unbranched alkylidene moieties of 1-20 carbons. In certain embodiments, the linker A or B is unbranched alkylidene moieties of 1-12 carbons. In certain embodiments, the linker A or B is unbranched alkylidene moieties of 1-6 carbons. In certain embodiments, the linker A or B is branched alkylidene moieties of 1-20 carbons. In certain embodiments, the linker A or B is branched alkylidene moieties of 1-12 carbons. In certain embodiments, the linker A or B is branched alkylidene moieties of 1-6 carbons. In certain embodiments, the linker A or B is a polyethylene glycol linker. In certain embodiments, the linker A or B is a polyethylene glycol linker of 3-25 atoms in length. In certain embodiments, the linker A or B is a polyethylene glycol linker of 3-18 atoms in length. As would be appreciated by one of skill in this art, each of these groups may in turn be substituted.

The groups $R_1$, $R_2$, $R_3$, and $R_4$ may be any chemical groups including, but not limited to, hydrogen atoms, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, alkylthioether, thiol, and ureido groups. In certain embodiments, $R_1$ and $R_2$ are the same. In certain embodiments, $R_3$ and $R_4$ are the same. In other embodiments, $R_3$ and $R_4$ are different. In certain embodiments, $R_1$, $R_3$, and $R_4$ are the same. In other embodiments, $R_3$ and $R_4$ are aliphatic. In certain other embodiments, $R_3$ and $R_4$ are heteroaliphatic. In yet other embodiments, $R_3$ and $R_4$ are aryl. In still other embodiments, $R_3$ and $R_4$ are heteroaryl. In certain embodiments, $R_3$ and $R_4$ are independently $C_1$-$C_{12}$ alkyl. In other embodiments, $R_3$ and $R_4$ are $C_1$-$C_6$ alkyl. In certain embodiments, $R_3$ and $R_4$ are independently $C_2$-$C_{12}$ alkenyl. In other embodiments, $R_3$ and $R_4$ are $C_2$-$C_6$ alkenyl. In certain embodiments, $R_3$ and $R_4$ are independently $C_2$-$C_{12}$ alkynyl. In other embodiments, $R_3$ and $R_4$ are $C_1$-$C_6$ alkynyl.

In certain embodiments, the amine used to prepare the poly(beta-amino ester) is a cyclic secondary diamine. End-modified version of such a poly(beta-amino ester) are of the formula:

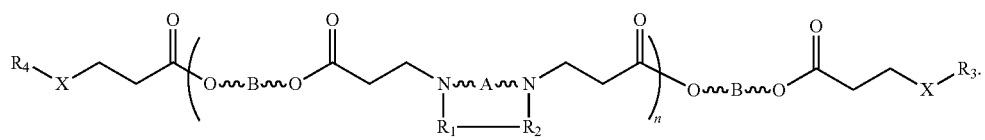

gen, aryl, heterocyclic, aromatic heterocyclic, cyano, amide, carbamoyl, carboxylic acid, ester, thioether, alkylthioether, $R_1$ and $R_2$ form a cyclic structure along with the two N atoms and the linker A.

In other embodiments, the groups $R_1$ and/or $R_2$ are covalently bonded to linker A to form one or two cyclic structures. The end-modified polymers of the present embodiment are generally represented by the formula below in which both $R_1$ and $R_2$ are bonded to linker A to form two cyclic structures:

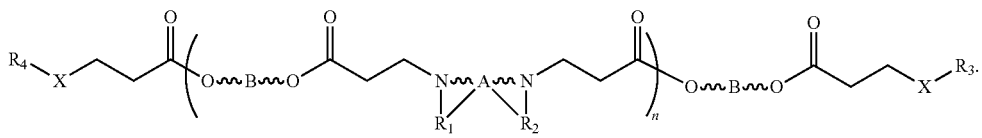

In certain embodiments, the amine used to prepare the poly(beta-amino amide) is a cyclic secondary diamine. End-modified version of such a poly(beta-amino amide) are of the formula:

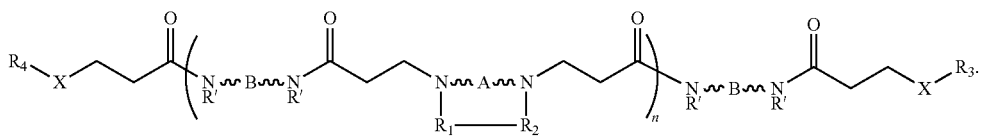

$R_1$ and $R_2$ form a cyclic structure along with the two N atoms and the linker A.

In other embodiments, the groups $R_1$ and/or $R_2$ are covalently bonded to linker A to form one or two cyclic structures. The end-modified polymers of the present embodiment are generally represented by the formula below in which both $R_1$ and $R_2$ are bonded to linker A to form two cyclic structures:

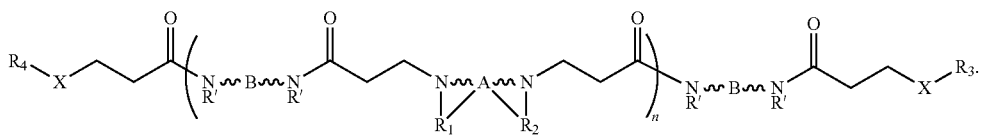

In certain embodiments, X is O. In certain embodiments, X is S. In other embodiments, X is NH. In yet other embodiments, X is $NR_X$. In certain embodiments, X is $NR_X$, wherein $R_X$ is $C_1$-$C_6$ alkyl. In certain particular embodiments, $NR_X$ is NMe. In other embodiments, $NR_X$ is NEt. In certain embodiments, both X are the same. In certain embodiments, both X are NRX (e.g., NH). In other embodiments, both X are O. In other embodiments, the X are different. For example, in certain embodiments, one X is O, and the other is $NR_X$ (e.g., NH). In certain embodiments, one X is S, and the other is O.

In certain embodiments, $R_3$ and $R_4$ are

wherein m is an integer between 1 and 20, inclusive. In certain embodiments, m is an integer between 2 and 15, inclusive. In yet other embodiments, m is an integer between 2 and 12, inclusive. In other embodiments, m is an integer between 2 and 10, inclusive. In other embodiments, m is an integer between 2 and 6, inclusive. In still other embodiments, m is an integer between 2 and 3, inclusive.

In certain embodiments, $R_3$ and $R_4$ are

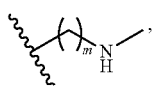

wherein m is an integer between 1 and 20, inclusive. In certain embodiments, m is an integer between 2 and 15, inclusive. In yet other embodiments, m is an integer between 2 and 12, inclusive. In other embodiments, m is an integer between 2 and 10, inclusive. In other embodiments, m is an integer between 2 and 6, inclusive. In still other embodiments, m is an integer between 2 and 3, inclusive.

In certain embodiments, $R_3$ and $R_4$ are

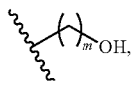

wherein m is an integer between 1 and 20, inclusive. In certain embodiments, m is an integer between 2 and 15, inclusive. In yet other embodiments, m is an integer between 2 and 12, inclusive. In other embodiments, m is an integer between 2 and 10, inclusive. In other embodiments, m is an integer between 2 and 6, inclusive. In still other embodiments, m is an integer between 1 and 3, inclusive.

In certain embodiments, $R_3$ and $R_4$ are

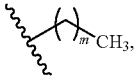

wherein m is an integer between 0 and 20, inclusive. In certain embodiments, m is an integer between 0 and 15, inclusive. In yet other embodiments, m is an integer between 0 and 12, inclusive. In other embodiments, m is an integer between 0 and 10, inclusive. In other embodiments, m is an integer between 0 and 6, inclusive. In still other embodiments, m is an integer between 0 and 3, inclusive. In certain embodiments, n is 0, 1, 2, 3, 4, 5, or 6.

In certain embodiments, $R_3$ and $R_4$ are

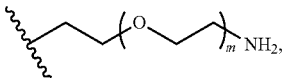

wherein m is an integer between 0 and 20, inclusive. In certain embodiments, m is an integer between 1 and 15, inclusive. In yet other embodiments, m is an integer between 1 and 12, inclusive. In other embodiments, m is an integer between 1 and 10, inclusive. In other embodiments, m is an integer between 0 and 6, inclusive. In still other embodiments, m is an integer between 0 and 3, inclusive. In certain embodiments, m is 0, 1, 2, 3, 4, 5, or 6. In certain embodiments, the terminal amino group of $R_3$ and/or $R_4$ is protected, alkylated (e.g., $C_1$-$C_{12}$ alkyl), acylated (e.g., acetyl), or otherwise modified.

In certain embodiments, $R_3$ and $R_4$ are

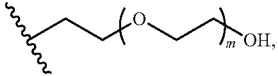

wherein m is an integer between 0 and 20, inclusive. In certain embodiments, m is an integer between 1 and 15, inclusive. In yet other embodiments, m is an integer between 1 and 12, inclusive. In other embodiments, m is an integer between 1 and 10, inclusive. In other embodiments, m is an integer between 0 and 6, inclusive. In still other embodiments, m is an integer between 0 and 3, inclusive. In certain embodiments, m is 0, 1, 2, 3, 4, 5, or 6. In certain embodiments, the terminal hydroxyl group of $R_3$ and/or $R_4$ is protected, alkylated (e.g., $C_1$-$C_{12}$ alkyl), acylated (e.g., acetyl), or otherwise modified.

In certain embodiments, $R_3$ and $R_4$ are

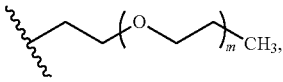

wherein m is an integer between 0 and 20, inclusive. In certain embodiments, m is an integer between 1 and 15, inclusive. In yet other embodiments, m is an integer between 1 and 12, inclusive. In other embodiments, m is an integer between 1 and 10, inclusive. In other embodiments, m is an integer between 0 and 6, inclusive. In still other embodiments, m is an integer between 0 and 3, inclusive. In certain embodiments, m is 0, 1, 2, 3, 4, 5, or 6.

In certain embodiments, $R_3$ and $R_4$ are

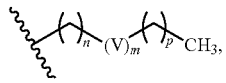

wherein n, m, and p are each independently an integer between 0 and 20, inclusive; and V is —O—, —S—, —NH—, —NR$_V$—, or C(R$_V$)$_2$, wherein R$_V$ is hydrogen, hydroxyl, $C_{1-6}$aliphatic, $C_{1-6}$heteroaliphatic, $C_{1-6}$alkoxy, amino, $C_{1-6}$alkylamino, di($C_{1-6}$alkyl)amino, aryl, heteroaryl, thiol, alkylthioxy, or acyl. In certain embodiments, n, m, and p are each independently an integer between 1 and 15, inclusive. In yet other embodiments, n, m, and p are each independently an integer between 1 and 12, inclusive. In other embodiments, n, m, and p are each independently an integer between 1 and 10, inclusive. In other embodiments, n, m, and p are each independently an integer between 0 and 6, inclusive. In still other embodiments, n, m, and p are each independently an integer between 0 and 3, inclusive. In certain embodiments, n, m, and p are each independently 0, 1, 2, 3, 4, 5, or 6.

In certain embodiments, $R_3$ and $R_4$ are

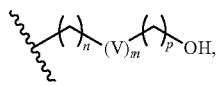

wherein n, m, and p are each independently an integer between 0 and 20, inclusive; and V is —O—, —S—, —NH—, —NR$_V$—, or C(R$_V$)$_2$, wherein R$_V$ is hydrogen, hydroxyl, $C_{1-6}$aliphatic, $C_{1-6}$heteroaliphatic, $C_{1-6}$alkoxy, amino, $C_{1-6}$alkylamino, di($C_{1-6}$alkyl)amino, aryl, heteroaryl, thiol, alkylthioxy, or acyl. In certain embodiments, n, m, and p are each independently an integer between 1 and 15, inclusive. In yet other embodiments, n, m, and p are each independently an integer between 1 and 12, inclusive. In other embodiments, n, m, and p are each independently an integer between 1 and 10, inclusive. In other embodiments, n, m, and p are each independently an integer between 0 and 6, inclusive. In still other embodiments, n, m, and p are each independently an integer between 0 and 3, inclusive. In certain embodiments, n, m, and p are each independently 0, 1, 2, 3, 4, 5, or 6. In certain embodiments, the terminal hydroxyl group of $R_3$ and/or $R_4$ is protected, alkylated (e.g., $C_1$-$C_{12}$ alkyl), acylated (e.g., acetyl), or otherwise modified.

In certain embodiments, $R_3$ and $R_4$ are

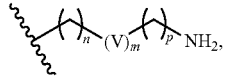

wherein n, m, and p are each independently an integer between 0 and 20, inclusive; and V is —O—, —S—, —NH—, —NR$_V$—, or C(R$_V$)$_2$, wherein R$_V$ is hydrogen, hydroxyl, $C_{1-6}$aliphatic, $C_{1-6}$heteroaliphatic, $C_{1-6}$alkoxy, amino, $C_{1-6}$alkylamino, di($C_{1-6}$alkyl)amino, aryl, heteroaryl, thiol, alkylthioxy, or acyl. In certain embodiments, n, m, and p are each independently an integer between 1 and 15, inclusive. In yet other embodiments, n, m, and p are each independently an integer between 1 and 12, inclusive. In other embodiments, n, m, and p are each independently an integer between 1 and 10, inclusive. In other embodiments, n, m, and p are each independently an integer between 0 and 6, inclusive. In still other embodiments, n, m, and p are each independently an integer between 0 and 3, inclusive. In certain embodiments, n, m, and p are each independently 0, 1, 2, 3, 4, 5, or 6. In certain embodiments, the terminal amino group of $R_3$ and/or $R_4$ is protected, alkylated (e.g., $C_1$-$C_{12}$ alkyl), acylated (e.g., acetyl), or otherwise modified.

In certain embodiments, $R_3$ and $R_4$ are

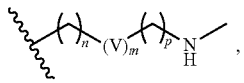

wherein n, m, and p are each independently an integer between 0 and 20, inclusive; and V is —O—, —S—, —NH—, —NR$_V$—, or C(R$_V$)$_2$, wherein R$_V$ is hydrogen, hydroxyl, $C_{1-6}$aliphatic, $C_{1-6}$heteroaliphatic, $C_{1-6}$alkoxy, amino, $C_{1-6}$alkylamino, di($C_{1-6}$alkyl)amino, aryl, heteroaryl, thiol, alkylthioxy, or acyl. In certain embodiments, n, m, and p are each independently an integer between 1 and 15, inclusive. In yet other embodiments, n, m, and p are each independently an integer between 1 and 12, inclusive. In other embodiments, n, m, and p are each independently an integer between 1 and 10, inclusive. In other embodiments, n, m, and p are each independently an integer between 0 and 6, inclusive. In still other embodiments, n, m, and p are each independently an integer between 0 and 3, inclusive. In certain embodiments, n, m, and p are each independently 0, 1, 2, 3, 4, 5, or 6.

In certain embodiments, $R_3$ and $R_4$ are selected from the group consisting of:

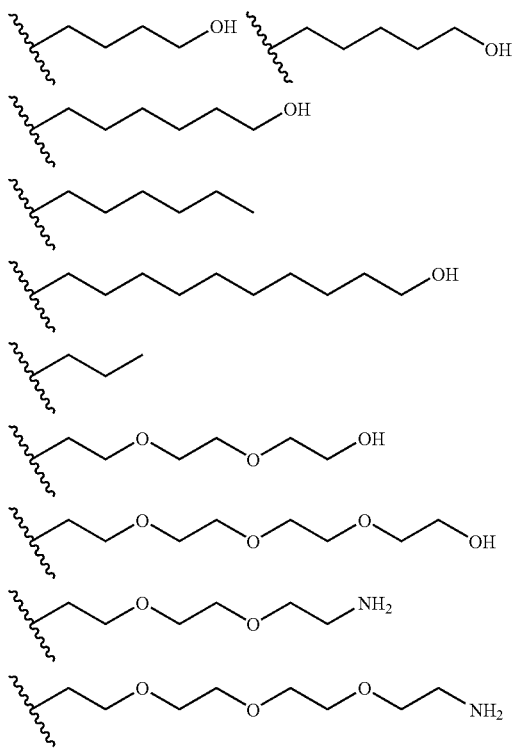

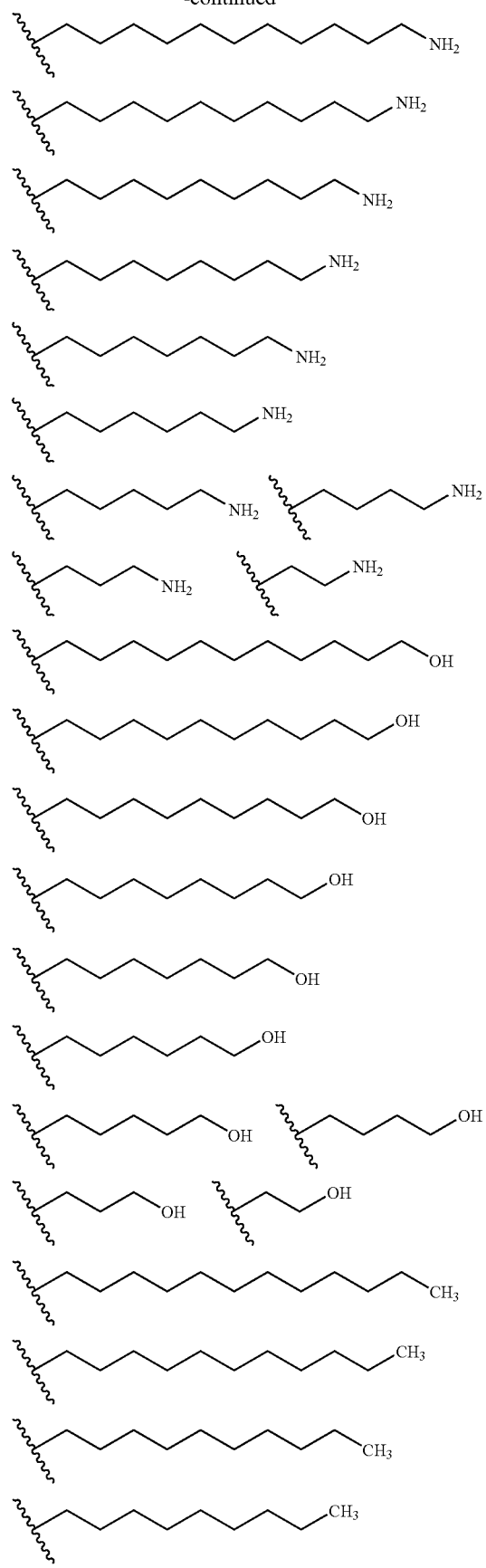

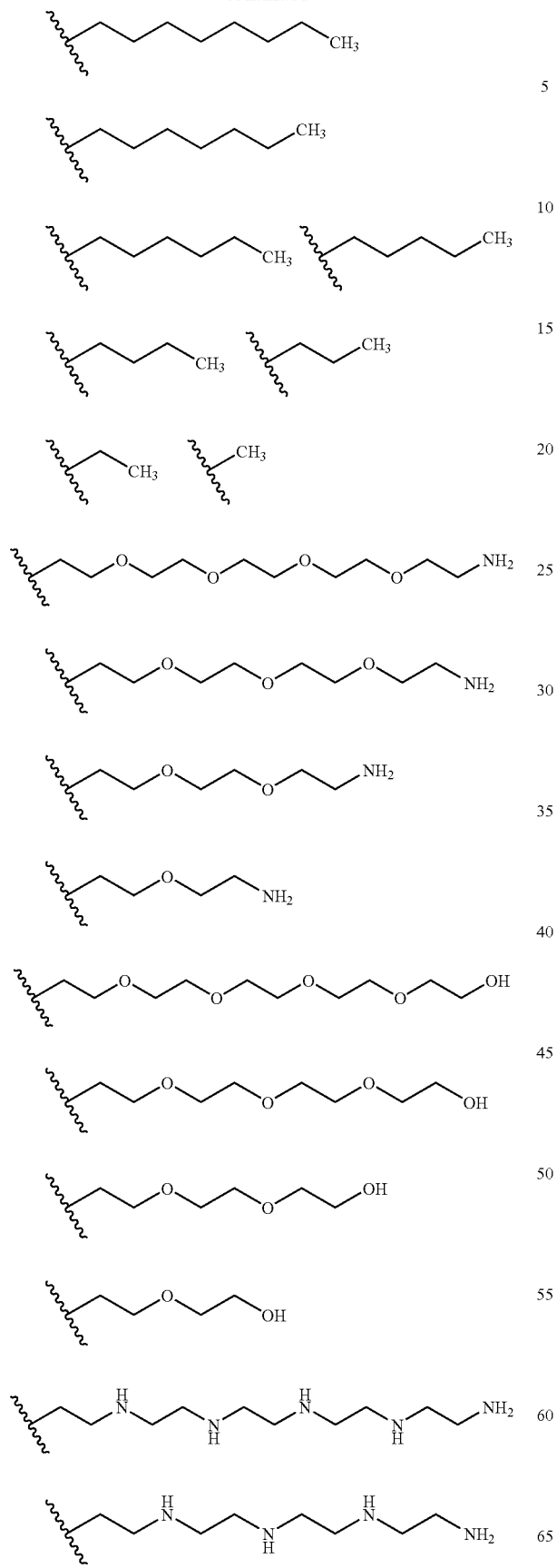
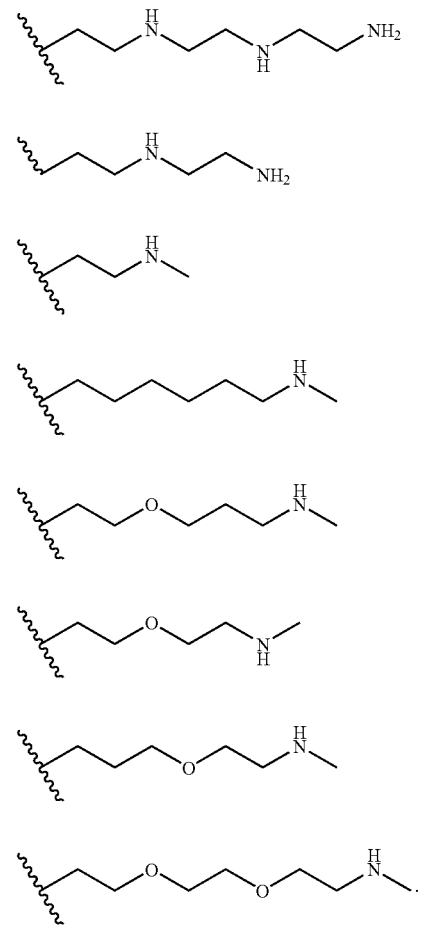
In certain other embodiments, $R_3$ and $R_4$ are selected from the group consisting of:
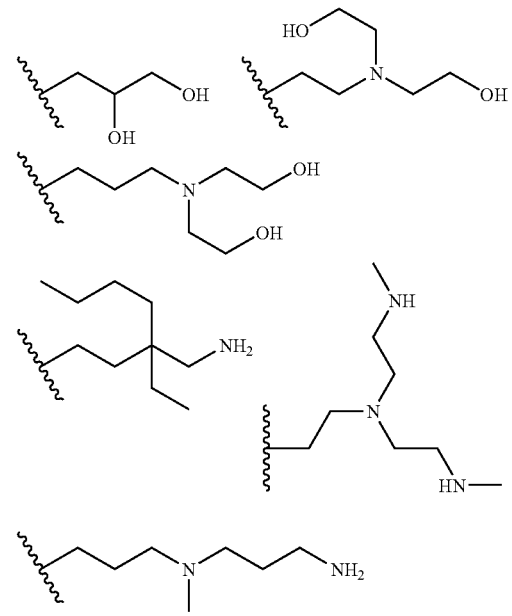

-continued

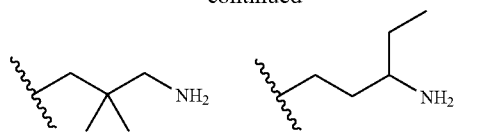

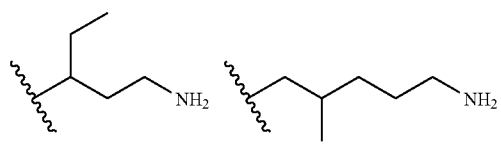

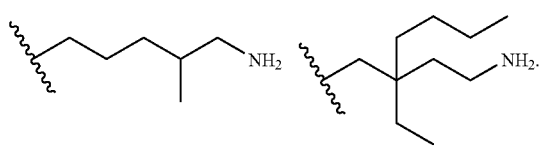

In certain other embodiments, $R_3$ and $R_4$ are selected from the group consisting of:

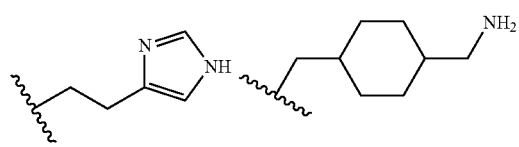

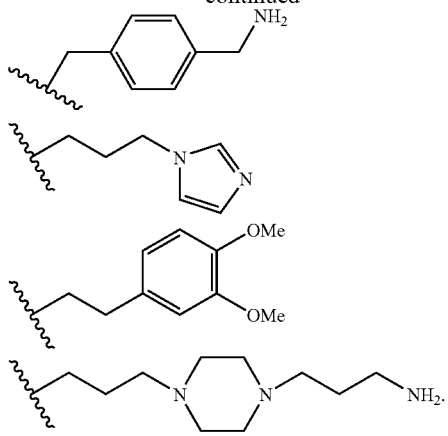

In certain embodiments, X is O. In other embodiments, X is NH. In yet other embodiments, X is $NR_X$. In certain embodiments, X is $NR_X$, wherein $R_X$ is $C_1$-$C_6$ alkyl. In certain particular embodiments, $NR_X$ is NMe. In other embodiments, $NR_X$ is NEt.

In the inventive polymers, n is an integer ranging from 5 to 10,000, more preferably from 10 to 500.

In certain embodiments, the end-modified polymers are of the formulae below wherein bismethyacrylate units have been used to prepare the methacrylate-terminated poly(beta-amino ester) which are subsequently end-modified with a nucleophile:

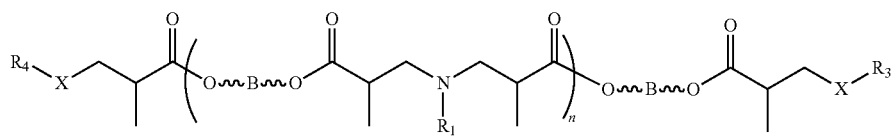

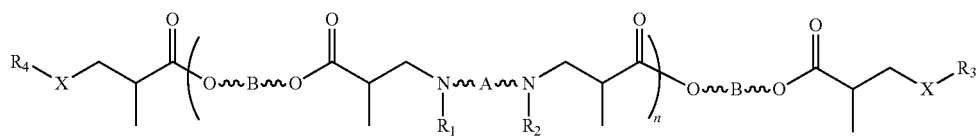

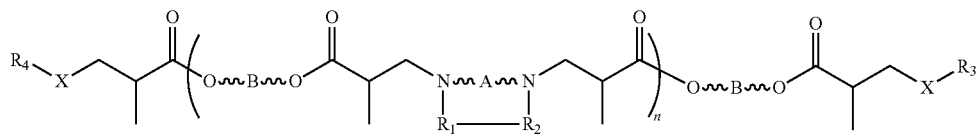

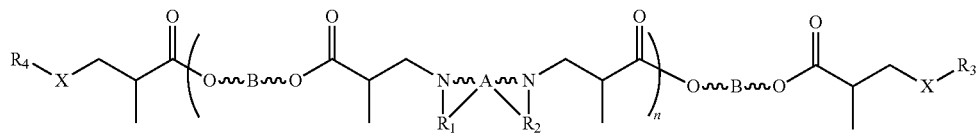

wherein $R_1$, $R_2$, $R_3$, $R_4$, X, A, and B are defined in the genera, classes, subclasses, and species as above.

In another embodiment, the diacrylate unit in the poly(beta-amino ester) is chosen from the following group of diacrylate units (A-PP):

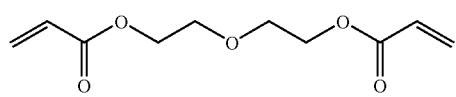 A
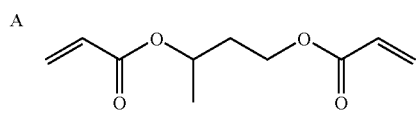 B
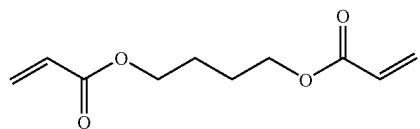 C
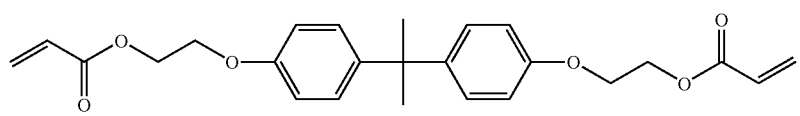 D
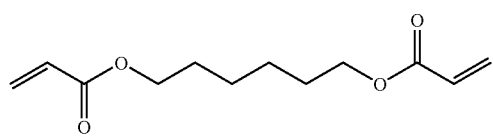 E
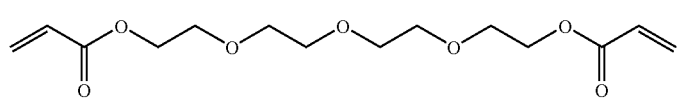 F
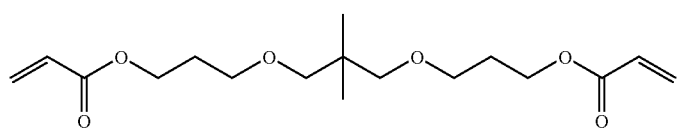 J
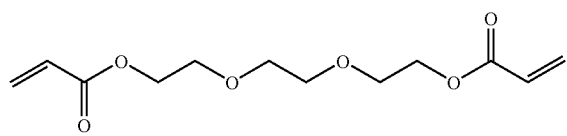 K
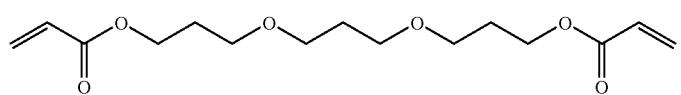 L
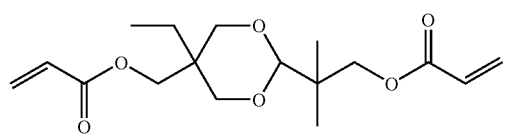 M
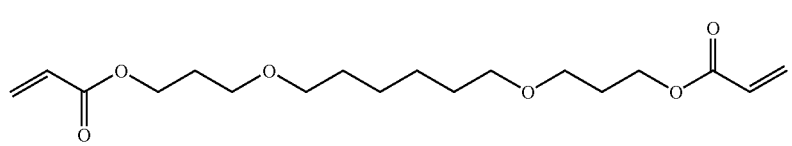 O
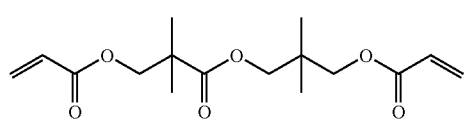 P
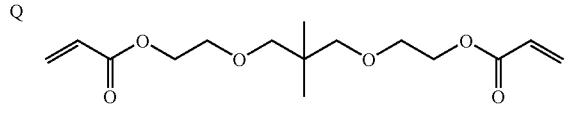 Q, R S
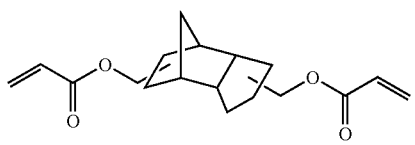
T
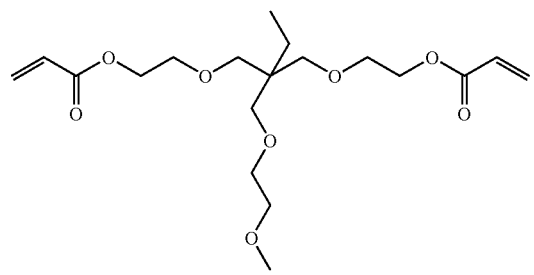
U
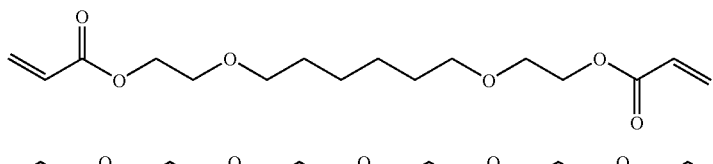
Z
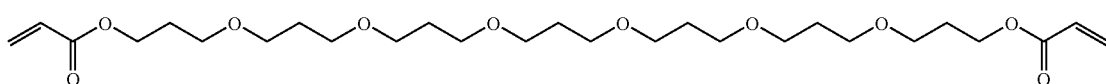
AA
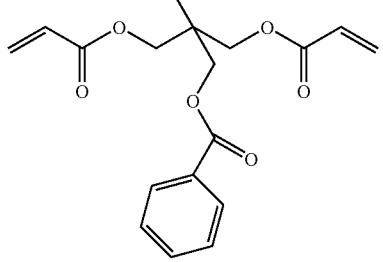
BB
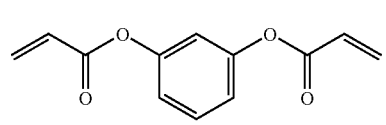
II
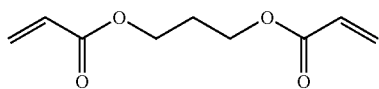
JJ
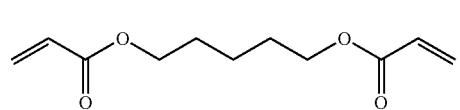
KK
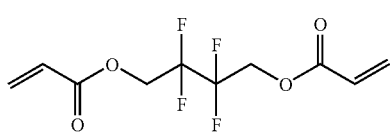
LL
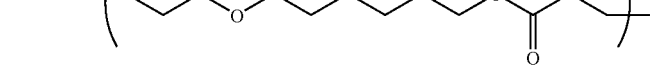
PP
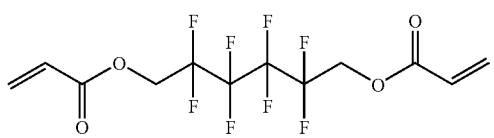
In another embodiment, the diacrylate unit of the polymer is chosen from the following group of diacrylate units (A'-G'):
A'
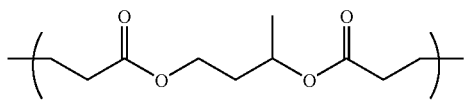
C'
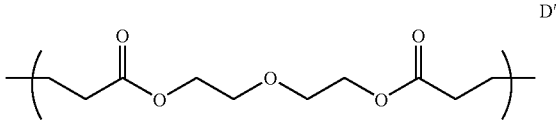
B'
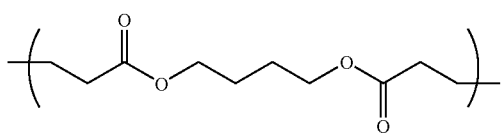
D'

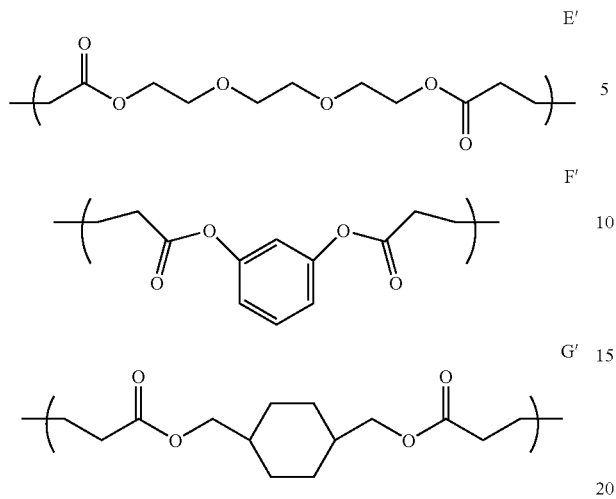

Particularly preferred diacrylate units include A, B', C, C', J, U, AA, PP, and L.

In another embodiment, the amine used in the preparation of the poly(beta-amino ester) is chosen from the following group of amines (1'-20'):

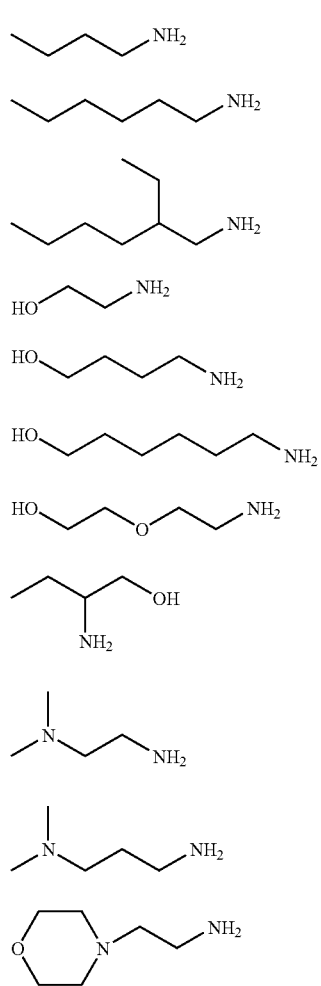

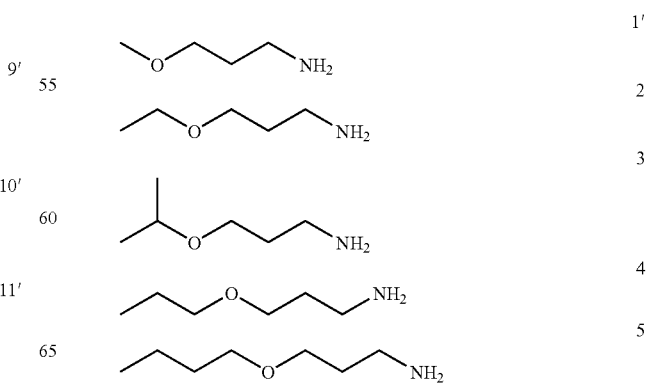

As would be appreciated by one of skill in this art, these amines may also be used to end-modify acrylate-terminated poly(beta-amino esters).

In another embodiment, the amine used in the preparation of the poly(beta-amino ester) is chosen from the following group of amines (1-94):

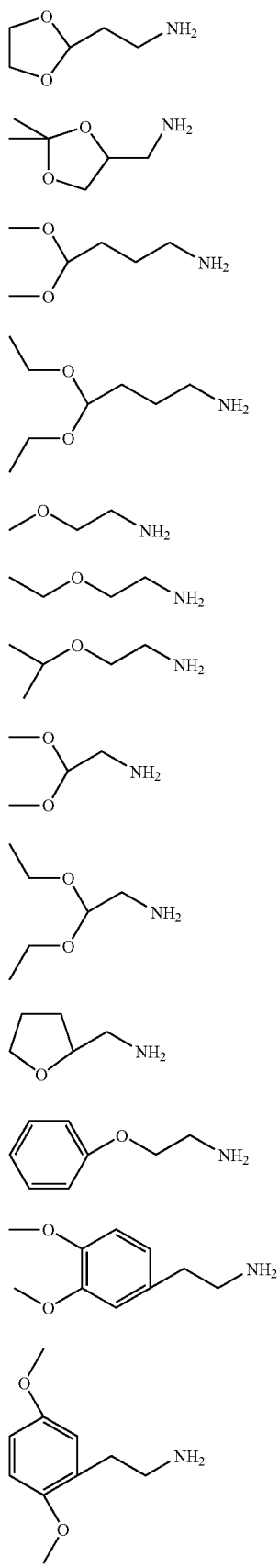
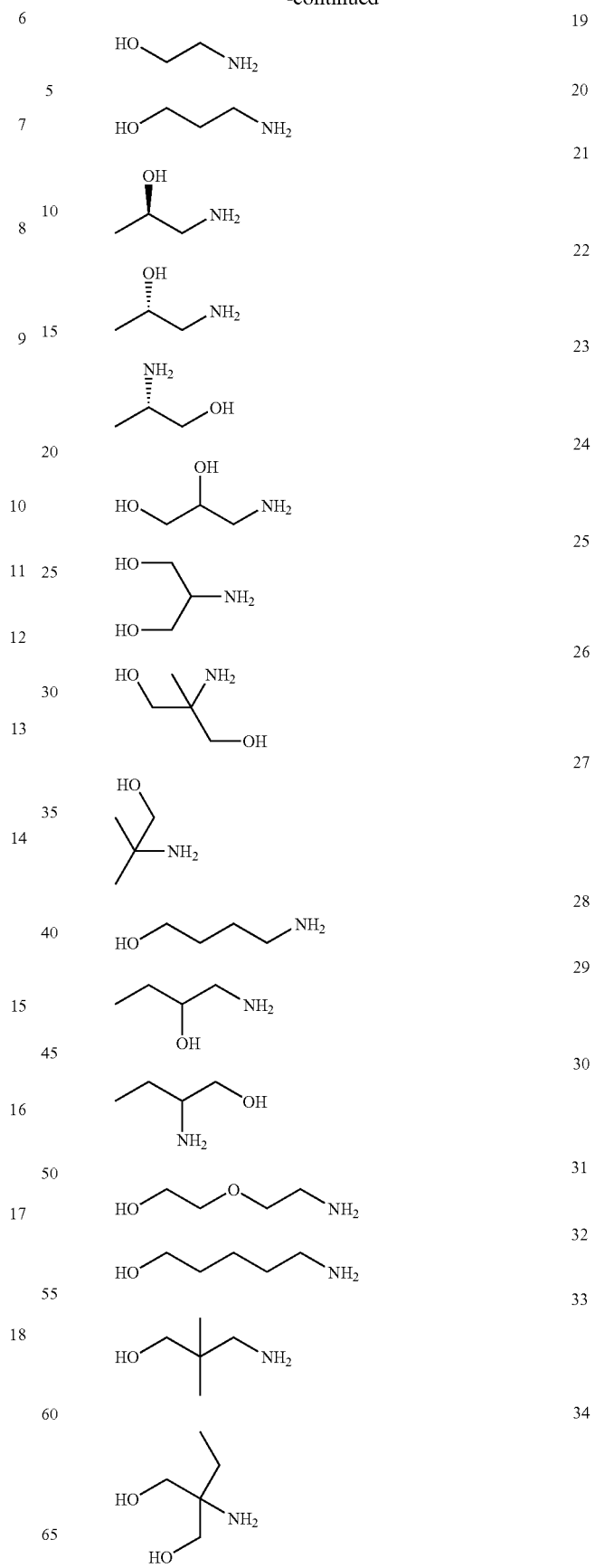

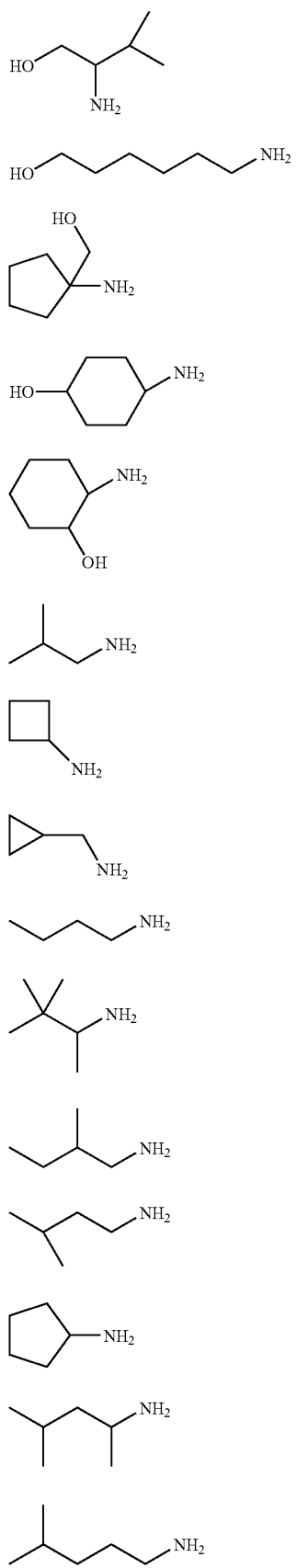
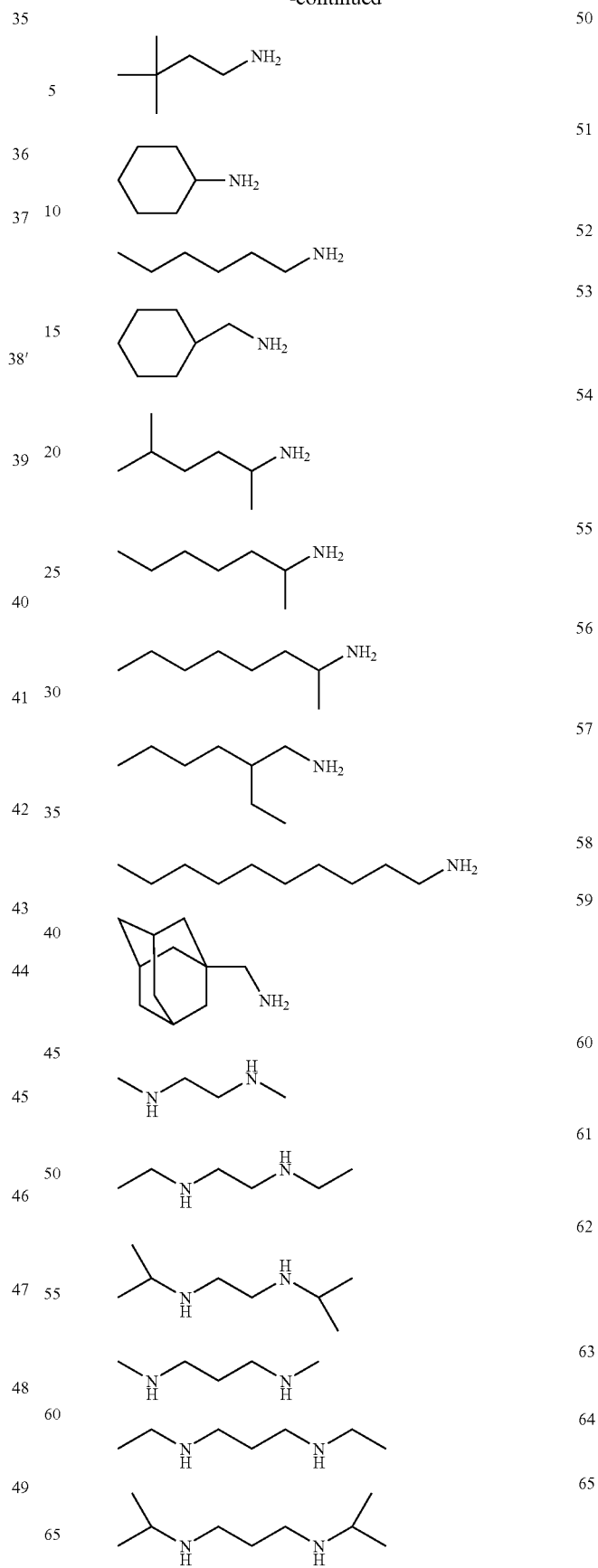

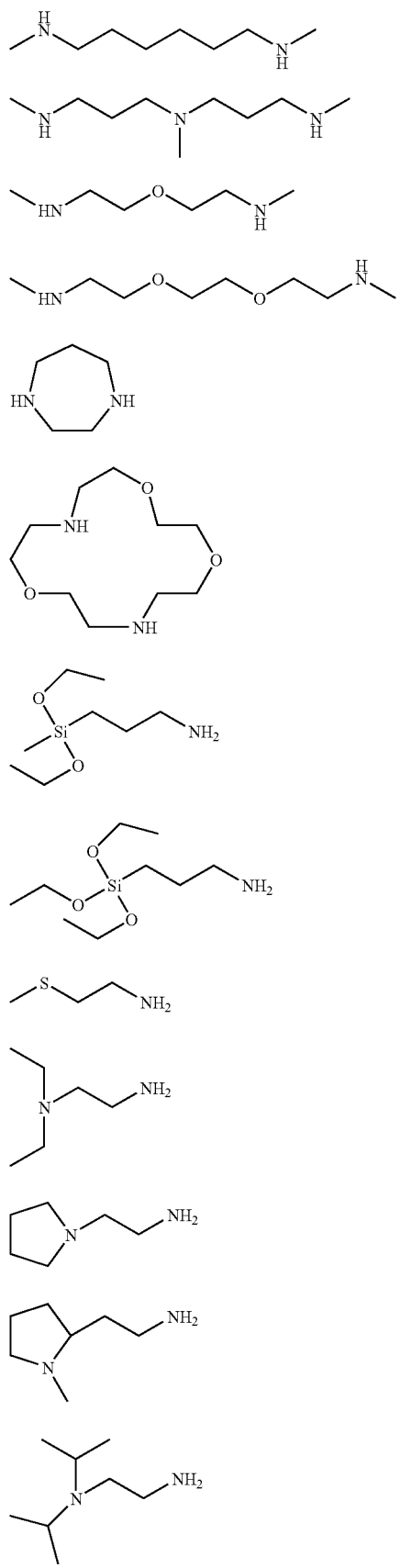
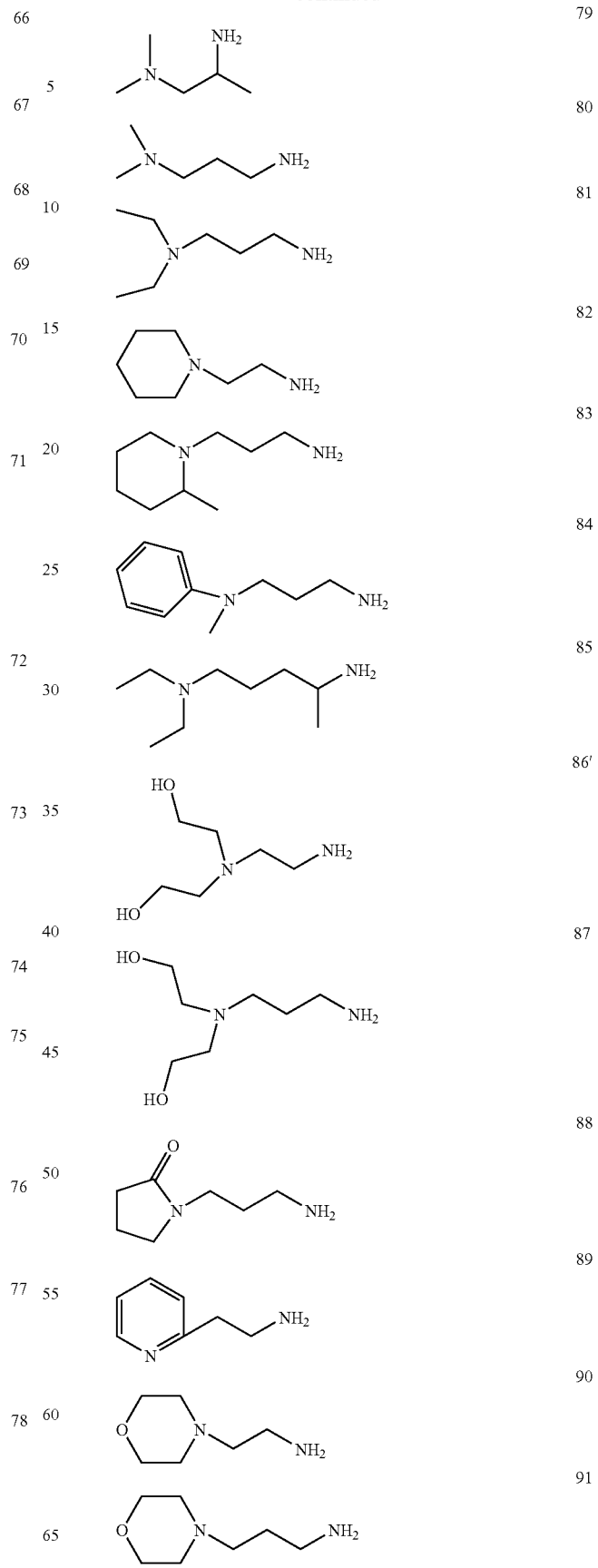

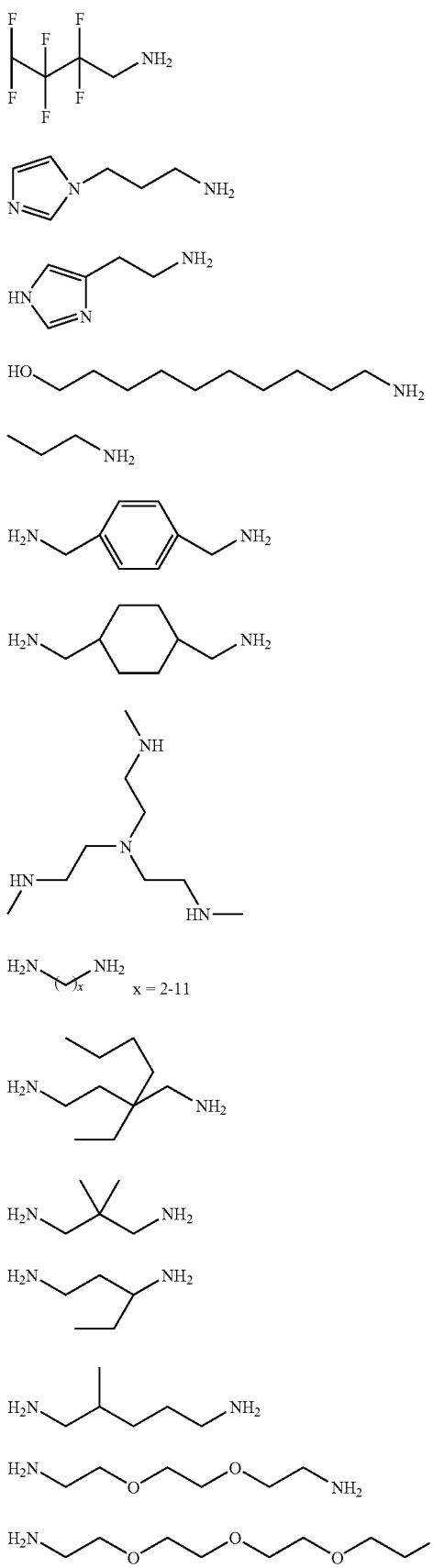
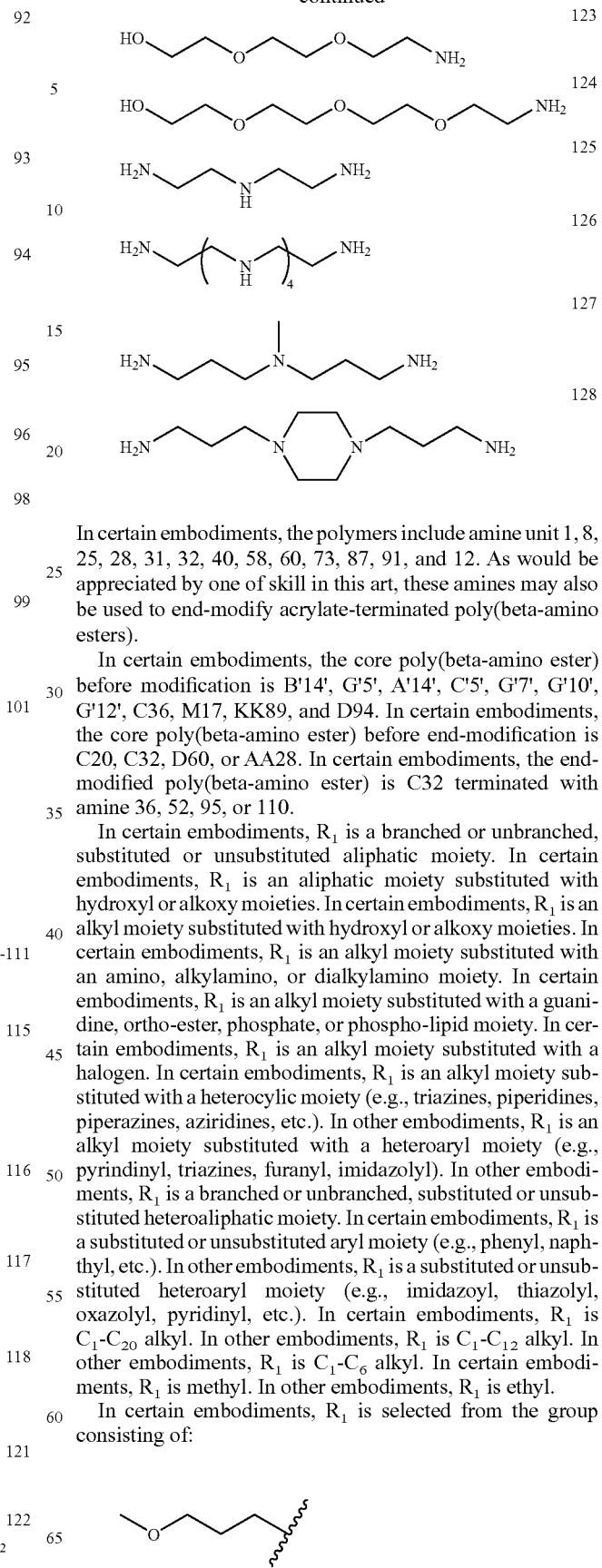

In certain embodiments, the polymers include amine unit 1, 8, 25, 28, 31, 32, 40, 58, 60, 73, 87, 91, and 12. As would be appreciated by one of skill in this art, these amines may also be used to end-modify acrylate-terminated poly(beta-amino esters).

In certain embodiments, the core poly(beta-amino ester) before modification is B'14', G'5', A'14', C'5', G'7', G'10', G'12', C36, M17, KK89, and D94. In certain embodiments, the core poly(beta-amino ester) before end-modification is C20, C32, D60, or AA28. In certain embodiments, the end-modified poly(beta-amino ester) is C32 terminated with amine 36, 52, 95, or 110.

In certain embodiments, $R_1$ is a branched or unbranched, substituted or unsubstituted aliphatic moiety. In certain embodiments, $R_1$ is an aliphatic moiety substituted with hydroxyl or alkoxy moieties. In certain embodiments, $R_1$ is an alkyl moiety substituted with hydroxyl or alkoxy moieties. In certain embodiments, $R_1$ is an alkyl moiety substituted with an amino, alkylamino, or dialkylamino moiety. In certain embodiments, $R_1$ is an alkyl moiety substituted with a guanidine, ortho-ester, phosphate, or phospho-lipid moiety. In certain embodiments, $R_1$ is an alkyl moiety substituted with a halogen. In certain embodiments, $R_1$ is an alkyl moiety substituted with a heterocylic moiety (e.g., triazines, piperidines, piperazines, aziridines, etc.). In other embodiments, $R_1$ is an alkyl moiety substituted with a heteroaryl moiety (e.g., pyrindinyl, triazines, furanyl, imidazolyl). In other embodiments, $R_1$ is a branched or unbranched, substituted or unsubstituted heteroaliphatic moiety. In certain embodiments, $R_1$ is a substituted or unsubstituted aryl moiety (e.g., phenyl, naphthyl, etc.). In other embodiments, $R_1$ is a substituted or unsubstituted heteroaryl moiety (e.g., imidazoyl, thiazolyl, oxazolyl, pyridinyl, etc.). In certain embodiments, $R_1$ is $C_1$-$C_{20}$ alkyl. In other embodiments, $R_1$ is $C_1$-$C_{12}$ alkyl. In other embodiments, $R_1$ is $C_1$-$C_6$ alkyl. In certain embodiments, $R_1$ is methyl. In other embodiments, $R_1$ is ethyl.

In certain embodiments, $R_1$ is selected from the group consisting of:

-continued

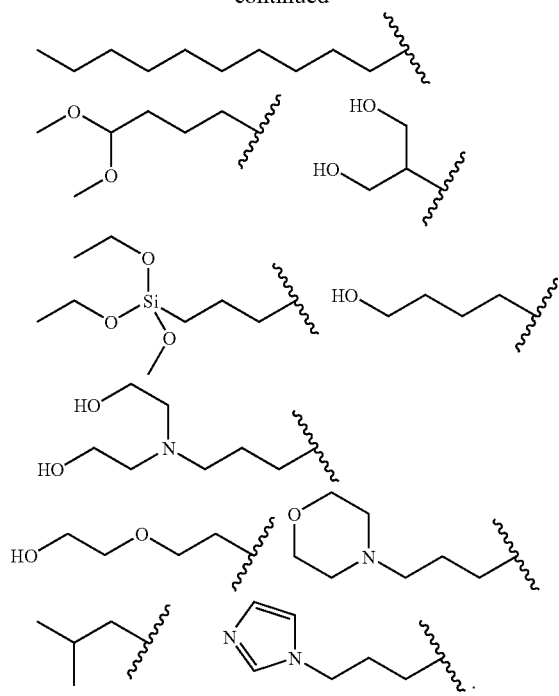

In certain embodiments, $R_2$ is a branched or unbranched, substituted or unsubstituted aliphatic moiety. In certain embodiments, $R_2$ is an aliphatic moiety substituted with hydroxyl or alkoxy moieties. In certain embodiments, $R_2$ is an alkyl moiety substituted with hydroxyl or alkoxy moieties. In certain embodiments, $R_2$ is an alkyl moiety substituted with an amino, alkylamino, or dialkylamino moiety. In certain embodiments, $R_2$ is an alkyl moiety substituted with a guanidine, ortho-ester, phosphate, or phospho-lipid moiety. In certain embodiments, $R_2$ is an alkyl moiety substituted with a halogen. In certain embodiments, $R_2$ is an alkyl moiety substituted with a heterocylic moiety (e.g., triazines, piperidines, piperazines, aziridines, etc.). In other embodiments, $R_2$ is an alkyl moiety substituted with a heteroaryl moiety (e.g., pyrindinyl, triazines, furanyl, imidazolyl). In other embodiments, $R_2$ is a branched or unbranched, substituted or unsubstituted heteroaliphatic moiety. In certain embodiments, $R_2$ is a substituted or unsubstituted aryl moiety (e.g., phenyl, naphthyl, etc.). In other embodiments, $R_2$ is a substituted or unsubstituted heteroaryl moiety (e.g., pyridinyl, triazines, imidazoyl, thiazolyl, oxazolyl, pyridinyl, etc.). In certain embodiments, $R_2$ is $C_1$-$C_{20}$ alkyl. In other embodiments, $R_2$ is $C_1$-$C_{12}$ alkyl. In other embodiments, $R_2$ is $C_1$-$C_6$ alkyl. In certain embodiments, $R_2$ is methyl. In other embodiments, $R_2$ is ethyl.

In certain embodiments, one or both of the linkers A and B are linkers containing only carbon, oxygen, and hydrogen atoms. In certain embodiments, one or both of the linkers A and B are linkers containing only carbon and hydrogen atoms. In certain embodiments, one or both of the linkers A and B are linkers containing only carbon and halogen atoms. In one embodiment, one or both of the linkers A and B are polyethylene linkers. In another particularly preferred embodiment, one or both of the linkers A and B are polyethylene glycol linkers. Other biocompatible, biodegradable linkers may be used as one or both of the linkers A and B.

In certain embodiments, A is

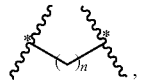

wherein n is an integer between 1 and 20, inclusive. In certain embodiments, n is an integer between 1 and 15, inclusive. In other embodiments, n is an integer between 1 and 10, inclusive. In yet other embodiments, n is an integer between 1 and 6, inclusive. In certain embodiments, n is 2. In other embodiments, n is 3. In yet other embodiments, n is 4. In still other embodiments, n is 6.

In certain embodiments, A is

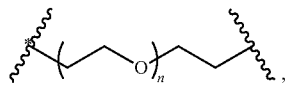

wherein n is an integer between 1 and 20, inclusive. In certain embodiments, n is an integer between 1 and 15, inclusive. In other embodiments, n is an integer between 1 and 10, inclusive. In yet other embodiments, n is an integer between 1 and 6, inclusive. In certain embodiments, n is 1. In certain embodiments, n is 2. In other embodiments, n is 3. In yet other embodiments, n is 4. In still other embodiments, n is 6.

In certain embodiments, A is

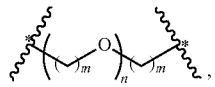

wherein n is an integer between 1 and 20, inclusive; and m is an integer between 1 and 6, inclusive. In certain embodiments, n is an integer between 1 and 15, inclusive. In other embodiments, n is an integer between 1 and 10, inclusive. In yet other embodiments, n is an integer between 1 and 6, inclusive. In certain embodiments, n is 1. In certain embodiments, n is 2. In other embodiments, n is 3. In yet other embodiments, n is 4. In still other embodiments, n is 6. In certain embodiments, m is 1. In other embodiments, m is 2. In yet other embodiments, m is 3. In still other embodiments, m is 4.

In certain embodiments, B is

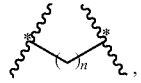

wherein n is an integer between 1 and 20, inclusive. In certain embodiments, n is an integer between 1 and 15, inclusive. In other embodiments, n is an integer between 1 and 10, inclusive. In yet other embodiments, n is an integer between 1 and 6, inclusive. In certain embodiments, n is 2. In other embodiments, n is 3. In yet other embodiments, n is 4. In still other embodiments, n is 6.

In certain embodiments, B is

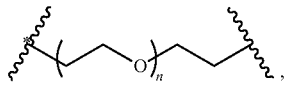

wherein n is an integer between 1 and 20, inclusive. In certain embodiments, n is an integer between 1 and 15, inclusive. In other embodiments, n is an integer between 1 and 10, inclusive. In yet other embodiments, n is an integer between 1 and 6, inclusive. In certain embodiments, n is 1. In certain embodiments, n is 2. In other embodiments, n is 3. In yet other embodiments, n is 4. In still other embodiments, n is 6.

In certain embodiments, B is

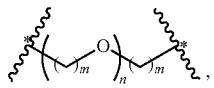

wherein n is an integer between 1 and 20, inclusive; and m is an integer between 1 and 6, inclusive. In certain embodiments, n is an integer between 1 and 15, inclusive. In other embodiments, n is an integer between 1 and 10, inclusive. In yet other embodiments, n is an integer between 1 and 6, inclusive. In certain embodiments, n is 1. In certain embodiments, n is 2. In other embodiments, n is 3. In yet other embodiments, n is 4. In still other embodiments, n is 6. In certain embodiments, m is 1. In other embodiments, m is 2. In yet other embodiments, m is 3. In still other embodiments, m is 4.

In certain embodiments, B is selected from the group consisting of:

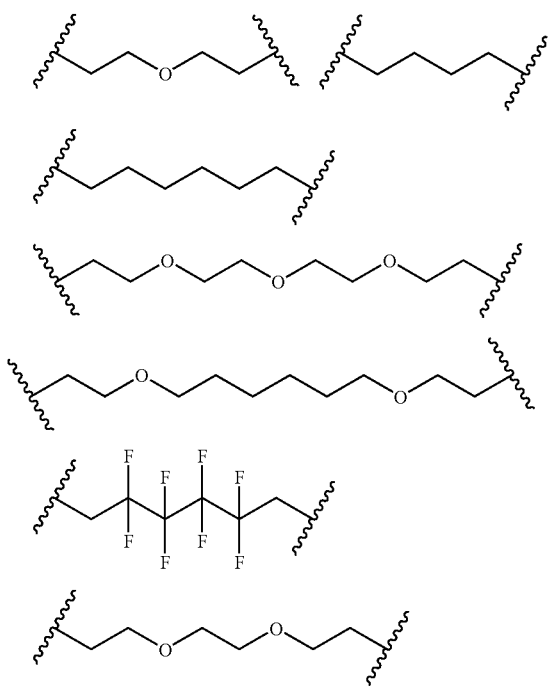

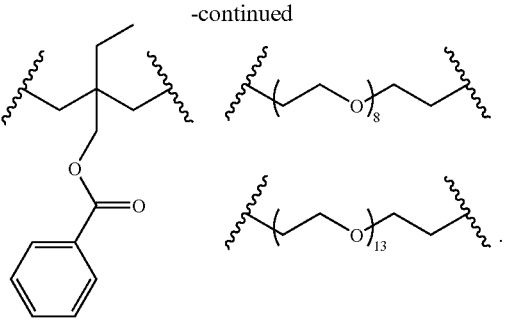

In certain embodiments, the average molecular weight of the polymers of the present invention range from 1,000 g/mol to 50,000 g/mol, preferably from 2,000 g/mol to 40,000 g/mol, more preferably from 5,000 g/mol to 20,000 g/mol, and even more preferably from 10,000 g/mol to 17,000 g/mol. Since the polymers of the present invention are prepared by a step polymerization, a broad, statistical distribution of chain lengths is typically obtained. In certain embodiments, the distribution of molecular weights in a polymer sample is narrowed by purification and isolation steps known in the art. In other embodiments, the polymer mixture may be a blend of polymers of different molecular weights.

In another embodiment, the polymer of the present invention is a co-polymer wherein one of the repeating units is a poly(β-amino ester) of the present invention. In another embodiment, the polymer of the present invention is a co-polymer wherein one of the repeating units is a poly(β-amino amide). Other repeating units to be used in the co-polymer include, but are not limited to, polyethylene, poly(glycolide-co-lactide) (PLGA), polyglycolic acid, polymethacrylate, etc. In certain embodiments, at least one end of the polymer is a poly(beta-amino ester), poly(beta-amino amide, or other inventive polymer which is end-modified by the addition of a nucleophile (e.g., a amine) to a terminal acrylate unit. In certain other embodiments, at least one end of the polymer is a poly(beta-amino ester), poly(beta-amino amide, or other inventive polymer which is end-modified by the addition of an electrophile to a terminal amine moiety.

Synthesis of End-Modified Poly(Beta-Amino Esters)

The inventive end-modified polymers may be prepared by any method known in the art. The polymers used as starting materials to prepare end-modified poly(beta-amino esters) or poly(beta-amino amides) are prepared from commercially available starting materials or are obtained from other sources. The synthesis of poly(beta-amino esters) is described in U.S. patent applications, U.S. Ser. No. 11/099,886, filed Apr. 6, 2005; U.S. Ser. No. 10/446,444, filed May 28, 2003; U.S. Ser. No. 09/969,431, filed Oct. 2, 2001; U.S. Ser. No. 60/305,337, filed Jul. 13, 2001; and U.S. Ser. No. 60/239,330, filed Oct. 10, 2000; each of which is incorporated herein by reference.

In summary, poly(beta-amino esters) are prepared via the conjugate addition of a diamine or primary amine to bis (acrylate esters). This reaction scheme is shown below:

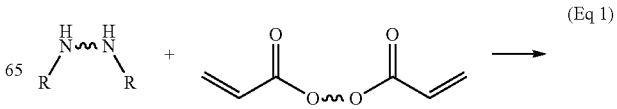

(Eq 1)

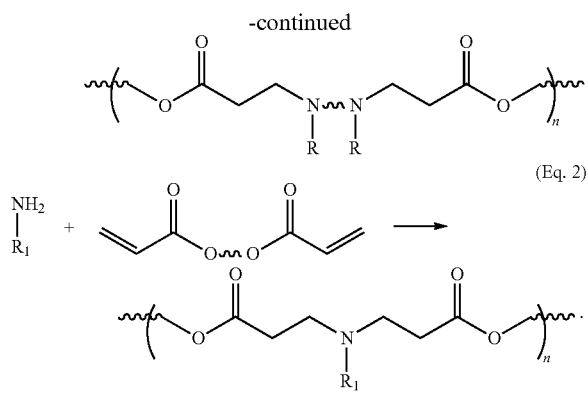

(Eq. 2)

The use of primary amines rather than diamines allows for a much wider variety of commercially available starting materials.

In preparing the polymers of the present invention, the monomers in the reaction mixture may be combined in different ratio to effect molecular weight, yield, end-termination, etc. of the resulting polymer. As would be appreciated by one of skill in this art, the molecular weight of the synthesized polymer may be determined by the reaction conditions (e.g., temperature, starting materials, concentration, order of addition, solvent, etc.) used in the synthesis (Odian *Principles of polymerization* 3rd Ed., New York: John Wiley & Sons, 1991; Stevens *Polymer Chemistry: An Introduction* 2nd Ed., New York: Oxford University Press, 1990; each of which is incorporated herein by reference). In certain embodiments, the ratio of amine monomers to diacrylate monomers is less than 1.0. In certain embodiments, the ratio of amine monomer to diacrylate monomer is approximately 0.95, 0.9, 0.85, 0.8, 0.75, 0.7, 0.65, 0.6, 0.55, or 0.5. For example, combining the monomers at a ratio of less than 1 typically results in acrylate-terminated chains, which are subsequently end-modified. Combining the monomers at a ratio of greater than 1 typically results in amine-terminated chains, which are subsequently end-modified. In certain embodiments, the ratio of amine monomers to diacrylate monomers is greater than 1.0. In certain embodiments, the ratio of amine monomer to diacrylate monomer is approximately 1.05, 1.1, 1.15, 1.2, 1.25, 1.3, 1.35, 1.4, 1.45, 1.5, 2.0, 3.0, 4.0, or 5.0.

An acrylate-terminated poly(beta-amino ester) or other polymer, optionally purified, is reacted with a nucleophile under suitable conditions to allow the nucleophile to add to the terminal acrylate units. In certain embodiments, an excess of the nucleophile is used in the reaction mixture. In certain embodiments, the nucleophile used in the reaction is an amine. In certain embodiments, the nucleophile used in the reaction is an aniline. In other embodiments, the nucleophile is a thiol. In yet other embodiments, the nucleophile is an alcohol. In certain embodiments, the nucleophile is a phenol. Typically, the poly(beta-amino ester) is mixed with an excess of the nucleophile to be used to modify the terminal acrylate units.

An amine-terminated poly(beta-amino ester) or other polymer, optionally purified, is reacted with an electrophile under suitable conditions to allow the electrophile to react with the terminal amino units. In certain embodiments, an excess of the electrophile is used in the reaction mixture. In certain embodiments, the electrophile used in the reaction is an acrylate. In certain embodiments, the electrophile used in the reaction is an acrylamide. In other embodiments, the electrophile is an acyl moiety. In other embodiments, the electrophile is an aliphatic halide (e.g., an alkyl halide). Typically, the starting polymer is mixed with an excess of the electrophile to be used to modify the terminal amine units.

The reaction may be run in an organic solvent or neat. Exemplary organic solvents include acetone, ethers, benzene, THF, toluene, hexanes, DMSO, DMF, etc. Non-nucleophilic solvents are preferred. The reaction mixture may then be heated to effect the addition of the nucleophile to the terminal units of the polymer. In certain embodiments, the reaction mixture is heated to between 30 and 150° C. The reaction is allowed to proceed from 1 hours to 48 hours; preferably, approximately 3 hours to 16 hours. As would be appreciated by one of skill in this art, the reaction conditions may vary depending on the polymer being modified and the nucleophile being used. The progress of the reaction may be optionally monitored by TLC, HPLC, or other analytical techniques commonly used in the art.

The resulting end-modified polymer may be purified by any technique known in the art including, but not limited to, precipitation, crystallization, chromatography, etc. In a particular embodiment, the polymer is purified through repeated precipitations in organic solvent (e.g., diethyl ether, hexane, etc.). In another embodiment, the polymer is isolated as a salt (e.g., hydrochloride, hydrobromide, hydroiodided, phosphate, acetate, fatty acid, etc.). The resulting polymer may also be used as is without further purification and isolation.

The resulting end-modified polymer may be subsequently modified by reacting the polymer with another electrophile or nucleophile. For example, a nucleophile-terminated polymer may be subsequently reacted with an electrophile. Or an electrophile-terminated polymer may be subsequently reacted with a nucleophile. The process of serially end-modifying a polymer may be carried out any number of times (e.g., at least 2, 3, 4, 5, 6, 7, 8, 9, 10, or more times. The desired polymer may be purified at the end of each step or at the end of the process. In certain embodiments, the individual reaction are optimized to prepare the desired polymer at greater than 80%, 90%, 95%, 98%, or 99% yield.

In one embodiment, a library of different end-modified poly(beta-amino esters), poly(beta-amino amides, or other polymers is prepared in parallel. The synthesis of a library of end-modified polymers may be carried out using any of the teachings known in the art or described herein regarding the synthesis of end-modified polymers. In one embodiment, a different amine and/or bis(acrylate ester) at a particular amine-to-acrylate ratio is added to each vial in a set of vials used to prepare the library or to each well in a multi-well plate (e.g., 96-well plate). In certain embodiments, the library contains the same poly(beta-amino ester) core with different end modifications. Such libraries are particularly useful in determining the effect of end-modification. In other embodiments, the library contains different poly(beta-amino esters) with the same end modification. In certain embodiments, over 100 different end-modified poly(beta-amino esters) are prepared in parallel. In certain embodiments, over 500 different end-modified poly(beta-amino esters) are prepared in parallel. In certain embodiments, over 1000 different end-modified poly(beta-amino esters) are prepared in parallel. In other embodiments, over 2000 different end-modified poly(beta-amino esters) are prepared in parallel. In still other embodiments, over 3000 different end-modified poly(beta-amino esters) are prepared in parallel. The end-modified poly(beta-amino esters) of the invention may be screened or used after synthesis without further precipitation, purification, or isolation of the polymer. In certain embodiments, the end-modified poly(beta-amino esters) are synthesized and assayed using semi-automated techniques and/or robotic fluid handling systems.

Uses

The inventive end-modified poly(beta-amino esters), poly (beta-amino amides), or other polymers may be used anywhere a polymer is useful. The use of the end-modified polymers will depend on the physical and chemical properties of the material. Chemical properties include pKa, degradation time, ionizability, hydrophobicity, hydrophilicity, reactivity, etc.

The end-modified polymers are particularly useful in the drug delivery arts. For example, the material may be used in forming nanoparticles, microparticles, macroparticles, capsules, coatings, or larger depots of a therapeutic agent, diagnostic agent, or prophylatic agent. In certain embodiments, the agents to be delivered is combined with an inventive polymer, and a therapeutically effective amount of the combination is administered to a subject (e.g., human). Any agent may be delivered using the inventive materials including small molecules, contrast agents, peptides, proteins, polynucleotides, DNA, RNA, RNAi, siRNA, mRNA, tRNA, microRNA, ssDNA, dsDNA, ssRNA, shRNA, metals, organometallic compounds, vitamins, minerals, etc. The end-modified poly(beta-amino esters) or poly(beta-amino amides end modified with an amine are particularly useful in delivering polynucleotides. The drug delivery device may provide immediate release of its payload, or it may provide extended or timed-release of the payload.

In certain embodiments, the end-modified polymer is used in tissue engineering. For example, the material may be used in bone, cartilage, liver, pancreas, and muscle replacement. In certain embodiments, the cross-linked material may be used as a bone replacement. In certain embodiments, the material includes osteoblast or other bone-forming cells, and as the material is resorbed by the body, bone is formed at the site. In certain embodiments, the material is used in cartilage replacement and may optionally include cells that produce cartilage or growth factors that induce the growth of cartilage. The inventive materials may also be used to deliver other types of cells. The cells may be genetically engineered cells (e.g., they may have been altered to produce a particular protein, peptide, or polynucleotide), or the cells may be wild type cells. The cells may be stem cells, pluripotent cells, or fully differentiated cells. In certain embodiments, the cells are mammalian cells. In other particular embodiments, the cells are human cells. In certain embodiments, the cells are derived from the subject (i.e., the cells are autologous). In tissue engineering uses, the end-modified polymer preferably has a degradation profile that does not interfere with the growth of the cells. These combinations may be used in any type of surgery including orthopedic surgery, reconstructive surgery, plastic surgery, etc. The material may include other materials such as nutrients, growth factors, other polymers, materials for cell attachment, etc.

The inventive end-modified polymers also have non-medical uses. In certain embodiments, the inventive end-modified polymer is used in preparing a plastic products. These products typically have the advantage of being biodegradable. The materials may also be used as coatings, for example, coatings on papers, coatings on rock, coatings on tile, coatings on wood, coatings on flooring, coatings on metal, coatings over paint, etc. In certain embodiments, the coating is a UV protective coating. In other embodiments, the inventive materials are used in printing. The materials may be used in inks. In still other embodiments, the material is used as an adhesive.

Kits

The invention also provides kits for use in preparing the inventive end-modified poly(beta-amino esters) or other polymers. The kit may include any or all of the following: amines, diacrylates, poly(beta-amino esters), poly(beta-amino amides), polymers, end-modifying agents, nucleophiles, electrophiles, acrylates, acrylamides, vials, solvent, buffers, multi-well plates, salts, polynucleotides, proteins, and instructions. The instructions include ways of preparing the inventive end-modified polymers with various properties. In certain embodiments, the kit is tailored for preparation of end-modified polymers with a desired property or for a desired use. In certain embodiments, the kit includes all the items necessary to prepare one or more end-modified polymers.

These and other aspects of the present invention will be further appreciated upon consideration of the following Examples, which are intended to illustrate certain particular embodiments of the invention but are not intended to limit its scope, as defined by the claims.

EXAMPLES

Example 1

End-Modified Poly(Beta-Amino Esters) for Gene Delivery

Introduction

Incorporation of new genetic elements into cells is a promising strategy for the treatment of many inherited and acquired genetic disorders. In order for gene-based therapeutics to be clinically applicable, a safe and efficient delivery system for DNA needs to be developed. Modified viruses are the most heavily researched agents but still suffer from many problems that include a limited carrying capacity, the potential for insertional mutagenesis, and clearance by the immune system. Various cationic polymers have been developed as an alternative since many can condense DNA and mediate cellular uptake. An additional benefit of synthetic polycations is the potential to alter the structure for optimal gene delivery while minimizing the cytotoxic effects.

The most common polycations used for gene delivery are poly-L-lysine (PLL) and polyethylenimine (PEI). High molecular weight derivatives of both polymers have been shown to self-assemble with plasmid DNA to form nanoparticles capable of transfecting a variety of cell types. Furthermore, functionalization of these polymers with PEG chains and targeting ligands has allowed for cell specific delivery, which is particularly important for cancer gene therapies. Despite their widespread use, both PLL and PEI have significant disadvantages that may ultimately limit their clinical utility. In particular, both polymers are known to be very cytotoxic and have relatively low transfection efficiencies compared to viruses, especially in non-dividing cells.

Poly($\beta$-amino ester)s are an alternative class of cationic polymers that have been recently developed and explored as gene delivery vectors. These polymers are degradable by hydrolysis of backbone ester bonds and contain tertiary amines to facilitate DNA binding. They are synthesized by a simple Michael addition reaction between bi-functional amines and diacrylates. The polymer molecular weight and chain end groups can be easily controlled by adjusting the amine:diacrylate monomer ratio. This potential variability in monomer ratio, along with the commercial availability of many amine and diacrylate monomers, has allowed for the generation of large, structurally diverse libraries of poly($\beta$-amino ester)s. High throughput transfection screens have identified many polymers that are capable of transfecting cells with much higher efficiencies than PEI, while also demonstrating less toxicity both in vitro and in vivo. The polymer libraries have also been useful to elucidate structure-function relationships. These studies have shown that high molecular weight, amine-terminated poly(β-amino ester)s with hydroxyl-functionalized side chains are highly efficient polymers for gene delivery. The most effective polymer discovered, C32+, has also been used in vivo for the gene-based treatment of prostate cancer.

The continued development of poly(β-amino ester)s for gene therapy and other biomedical applications requires an effective method to chemically modify these materials. As with other polycations, it is necessary to incorporate additional levels of functionality such as serum stability and cell targeting to improve the gene delivery properties of these polymers. The ideal approach to poly(β-amino ester) modification would involve a chemistry that is simple, versatile, and adaptable to a high throughput format. It is important to generate many polymeric derivatives since any modification has a non-trivial affect on gene delivery. Previous studies have shown that even single carbon or functional group differences between polymer repeat units can drastically affect their transfection efficiencies.

As one potential method for polymer functionalization, we present here a high throughput approach to synthesize end-modified poly(β-amino ester)s and explore the effects of end group structure on polymer gene delivery properties. End-modified polymers were synthesized following a two step procedure in which an acrylate-terminated base polymer is first prepared by polymerization using excess diacrylate over amine monomer. In a second stage, the base polymer was reacted with various amine reagents to generate amine-capped polymer chains. Following this approach, we have generated a library of end-modified C32 polymers and demonstrate that the terminal amine has a large effect on C32 transfection. Similar to polymer repeat units, end segments differing in a single additional carbon or functional group can drastically affect the polymer delivery properties. In addition, the terminal amine structure has a large influence on cytotoxicity, physical properties, and cellular uptake of polymer-DNA complexes. We also show that significant improvements in transfection efficiency can be made by proper end-modification of other base polymers that were previously found to be less effective than C32+. These results indicate that end-modification is a useful strategy to functionalize poly(β-amino ester)s and improve their gene delivery performance.

Results and Discussion

Polymer Synthesis. We developed a two-step approach to synthesize end-modified poly(β-amino ester)s. The reactions are illustrated in FIGS. 1A and 1B for the generation of end-modified C32 polymers. In the first step, acrylate-terminated polymer was prepared by mixing acrylate and amine monomers in a 1.2:1.0 molar ratio, as shown previously (FIG. 1A). This ratio was selected since C32+ and many other top performing, amine-terminated polymers are made at the inverse ratio using excess amine. We hypothesized then that the exact opposite ratio may be optimal so that the relative number of interior to terminal units is approximately preserved, with the end-capping step causing a very small change to this balance. Since the terminal amine is very small relative to the polymer chain, the diacrylate:amine ratio selected also controls the final molecular weight. For many poly(β-amino ester)s, molecular weights greater than 10 kDa are usually most effective and can be achieved using a 1.2:1.0 molar monomer ratio. For the C32-acrylate polymer (C32-Ac), the weight-average molecular weight is approximately 8,800 Da, relative to polystyrene standards, with a 1.9 polydispersity index. Assuming that each amine-acrylate combination designates a unit, either a repeat unit in the backbone or terminal unit, then 2 of the 16 units (12.5%) in an average length chain are terminal units. This implies that the ends make a non-negligible contribution to the size and functionality of the polymer.

In the second step, acrylate-terminated polymers are reacted with various amine molecules to generate amine-capped polymer chains. In this way, the chain ends contain amine functionalities different than those present in the interior of the polymer. The capping reaction is shown in FIG. 1B for an arbitrary primary amine molecule, which results in an amine-capped polymer containing secondary amines at the chain end points. Secondary amine molecules can also be used but result in tertiary amine groups at the polymer ends. The 41 different amine molecules used for this secondary capping step are shown in FIG. 1C. These compounds were selected on the basis of their DMSO solubility and biocompatibility. In addition, many of these molecules have proven useful in the synthesis of poly(β-amino ester)s with high transfection efficiencies.

The end-capping reaction occurs via an amine-acrylate Michael addition, identical to that used in the polymerization. Since the acrylate functionality has no detectable reactivity towards hydroxyls, ethers, tertiary amines, amides, aromatics, and some types of heterocycles, all of these functionalities can be incorporated at the chain ends using the appropriate amine reagents. The reaction is carried out by mixing a concentrated polymer solution with an excess of amine in DMSO at room temperature. The conditions have been optimized with excess amine to fully end-cap all chains without causing any detectable crosslinking or aminolysis of backbone ester bonds, as determined by $^1$H NMR and GPC analysis. In addition, end-modified polymers can be directly tested for transfection efficiency without prior purification since the DMSO and excess amine were determined to be non-toxic (data not shown). Therefore, this chemistry permits many polymers with structurally diverse end functionalities to be synthesized and screened in parallel. We show here that such a synthetic method is useful to assess end amine structure-function relationships and improve the gene delivery properties of poly(β-amino ester)s.

In much of the analysis presented here, we use C32 as a base polymer to examine the effects of the end amine structure on polymer transfection and also explore structure-function relationships. This polymer was identified from previous studies to be the most efficient poly(β-amino ester) for gene delivery. In principle, other base polymers, diacrylate:amine ratios, and amine capping agents may be used and could generate more effective polymers for gene delivery. To demonstrate this potential, two additional amine-capped poly(b-amino ester)s, D60 and C20, were prepared and assayed for DNA transfection. The structures of these acrylate-terminated base polymers are shown in FIG. 1D. Also shown is the structure of acrylate-terminated AA28 polymer, which was also capped with several amines and used to demonstrate the ability to deliver siRNA for gene silencing.

COS-7 Transfections. The DNA delivery efficiency of end-modified poly(β-amino ester)s was evaluated using a high throughput assay. Concentrated polymer solutions in DMSO were diluted in sodium acetate buffer and complexed with plasmid DNA to form polymer-DNA nanoparticles. A range of polymer:DNA weight ratios was tested for each polymer since this parameter is known to have a critical effect on polycation-mediated transfection. Nanoparticles were then diluted into cell culture media and incubated on COS-7 cells. Unlike previous studies on poly(β-amino ester)s, the diluting media contained 10% serum to account for the effect of extracellular proteins on polymer transfection.

Figure 2:
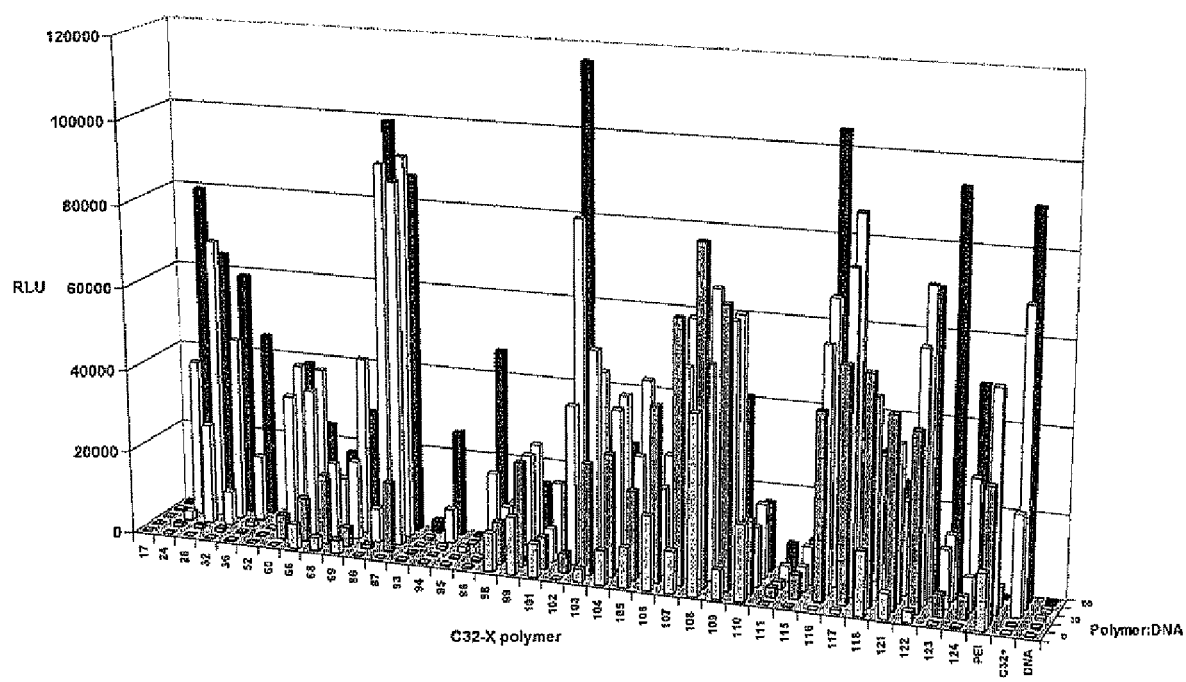
FIG. 2. Transfection of COS-7 cells. The relative light units (RLU) of luciferase reporter protein expressed are shown for each end-modified C32 polymer (C32-X) at five polymer:DNA weight ratios (10:1, 20:1, 30:1, 60:1, and 100:1).
Figure 3:
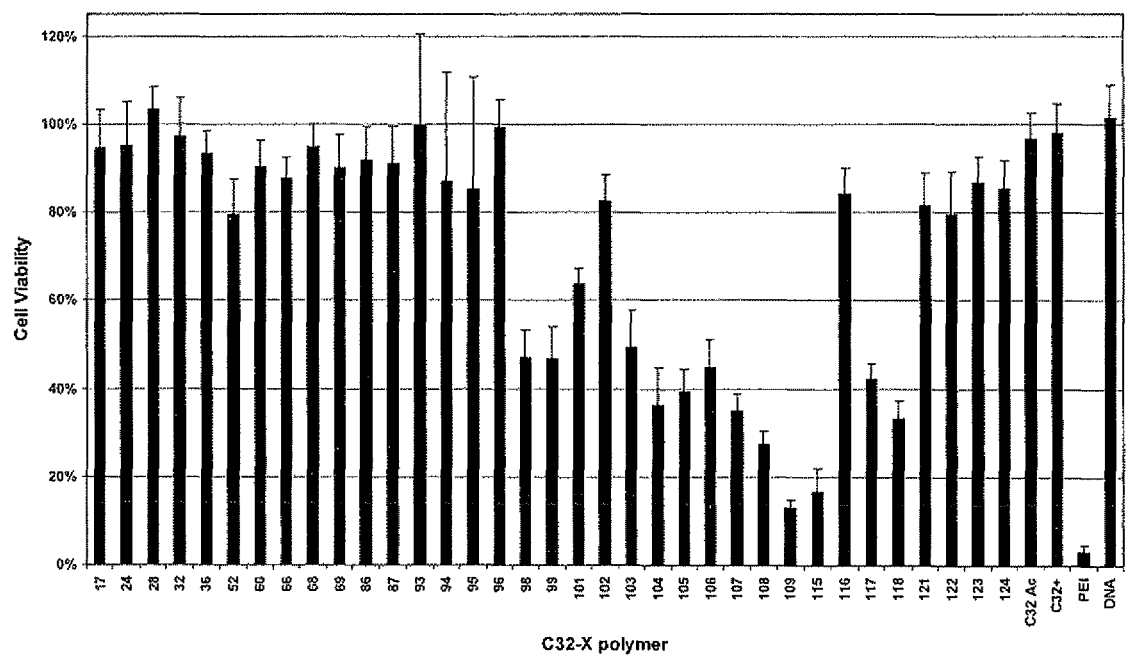
FIG. 3. Cytotoxicity levels of end-modified C32 polymers (C32-X) measured using the MTT assay. PEI, C32+, C32-Ac, and free DNA toxicity are shown the far right.

The transfection efficiencies of amine-terminated C32 polymers are shown in FIG. 2. The average luciferase expression levels, measured in relative light units (RLUs), are given for each polymer at five different polymer:DNA ratios. Also included is the transfection data for 25 kDa branched PEI, one of the most efficient commercially available polycations, and C32+, the best performing poly(β-amino ester) synthesized to date. The unmodified, acrylate-terminated C32 polymer is also shown on the far right and demonstrates weak activity that is typical of most acrylate-terminated poly(β-amino ester)s. While amine-capping reactions of this polymer where verified by $^1$H NMR analysis, the data in FIG. 3 provides functional confirmation by the large increase in transfection between acrylate- and amine-terminated polymers. An overall inspection of the data reveals that the structure of the terminal amine has a dramatic effect on the C32 transfection efficiency. In general, polymers capped with hydrophilic amine end groups containing hydroxyls or additional amines proved most effective. In contrast, chain termination with more hydrophobic amines containing alkyl chains or aromatic rings led to much lower transfection activity.

Perhaps the most important result is that very subtle structural differences in just the terminal amine can have a large effect on polymer transfection efficiency. This is most evident by comparing the C32-36 and C32-52 polymers. The C32-52 polymer, which contains a six-carbon alkyl chain extending from the terminal secondary amine, has a maximum transfection only twice that of naked DNA. In contrast, the C32-36 polymer is 34-fold more effective than C32-52, but only differs in a single hydroxyl group on carbon-6 at the chain end. In fact, the C32-36 polymer is half as effective as C32+, demonstrating that a single functional group, in this case a terminal hydroxyl, can significantly alter the polymer delivery properties. A similar effect can be seen between the C32-95 and C32-110 polymers, which consist of terminal decylamines containing either a hydroxyl group or primary amine on carbon-10, respectively. In this case, substituting the terminal hydroxyl for an amine improves the transfection performance by over one order-of-magnitude. This same substitution pattern also changes the optimal polymer:DNA ratio. Comparing two highly efficient polymers, C32-122 and C32-124, the former displays very high RLU output at a 20:1 ratio, whereas the latter requires 5-fold more polymer (i.e., a 100:1 ratio) to achieve the same effect. A similar trend is also seen between the C32-36 and C32-106 polymers. Therefore, amine capping molecules with hydroxyls and primary amines are most effective, with the latter being optimal at 5-fold lower polymer:DNA ratios in general.

Polymers terminated with primary diamine molecules had the highest transfection efficiency, as determined by both highest RLU output and lowest optimal polymer:DNA ratio. Specifically, the C32-102 polymer had a very similar transfection profile to C32+, with a maximum occurring at the highest polymer:DNA ratio of 100:1, but had an overall 30% higher RLU output. This demonstrates that a simple modification at the chain ends can significantly improve the delivery performance. Primary diamine capping also lowered the optimal polymer:DNA ratio substantially in many cases. Seven primary amine-terminated polymers had optimal polymer:DNA ratios of 20:1 while one polymer, C32-110, had a maximum RLU at a 10:1 ratio. The transfection profile at the 20:1 ratio for diamine capped polymers, C32-102 through C32-111, appears to be a skewed bell-shaped curve with a maximum occurring at the C32-108 polymer. This indicates that larger alkyl chains bridging the diamine functionalities are generally more effective than their short-chain counterparts, with an optimum of eight carbons. The C32-108 polymer had an optimal transfection at a 20:1 ratio that is almost as high as that for C32+, which requires a 100:1 ratio. Such a significant reduction in the amount of polymer needed to mediate high levels of transfection has important implications for in vivo delivery, where the amount of polymer injected needs to be limited to minimize toxic side effects.

Cytotoxicity. Many polycations have been shown to elicit considerable cell toxicity that may limit their utility as gene delivery vectors. The biocompatibility of cationic polymers is determined by a number of factors that include molecular weight, charge density, type of amines, polymer structure (linear, branched, dentritic), and chain flexibility. In general, high molecular weight polymers with a high density of primary and/or secondary amines usually result in substantially cytotoxicity. PEI and PLL are examples of such polymers and bring about significant cell damage by compromising the cell membrane, as determined by the cytosolic release of lactate dehydrogenase following exposure. Several poly(β-amino ester)s have shown considerably less toxicity than PEI, presumably due to their lower molecular weights and the lack of primary and secondary amines. We suspected that the reduced transfection of primary amine end-modified polymers at high polymer:DNA ratios may be due to increased cytotoxic activity.

The cytotoxicity of end-modified poly(β-amino ester)s was evaluated using the MTT assay. This colorimetric test is based on the ability mitochondrial reductase enzymes in viable cells to reduce 3-(4,5-dimethylthiazol-2-yl)-2,5-diphenyl tetrazolium bromide to a purple formazan. New polycationic materials for biomedical applications are frequently tested for their effects on cellular proliferation using this assay. Toxicity of end-modified polymers was assessed by performing the same transfection experiment, but assaying for metabolic activity instead of luciferase expression. All polymers were tested at the highest 100:1 polymer:DNA weight ratio, which corresponds to an approximate 400 ug/ml concentration of polymer on the cells. Toxicity analysis at such a high polymer concentration may explain the differences in polymer transfection at high polymer:DNA ratios, and simultaneously assess polymer biocompatibility under very aggressive conditions that may be important for their future use and development.

The cytotoxicity levels of end-modified C32 polymers are shown in FIG. 3. The percentage of viable cells is displayed as a function of the amine-terminated polymer. Positive and negative control conditions are shown to the far right for PEI and naked DNA. At such high polymer concentrations, PEI is known to be very cytotoxic and is reflected by the low 3% cell viability. In contrast, both C32+ and the acrylate-terminated C32 polymer (C32-Ac) show no significant affects on the growth and metabolism of COS-7 cells. This result for C32-Ac is somewhat surprising though since other acrylate-terminated poly(b-amino ester)s have shown considerable toxicity at this concentration.

The majority of end-modified C32 polymers show good biocompatibility. This is especially true of all polymers capped with mono-primary amine reagents, regardless of the functional groups extending from the amine. Aromatic, alkyl, hydroxyl, secondary and tertiary amines, and imidazole functionalities at the chain end points do not appear to invoke any adverse effects. Therefore, elevated cytotoxic effects do not sufficiently explain the low transfection ability of polymers terminated with the more hydrophobic amines. In contrast to the polymers capped with mono-amines, polymers terminated with di-primary amine molecules compromise cell viability to varying extents. While the increased charge is a determining factor, the overall toxicity is also strongly dependent on the hydrophobicity of the end group. In general, increasing the size of the alkyl chain bridging the amine groups increases the toxicity, as is evident by comparing the C32-102 through C32-109 polymers. Furthermore, C32-121, a polymer containing a terminal polyethyleneglycol amine with an eight atom spacer between amine groups, is much less toxic than the corresponding alkyl derivative, C32-108. This indicates that both the spacing between amines, and the degree of hydrophobicity in the terminal amine spacer, are important determinants of end-amine toxicity.

These significant cytotoxic effects, in large part, explain the decreasing transfection ability of most primary diamine capped polymers at the higher polymer:DNA ratios. The additional charge, in conjunction with increased hydrophobicity, may be particularly damaging to the cell membranes since both properties are known to disrupt lipid bilayers.

DNA Binding. An important requirement for cationic transfection agents is the ability to bind and condense plasmid DNA for cell entry. In general, higher molecular weight polymers with increased cationic charge density display stronger DNA binding at low polymer:DNA ratios. While strong electrostatic interactions are important to effectively condense and deliver the DNA, the polymer must possess a mechanism to unbind from the DNA once inside the nucleus. For this reason, the poly(b-amino ester)s may be particularly advantageous since they undergo hydrolysis with short half-lives, which may aid in DNA packaging.

The binding and condensation of DNA by polycations is often monitored using an agarose gel electrophoresis assay. This assay can be used to adequately determine the minimum polymer:DNA ratio required for plasmid condensation but does not provide any information on the strength of this interaction. In contrast, dye binding assays provide a quantitative measure of the polymer-DNA binding event. As a result, we utilized a PicoGreen dye penetration assay to determine the strength and degree of DNA binding by the end-modified poly($\beta$-amino ester)s. In this assay, polymer-DNA complexes are formed in a manner similar to their preparation for transfection experiments. The complexes are then mixed with a PicoGreen dye solution, diluted into cell culture media, and the solution fluorescence is measured. The dye exhibits fluorescence only when it intercalates between the DNA base pairs. High fluorescence is typically seen with free plasmid, but significant reductions can occur for polymer-DNA complexes in which the DNA is partially shielded from dye penetration. The magnitude of this fluorescence reduction relative to free DNA correlates to the strength of the polymer-DNA interaction.

Figure 4:
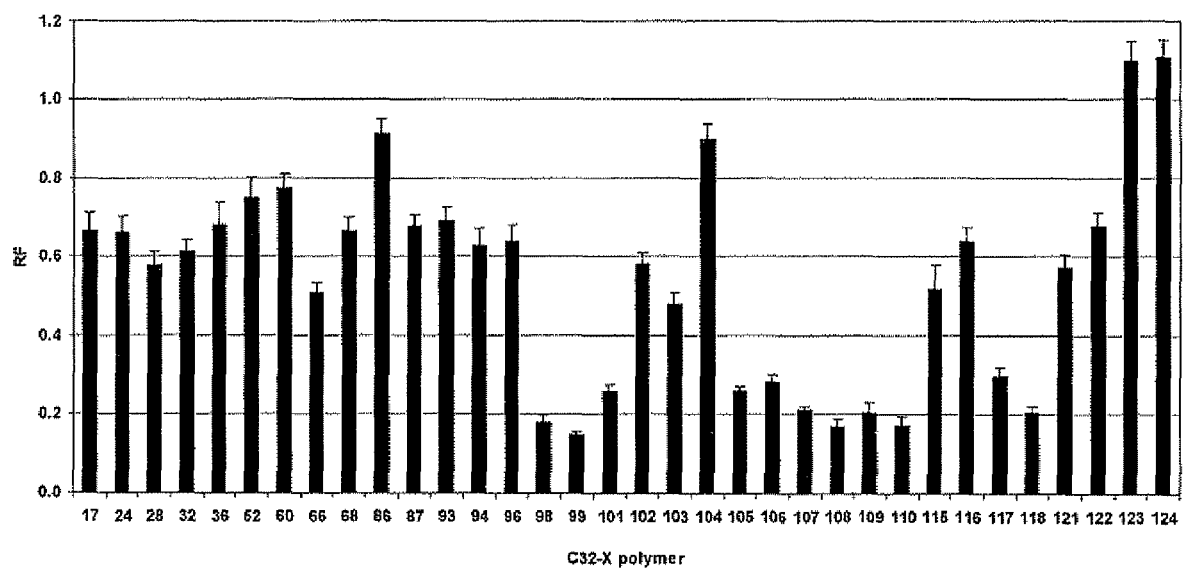
FIG. 4. Polymer-DNA binding measured using a PicoGreen assay. Fluorescence reductions relative to free DNA (RF) are shown for each end-modified C32-polymer (C32-X) at the optimal transfecting polymer:DNA ratio for each polymer.

The DNA binding levels for each end-modified polymer are shown in FIG. 4. Fluorescence measurements relative to free DNA are given at the optimal transfecting polymer:DNA ratio for each polymer. With the exception of mono-amine PEG terminated polymers, all end-modified materials displayed some level of DNA binding. In general, increased cationic charge at the end groups enabled stronger polymer-DNA interactions. This effect is most noticeable by comparing the results of the PEG amine-capped polymers. The mono-amine capped polymers, C32-123 and C32-124, displayed no measurable binding. However, the substitution of a single primary amine for a hydroxyl at the chain ends (C32-121 and C32-122) leads to increased polymer-DNA binding and less dye penetration. This result indicates that a single functional group only at the very end point of the polymer can bring about large changes in polymer function. Similar conclusions were reached when assessing the overall transfection ability of the polymer but now are seen at just one part of the delivery process.

Perhaps the most noticeable trend in the data is that polymers terminated with primary diamine molecules are most effective at condensing and binding DNA. Additional secondary or tertiary amines at the chain ends were not as effective to increase the DNA binding ability of the polymer, possibly due to pKa differences or a more sterically crowded environment that may prevent their electrostatic interaction with DNA. Similar to the cytotoxicity data, more effect is seen with increased terminal hydrophobicity in addition to the added positive charge. In general, smaller relative fluorescence is seen as the alkyl chain length is increased between terminal amine groups, as is evident by comparing polymers C32-102 through C32-110. These results are supported by weaker DNA binding ability of polymers terminated with the more hydrophilic primary ethyleneglycol amine polymers (C32-121 and C32-122).

Particle Sizing. Simple electrostatic interactions between the polycation and the negatively charged DNA can often lead to their spontaneous self-assembly into cationic polymer-DNA nanoparticles. The physical properties of these complexes are particularly important for their subsequent uptake into cells. Complexes with a positive surface charge and a diameter less than 200 nm are usually sufficient for cellular endocytosis. These properties are dependent upon a number of polymer characteristics and the polymer-DNA mixing technique. Since the terminal amine has demonstrated significant effects on the DNA binding ability of polymers, it should also affect the physical properties of the polymer-DNA complexes.

The effective diameter of complexes formed between end-modified poly($\beta$-amino ester)s and plasmid DNA were measured using dynamic light scattering. Polymer-DNA complexes were formed at the optimal transfecting polymer:DNA ratio for each polycation and then diluted into cell culture media prior to each measurement. Concentrations, solution compositions, and polymer-DNA complexing procedures in each step were identical to those used in the transfection assay. In this way, the nanoparticle physical properties measured in this experiment reflect the actual particle properties in the transfection screen.

Figure 5:
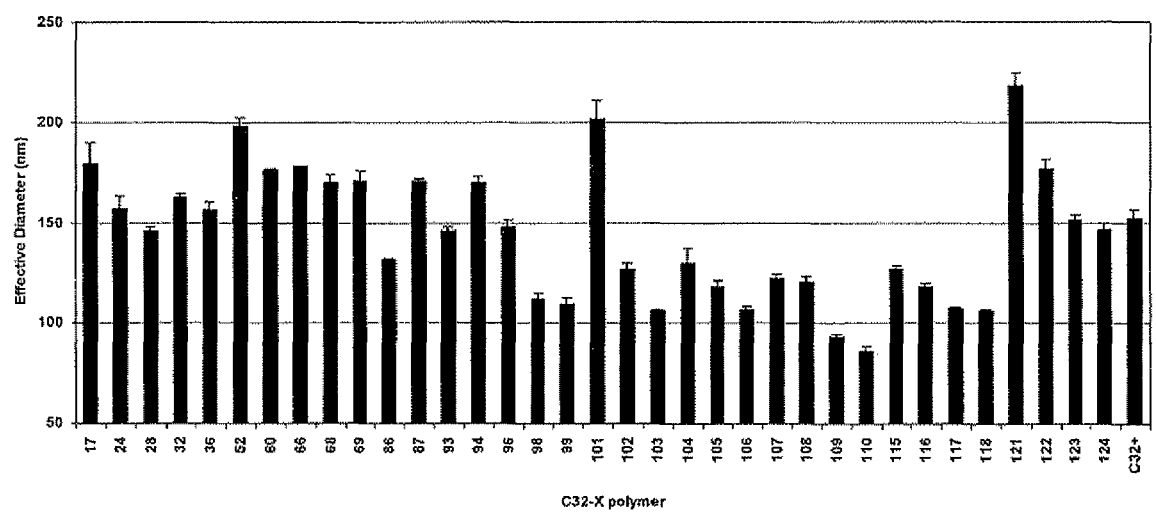
FIG. 5. Polymer-DNA complex size measured by dynamic light scattering. The effective diameter of complexes are shown for each end-modified C32 polymer (C32-X) at the optimal transfecting polymer:DNA ratio for each polymer. In general, diamine-capped polymers form smaller polymer-DNA complexes than C32+. The smallest particle size in serum is 86 nm. For C32+, it is 152 nm.

Average diameters of the polymer-DNA complexes are presented in FIG. 5 for each end-modified C32 polymer. The average diameter varied between 85 to 220 nm, demonstrating the crucial effects of terminal amine structure on the physical properties of polymer-DNA complexes. Also shown on the far right is the average diameter of the C32+ complexes, which is determined to be 152 nm. In a previous study, C32+ complexes were diluted into HEPES buffer and subsequently measured to be 79 nm in diameter. This difference in particle size illustrates the large effect of serum proteins to disrupt or interact with cationic polymer-DNA complexes. Increases in polymer-DNA complex size in the presence of serum have been seen in studies with other polycations such as PLL and PEI, and is a well known effect on polymer-DNA properties. Importantly, the C32+ complex diameter is still below the threshold for endocytosis and maintains high transfection levels.

All end-modified polymers formed complexes with effective diameters in a suitable range for cellular uptake. Only two polymers, C32-101 and C32-121, formed complexes with diameters slightly above 200 nm. The former material consists of highly charged chain end groups whereas the latter contains a short PEG diamine at the chain end points. In general, the PEG terminated polymers (C32-121 to C32-124)

formed larger complexes with diameters between 150 to 220 nm. Despite the large size and weak DNA binding of these polycations, they can still deliver DNA with relatively high efficiencies. This effect is also true of most polymers terminated with mono-primary amine molecules. These polymers, shown on the left side of FIG. 5, mostly result in complexes with diameters greater than 150 nm and lower DNA binding ability than primary diamine capped polymers. Although a general conclusion cannot be made, it is interesting to note that some polymers with very low transfection efficiencies (e.g., C32-117, -52, -101) also form relatively large complexes, suggesting that their physical properties may not be conducive to uptake.

Similar to the DNA binding data, particle sizing appears to be more favorable for polymers capped with primary diamine molecules. For almost all of these polymers, their complexes with DNA have diameters between 85-130 nm. The more hydrophilic PEG diamines, C32-121 and C32-122, are the exception, illustrating the importance of a hydrophobic alkyl chain space between amines at the terminus. Although the trend is not as pronounced as that for the DNA binding, it appears that the sizing is somewhat improved by increasing the alkyl chain length. This is especially true at the long chain lengths where C32-109 and C32-110 form the smallest complexes that have diameters less than 100 nm. These polymers assemble into smaller complexes with DNA compared to those terminated with additional secondary and/or tertiary amines, again illustrating the benefits of primary amines at the chain ends over these other amine functionalities. Consequently, it appears that polymers terminated with alkyl primary diamine molecules have the strongest DNA binding characteristics and assemble into the smallest polymer-DNA complexes.

DNA Uptake. Differences in the physical properties of polymer-DNA complexes can naturally lead to differences in the rates and levels at which they are endocytosed into cells. Previous studies with poly(b-amino ester)s have shown that smaller complexes with high cationic surface charge are more favorable for cellular uptake. In addition, amine termination has been shown to promote higher cellular internalization over the corresponding acrylate-terminated polymer. In light of these findings and the terminal amine affects on polymer-DNA properties, we measured the uptake levels of end-modified C32 polymers. Although previous studies with poly(β-amino ester)s used a novel fluorescence-based technique, we choose to use a DNA extraction and RT-PCR amplification protocol to quantify the amount of endocytosed DNA. This method provides (1) high sensitivity due to the PCR amplification, (2) linearity over several orders-of-magnitude, (3) the ability to quantify DNA uptake without pre-labeling the plasmid, and (4) a high-throughput, 96-well plate format to simultaneously and rapidly analyze all polymers. For this experiment, transfections were performed following the standard protocol using a β-galactosidase (β-gal) plasmid. This DNA was isolated from the cells after a four hour post-incubation period and amplified using RT-PCR. The total amount of β-gal DNA harvested for each sample was calculated using a standard curve and normalized to the COS-7 genomic DNA.

Figure 6:
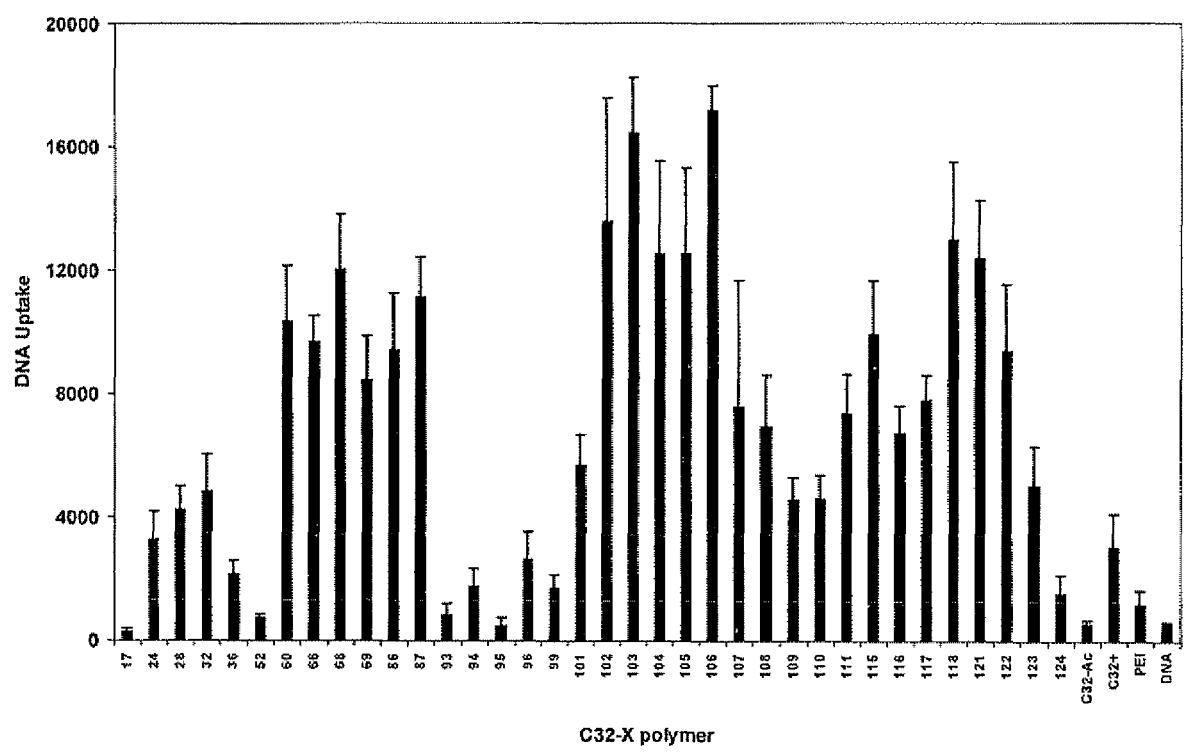
FIG. 6. Plasmid DNA uptake into COS-7 cells. DNA uptake levels are shown in number of plasmids per COS-7 DNA fluorescence. Diamine-capped polymers increase DNA uptake five times over C32+ and PEI.

The DNA uptake levels for each end-modified polymer are shown in FIG. 6. The results are expressed as the number of plasmids endocytosed per nanogram of total DNA for each polymer at its optimal transfecting polymer:DNA ratio. Also shown is the low uptake level of free plasmid DNA, which is most likely due to its large size and high anionic charge density that repels the cell surface. Positive control polymers C32+ and PEI are also shown to the far right, both of which increase DNA uptake by approximately 5-fold over the free plasmid. On the other hand, plasmid condensation with the C32-Ac polymer did not improve uptake to any measurable level, which explains the inability of this polymer to mediate transfection. The large difference between C32+ and C32-Ac, both in terms of uptake and transfection, highlight the importance of amine termination to improve the C32 polymer delivery properties.

The results in FIG. 6 demonstrate that the type of amine at the chain ends has a considerable effect on the endocytosis of C32 polymer-DNA complexes. The uptake levels varied over two orders-of-magnitude among the end-modified polymers, with polymer C32-106 mediating the highest plasmid internalization that is 30-fold greater than free DNA. The most obvious trend in the data is the improved uptake that occurs for polymers with additional terminal amines. This is evident for polymers containing extra secondary and tertiary end amines (C32-60 through C32-87) and mostly for those with an additional primary end amine (C32-102 through C32-122). These results suggest that conjugation of targeting ligands to the chain ends may be a promising strategy to achieve cell specific delivery.

The differences in uptake between each polymer also explain some important differences in their transfection efficiencies. First, many polymers that are poor transfection agents also displayed very low uptake (e.g., C32-17, -52, -93, -95). This indicates that the extra charge alone at the chain end points (compared to C32-Ac) is necessary but not sufficient to promote C32 endocytosis. Specific functional groups at the chain ends, such as hydroxyls and amines, have an enhanced capacity to interact with cell surfaces and increase uptake as compared to more hydrophobic terminal segments. For example, the transfection differences between C32-36 and C32-52 are largely related to their differences in uptake. This comparison demonstrates that a single functional group in the polymer chain, in this case a terminal hydroxyl, can have a large effect on cell interactions and endocytosis. Extending the comparison further, C32-106 differs from these two materials by a terminal primary amine. The results show that this single substitution at the terminal amine carbon-6 can increase uptake by over 20-fold. This effect is even more surprising considering that the polymer:DNA ratio used for C32-106 is 20:1, 5-fold less than that used for C32-36 and C32-52. In general, the increased uptake by the polymers capped with primary diamines largely explains their increased effectiveness at reduced polymer:DNA ratios. The overall transfection levels may not be substantially improved over C32+ and other non-primary amine polymers because (1) the transfection levels are already very high and could be close to a saturation limit, and (2) the terminal functionalities may have important effects on other downstream gene delivery barriers such as endosomal escape, cytosolic trafficking, or nuclear import.

Transfections of other Poly(β-amino ester)s. Terminal amine modifications to the C32 polymer are shown here to have a large effect on several gene delivery properties. In particular, differences in the end amine structure have resulted in significantly improved DNA binding, the formation of much smaller polymer-DNA complexes, enhanced cellular endocytosis of these complexes, and increased transfection efficiencies, especially at the lower polymer:DNA ratios. Since the terminal amine can affect and improve the C32 polymer performance, such modifications may also alter the transfection profiles and gene delivery properties of other poly(β-amino ester)s. Furthermore, given that the terminal amine has a large affect on cellular uptake, simple amine-capping may be an effective means to promote cell specific delivery.

To assess the combined effects of internal polymer structure and amine termination on transfection, we synthesized and end-capped two additional poly(β-amino ester)s, D60 and C20. The former is an effective gene delivery polymer with a structure very different from that of C32. Conversely, the C20 polymer is a very poor transfection agent but is structurally very similar to C32, differing only in the length of the alcohol side chain. These polymers were end-capped with the primary diamine molecules that produced the most effective C32 modifications in terms of both overall transfection and lower optimal polymer:DNA ratio. Transfection screens of all three polymer types (C32, D60, and C20) were performed on COS-7 and HepG2 cell lines. The latter was included because (1) it is a human cancer cell line frequently used to test new polymers for gene delivery, (2) transfection of liver cells has therapeutic relevance, and (3) it provides a second cell line to evaluate potential targeting effects of each polymer. Lastly, all transfections were carried out at a 20:1 polymer:DNA weight ratio.

Figure 7:
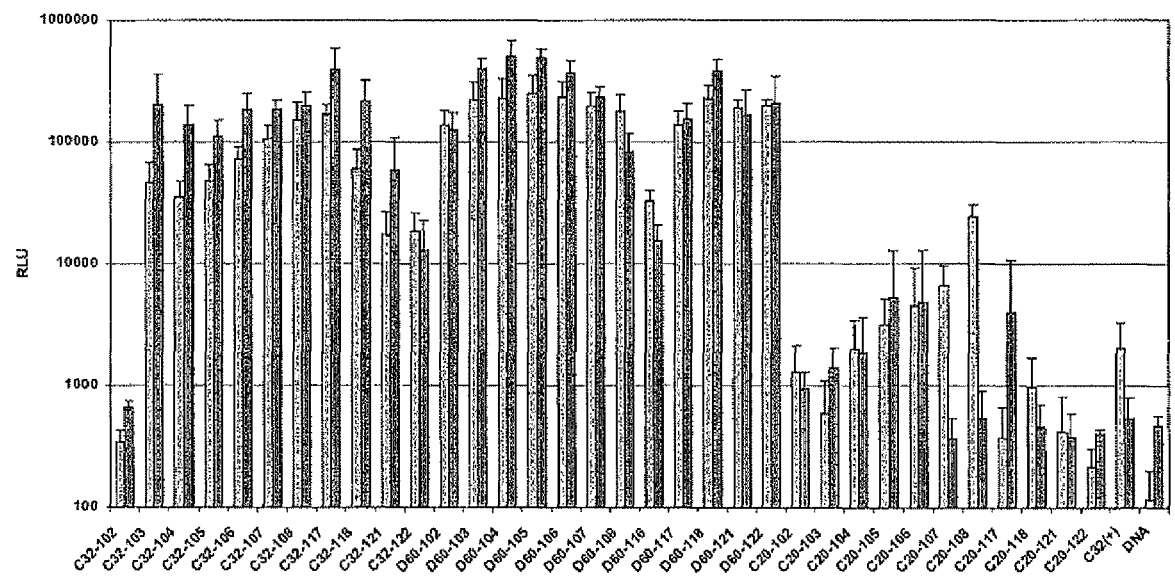
FIG. 7. Transfection of COS-7 (blue bars) and HepG2 (red bars) by end-modified C32, D60, and C20 polymers at a 20:1 polymer:DNA ratio.

The transfection efficiencies for the end-modified C32, D60, and C20 polymers are shown in FIG. 7. Measured RLUs are given for each polymer for both the COS-7 (blue bars) and HepG2 (red bars) cell lines. First, it can be seen that the C32 polymers are able to transfect both cells lines, indicating that these materials may be effective delivery systems for a variety of cells. In general, C32 polymers terminated with primary alkyl diamines (C32-103 through C32-108) were more effective than those with PEG spacers (C32-121 and -122), indicating that a degree of hydrophobicity at the chain ends is preferential for these polymers. For both cell types it appears that at least a three carbon spacer between terminal amines is necessary to obtain effective gene delivery with C32 polymers at the 20:1 ratio. The C32-103 efficiency is 130- and 300-fold higher than C32-102 on the COS-7 and HepG2 cell lines, respectively. This result demonstrates that a single additional carbon at the chain ends can alter the transfection levels by two orders-of-magnitude.

In addition to the C32 polymers, many of the end-modified D60 polymers were highly effective gene delivery agents. In fact, ten of these polymers were more efficient at the reduced 20:1 ratio than C32+ at its optimum 100:1 ratio (FIG. 2). The best performing polymer, D60-105, has a transfection efficiency almost 3-fold higher than the optimal C32+ formulation. Unlike the end-modified C32 polymers, highly efficient D60 polymers were formed with both alkyl and PEG terminal diamines. These results indicate that it is necessary to concurrently optimize both the interior sequence and end-amine structure to arrive at the most efficient poly(β-amino ester).

In comparison to the C32 and D60 polymers, all of the C20 modifications were much less efficient. Nevertheless, the C20 gene delivery efficiency could be remarkably improved by proper end-functionalization. The most effective modified polymer, C20-108, was over two orders-of-magnitude more efficient than C20-122. The C20-108 efficiency was still 3- to 4-fold less than the optimal C32+ transfection level, but was never tested at higher ratios where it may have better performance. Regardless, the conversion of a completely ineffective polymer into a material with reasonable gene delivery capabilities by end-modification is an important result for the future development of poly(β-amino ester)s.

Some differences in polymer transfection could be seen between the COS-7 and HepG2 cell lines. The most significant difference occurred for the C20-108 polymer, which was two orders-of-magnitude more effective in COS-7 cells over the HepG2 cells. A similar but less dramatic effect was seen with the C20-107 polymer, suggesting that C20 termination with long alkyl diamines may be a possible means to target fibroblasts. For all other polymers, including the C32 and D60, most transfection differences between the cell lines were within an order-of-magnitude for each polymer. The inability to achieve a high level of cell specific delivery is not surprising given that none of these end amines or polymer sequences have an obvious mechanism to preferentially bind to a given cell type.

siRNA Delivery. In addition to DNA delivery, some poly (β-amino ester)s have shown the ability to deliver siRNA to down-regulate protein expression (unpublished data). Initial experiments with a previous polymer library have specifically identified polymer AA28 as a promising candidate for further development. As a result, we synthesized an acrylate-terminated AA28 base polymer (FIG. 1D) and explored the effects of amine end-capping on AA28 siRNA delivery. A select group of primary diamine capping reagents was used along with the highly charged 101 compound. Four additional capping reagents were included that contain multiple amines (125 through 128) to assess the effects of highly charged ends on siRNA-mediated knockdown. As a model system, we delivered firefly-luciferase siRNA to a HeLa cell line that stably expresses both firefly and *renilla* luciferase proteins. The decrease in firefly levels was used to quantify knockdown while any decreases in *renilla* levels were used to measure and correct for cytotoxic effects.

Figure 8:
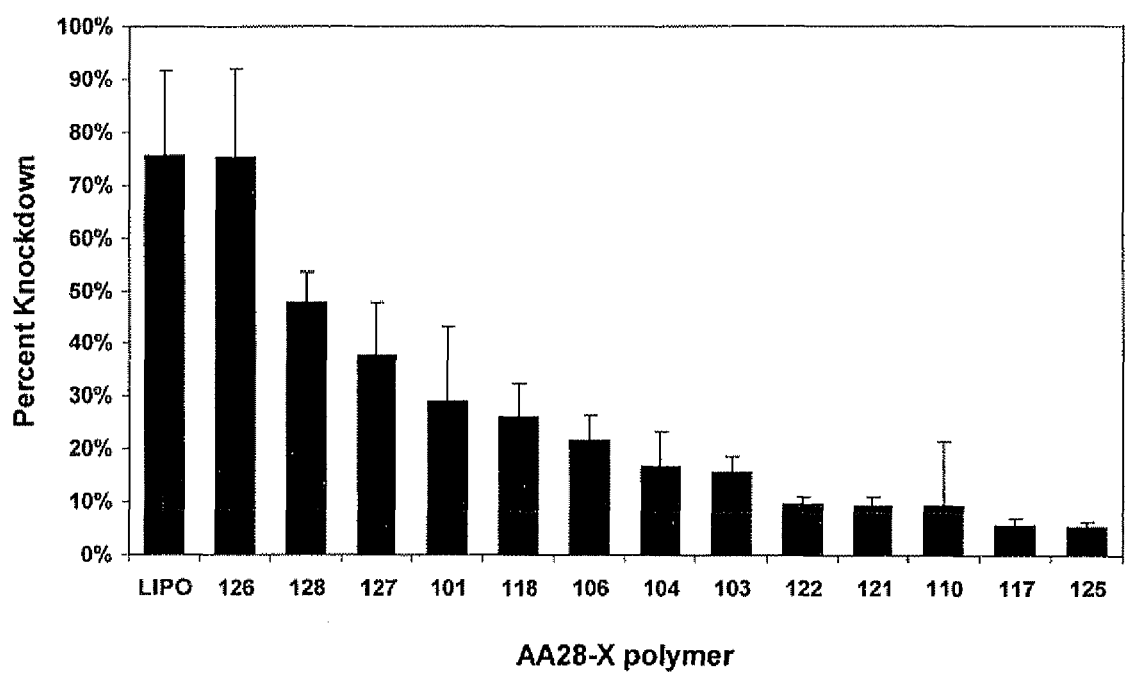
FIG. 8. siRNA delivery with AA28 poly(beta-amino esters). Percent knockdown of firefly luciferase in HeLa cells is shown for each end-modified AA28 polymer (AA28-X) at its optimal polymer:siRNA ratio. Certain end-modified polymers have been found to be as effective as Lipo2000. Higher positive charge density at the ends results in higher silencing.
Figure 9:
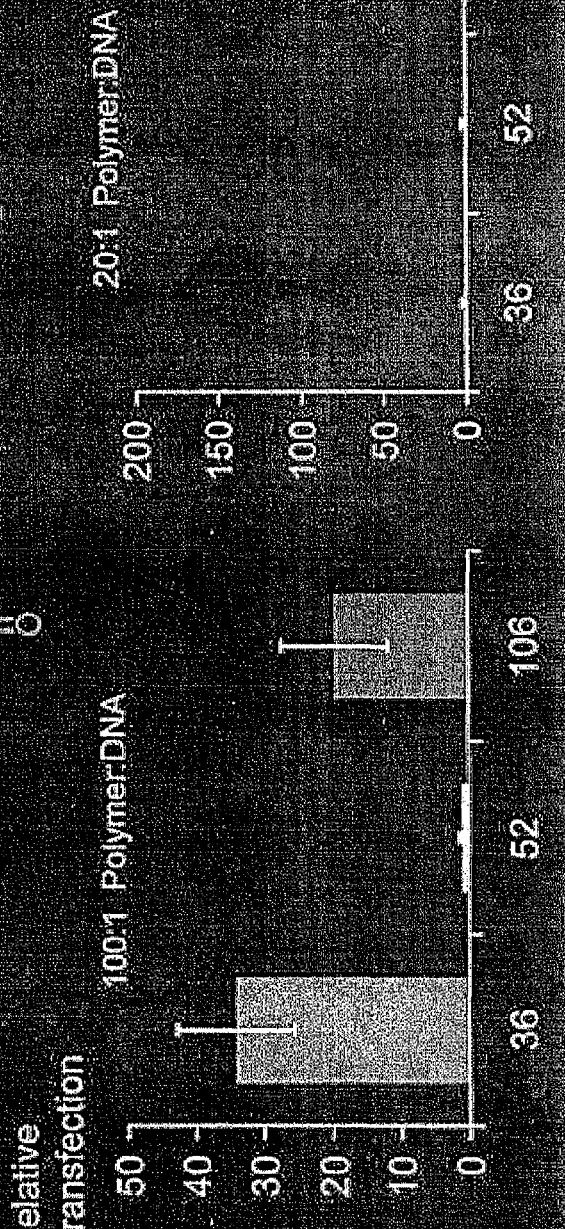
FIG. 9. Transfection of cells by end-modified C32 at 100:1 polymer:DNA and 20:1 polymer:DNA ratios.
Figure 10:
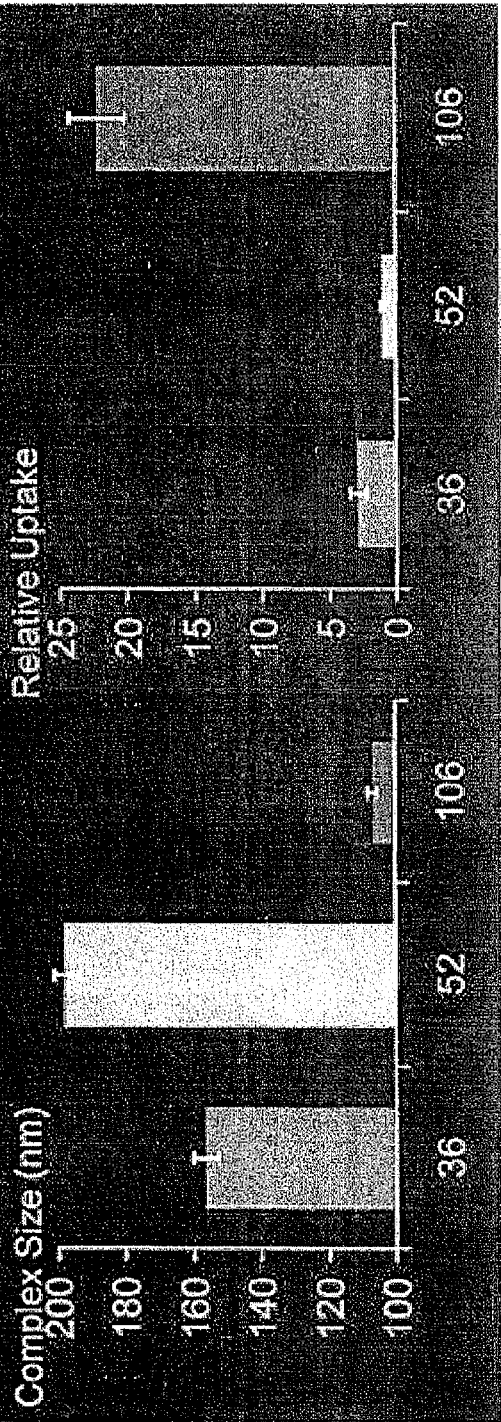
FIG. 10. Polymer-DNA complex size and plasmid DNA uptake for end-modified C32 (C32-36; C32-52; C32-106).

The percent knockdown of firefly luciferase for each end-modified AA28 polymer at its optimal polymer:siRNA ratio is shown in FIG. 8. Similar to the DNA delivery experiments, the end-amine structure of the polymer has a large effect on its siRNA delivery efficiency. The most effective polymer discovered, AA28-126, can mediate 75% knockdown of the firefly luciferase level. This efficiency is equal to that seen with Lipofectamine, one of the most effective cationic lipid formulations for siRNA delivery. Interestingly, the AA28-126 polymer derivative contains the most cationic end group. In fact, the percent knockdown appears to increase as the charge density is increased at the chain ends, indicating that this property may be generally important for siRNA delivery with poly(β-amino ester)s.

Several effective end-modified polymers have been discovered for siRNA delivery. With the large pool of base polymers and the availability of many amine molecules, a wide array of structurally diverse poly(β-amino ester)s can be prepared using the end-modification and screening strategy. Since the test of AA28 end capping produced several strong hits, a much larger library of materials would lead to the identification of many poly(β-amino ester)s capable of high DNA and siRNA delivery efficiencies.

Experimentals

Materials. Polyethylenimine (water free, $M_w$~25 kDa, $M_n$~10 kDa), 3-amino-1-propanol (99%), N,N'-dimethylethylenediamine (99%), and anhydrous THF were purchased from Sigma-Aldrich (St. Louis, Mo.). A 25 mM sodium acetate buffer solution pH 5.2 (NaAc buffer) was prepared by diluting a 3 M stock (Sigma-Aldrich). 1,4-Butanediol diacrylate (99+%) and 5-amino-1-pentanol (97%) were from Alfa Aesar (Ward Hill, Mass.); Ethoxylated (2) bisphenol A diacrylate was from Scientific Polymer Products, Inc. (Ontario, N.Y.); Amine capping reagents were purchased from Sigma-Aldrich, Alfa Aesar, Acros Organics/Fisher Scientific (Pittsburgh, Pa.), TCI America (Portland, Oreg.), Molecular Biosciences (Boulder, Colo.), and Toronto Research Chemicals (Ontario, Canada). All chemicals were used as received without any further purification. PicoGreen and Redi-plate 96 PicoGreen dsDNA Quantification Kit were purchased from Molecular Probes (Eugene, Oreg.). pCMV-Luc plasmid DNA stock solution (1 mg/ml in water) was obtained from Elim Biopharmaceuticals (Hayward, Calif.). gWIZ-β-gal plasmid DNA stock solution (5 mg/ml) was obtained from Aldevron (Fargo, N. Dak.). The MTT Cell Proliferation Assay, Bright Glo™ Luciferase Assay Kits, and Dual Glo™ Luciferase Assay Kits were purchased from Promega Corporation (Madison, Wis.). White and black polystyrene tissue culture treated 96-well plates and half area polystyrene 96-well plates were obtained from Corning Costar. Clear polystyrene tissue culture treated 96-well plates were obtained from Becton Dickinson (Bedford, Mass.). Polypropylene 96-well deep-well plates were purchased from Sigma-Aldrich.

Cell Culture. COS-7 cells were obtained from ATCC (Manassas, Va.) and maintained in phenol red-free DMEM supplemented with 10% fetal bovine serum and 100 units/ml of penicillin/streptomycin. HepG2 cells were obtained from ATCC and grown in MEM supplemented with 10% fetal bovine serum, 2 mM L-glutamine, 0.1 mM non-essential amino acids, 100 units/ml of penicillin/streptomycin, and 1 mM sodium pyruvate. Luciferase expressing HeLa cells were maintained in DMEM supplemented with 10% fetal bovine serum, 100 units/ml of penicillin/streptomycin, 500 ug/ml zeocin (Sigma-Aldrich), and 0.5 ug/ml puromycin. All cell culture reagents were purchased from Invitrogen Corporation (Carlsbad, Calif.) unless otherwise noted. All cell lines were grown at 37° C., 5% $CO_2$ atmosphere.

Methods. $^1$H NMR was conducted on a Varian Unity spectrometer (300 MHz).

Synthesis of Acrylate-Terminated Poly(β-amino ester)s. All acrylate-terminated polymers were synthesized by mixing the appropriate monomers in a 1.2:1.0 molar ratio of diacrylate:amine. C32-Ac was prepared by mixing 793 mg of 1,4-butanediol diacrylate (4 mmol) with 344 mg of 5-amino-1-pentanol (3.3 mmol). D60-Ac was prepared by mixing 1443 mg of ethoxylated (2) bisphenol A diacrylate (3.4 mmol), 250 mg of N,N'-dimethylethylenediamine (2.8 mmol), and 1 ml of DMSO. C20-Ac was prepared by mixing 793 mg of 1,4-Butanediol diacrylate (4 mmol) with 250 mg of 3-amino-1-propanol (3.3 mmol). Polymerizations were performed in Teflon-lined screw cap vials under magnetic stirring at 90° C. for 24 hours. $^1$H NMR of C32-Ac (d$_6$-DMSO): δ (ppm) 1.2-1.4 (m, —NCH$_2$(CH$_2$)$_3$CH$_2$OH), 1.6 (bs —N(CH$_2$)$_2$COOCH$_2$CH$_2$—), 2.4 (m, —COOCH$_2$CH$_2$N— and —NCH$_2$(CH$_2$)$_4$OH), 2.6 (m, —COOCH$_2$CH$_2$N—), 3.4 (bs, —N(CH$_2$)$_4$—CH$_2$OH), 4.0 (bs, —N(CH$_2$)$_2$COOCH$_2$CH$_2$—), 4.1 (t, CH$_2$CHCOOCH$_2$CH$_2$—), 4.4 (bs, —N(CH$_2$)$_5$OH), 5.9 (d, CH$_2$CHCOOCH$_2$CH$_2$—), 6.2 (m, CH$_2$CHCOOCH$_2$CH$_2$—), 6.3 (d, CH$_2$CHCOOCH$_2$CH$_2$—).

Synthesis of Amine-Capped Poly(β-amino ester)s. Acrylate-terminated polymers were dissolved in DMSO at 31.13% wt/wt. Amine capping reagents were dissolved in DMSO at 0.25 M. End chain capping reactions were performed by mixing 321 mg of polymer/DMSO solution with 800 µl of amine solution. Reactions were performed in eppendorf tubes with constant agitation for 24 hours. Polymers were stored at −20 deg C. until used for each experiment. $^1$H NMR of C32-Ac capped with 5-amino-1-pentanol (C32-32) (d$_6$-DMSO): δ (ppm) 1.2-1.4 (m, —NCH$_2$(CH$_2$)$_3$CH$_2$OH), 1.6 (bs —N(CH$_2$)$_2$COOCH$_2$CH$_2$—), 2.4 (m, —COOCH$_2$CH$_2$N— and —NCH$_2$(CH$_2$)$_4$OH), 2.6 (m, —COOCH$_2$CH$_2$N—), 3.4 (m, —N(CH$_2$)$_4$—CH$_2$OH), 4.0 (bs, —N(CH$_2$)$_2$COOCH$_2$CH$_2$—).

Polymer Transfections. COS-7 cells (15,000 cells/well) or HepG2 cells (5,000 cells/well) were plated in opaque 96-well plates and allowed to adhere overnight. Polymers at 100 mg/ml in DMSO were diluted accordingly into NaAc buffer to concentrations that yield the different polymer:DNA weight ratios. One hundred microliters of diluted polymer solution was mixed vigorously with 100 µl of DNA (60 µg/ml in NaAc buffer) in a 96-well polystyrene plate. The solutions were left undisturbed for 5 minutes after which time 120 µl of each was added to 800 µl of cell culture media in a deep-well polypropylene plate. The media over the cells was then removed with a 12-channel aspirator wand and followed by the addition of 150 µl/well of polymer-DNA complex solution. Complexes were incubated over the cells for one hour after which time they were aspirated off and replaced with 105 µl/well of fresh cell culture media. Cells were allowed to grow for three days at 37° C., 5% $CO_2$ and then analyzed for luciferase protein expression.

Luciferase expression was analyzed using Bright-Glom assays kits. Briefly, 100 µl/well of Bright-Glo solution was added to the cell plates. The plates were gently agitated to promote mixing for 2 minutes. Luminescence was then measured on a Perkin Elmer Victor 3 plate luminometer using a 1% neutral density filter and a one second per well counting time.

Measurements of Polymer Cytotoxicity. Cytotoxicity measurements of polymer-DNA complexes were performed essentially as described for the transfection experiments except that cellular metabolic activity was measured instead of Luciferase protein expression. One day after the transfection, MTT reagent was added to the cell plates at 10 µl/well. The plates were incubated at 37° C. for 2 hours. Detergent reagent was then added at 100 µl/well and the cell plates were left in the dark at room temperature for 4 hours. Optical absorbance was measured at 570 nm using a Molecular Devices SPECTRAmax PLUS384 absorbance plate reader and converted to percent cell viability relative to untreated cells.

Polymer-DNA Binding Assay with PicoGreen. Polymer solutions at 100 mg/ml in DMSO were diluted into NaAc buffer to a final concentration of 6 mg/ml. In a half area 96-well plate, 50 µl/well of diluted polymer was added to 50 µl/well of DNA (60 µg/ml in NaAc buffer). The solutions were mixed vigorously and allowed to sit undisturbed for 5 minutes to allow for polymer-DNA complexation. After this time, 100 µl/well of PicoGreen solution was added. PicoGreen working solution was prepared by diluting 80 µl of the purchased stock into 15.2 ml NaAc buffer. After 5 minutes, 30 µl/well of polymer-DNA-PicoGreen solution was added to 200 µl/well of DMEM media in black 96-well polystyrene plates. The plate fluorescence was then measured on a Perkin Elmer Victor 3 plate reader using a FITC filter set (excitation 485 nm, emission 535 nm). The relative fluorescence (RF) was calculated using the following relationship:

$$RF = (F_{sample} - F_{blank})/(F_{DNA} - F_{blank})$$

where $F_{sample}$ is the fluorescence of the polymer-DNA-PicoGreen sample, $F_{blank}$ is the fluorescence of a sample with no polymer or DNA (only PicoGreen), and $F_{DNA}$ is the fluorescence of DNA-PicoGreen (no polymer).

Polymer-DNA Complex Size. Polymer solutions at 100 mg/ml in DMSO were diluted into NaAc buffer the appropriate concentration. Concentrations were adjusted for each polymer so that the final polymer:DNA ratio was the same that produced the highest transfection. To prepare polymer:DNA complexes, 100 µl of diluted polymer was added to 100 µl of DNA (60 µg/ml in NaAc) and pipetted vigorously. Complexation was allowed to proceed undisturbed for 5 minutes after which time 150 µl of the sample was diluted into 1.8 ml of DMEM media. Polymer:DNA complex size was measured on a ZetaPALS dynamic light scattering detector (Brookhaven Instruments Corporation, Holtsville, N.Y.; 15 mW laser; 676 nm incident beam, 90° scattering angle).

Effective particle diameters were calculated from the autocorrelation function using the MAS option of the BIC particle sizing software assuming a log normal distribution. The solution viscosity and refractive index were assumed equal to pure water at 25° C.

Cellular Uptake Assay. Uptake measurements of polymer-DNA complexes were performed essentially as described for the transfection experiments but using the b-galactosidase plasmid. Instead of quantifying protein expression levels after three days, total cellular DNA was isolated fours hours post-transfection using a DNeasy 96 Tissue Kit (Qiagen; Valencia, Calif.) following the manufacturer instructions. Total DNA was quantified using a Redi-Plate 96 PicoGreen dsDNA Quantification kit following the supplied instructions. The amount of 1-gal DNA delivered was quantified using RT-PCR with a Taqman primer and probe set specific for the 1-gal plasmid (Applied Biosystems; Foster City, Calif.). After activating the Taq enzyme at 95° C., 40 cycles of amplification were performed, with each cycle consisting of 95° C. for 15 seconds, 60° C. for one minute, followed by a fluorescent plate read using a Chromo4 Continuous Fluorescence Detector (MJ Research; Waltham, Mass.). Plasmid copy numbers were determined by comparing the RT-PCR cycle threshold values to a plasmid standard curve and analyzed using the Opticon Monitor 3 software package (MJ Research).

siRNA Delivery. HeLa cells (15,000 cells/well) stably expressing firefly and *renilla* luciferase proteins were plated in opaque 96-well plates and allowed to adhere overnight. Polymers at 100 mg/ml in DMSO were diluted accordingly into NaAc buffer to concentrations that yield the different polymer:RNA weight ratios. Twenty five microliters of diluted polymer solution was mixed vigorously with 25 µl of RNA (30 µg/ml in NaAc buffer) in a 96-well polystyrene plate. The solutions were left undisturbed for 20 minutes after which time 30 µl of each was added to 200 µl of cell culture media in a deep-well polypropylene plate. The media over the cells was then removed with a 12-channel aspirator wand and followed by the addition of 150 µl/well of polymer-RNA complex solution. Complexes were incubated over the cells for one day (37° C., 5% $CO_2$) after which time they were aspirated off and assayed for luciferase expression using the Dual Glo™ Luciferase Assay following the manufacturer instructions. Luminescence was measured on a Perkin Elmer Victor 3 plate luminometer using a one second per well counting time. The percent knockdown (% KD) was calculated for each polymer in quadruplicate using the following equations:

$$\% \ KD = 1 - (F_f)_p / [n^*(F_f)_u]$$

$$n = (F_R)_p / (F_R)_u$$

where $(F_f)_p$ is the measured firefly fluorescence of a polymer sample, $(F_f)_u$ is the measured firefly fluorescence of the untreated cells, $(F_R)_p$ is the measured *renilla* fluorescence of a polymer sample, and $(F_R)_u$ is the measured *renilla* fluorescence of the untreated cells.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:
1. A polymer of formula:

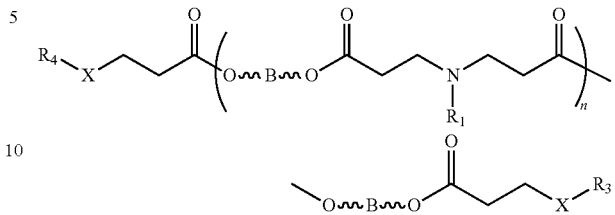

wherein:
B are linkers that may be any substituted or unsubstituted, branched or unbranched, cyclic or acyclic aliphatic or heteroaliphatic moiety; or substituted or unsubstituted aryl or heteroaryl moieties;
$R_1$ hydrogen; halogen; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic or acyclic acyl; substituted or unsubstituted aryl; or substituted or unsubstituted heteroaryl;
X is NH or $NR_X$, wherein $R_X$ is halogen; branched or unbranched, substituted or unsubstituted, cyclic or acyclic aliphatic; branched or unbranched, substituted or unsubstituted, cyclic or acyclic heteroaliphatic; branched or unbranched, substituted or unsubstituted, cyclic or acyclic acyl; substituted or unsubstituted aryl; or substituted or unsubstituted heteroaryl;
$R_3$ and $R_4$ are each independently:

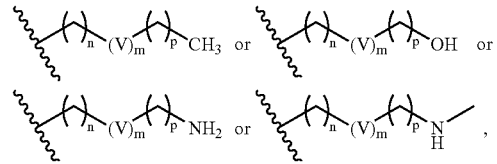

wherein:
n', m, and p are each independently an integer between 0 and 20, inclusive;
each instance of V is independently —O—, —S—, —NH—, —$NR_V$—, or $C(R_V)_2$, wherein each instance of $R_V$ is independently hydrogen, hydroxyl, $C_{1-6}$aliphatic, $C_{1-6}$heteroaliphatic, $C_{1-6}$alkoxy, amino, $C_{1-6}$alkylamino, di($C_{1-6}$alkyl)amino, aryl, heteroaryl, thiol, alkylthioxy, or acyl;
provided that $R^3$ and $R^4$ are different from $R^1$; and
n is an integer between 5 and 10,000, inclusive;
or a pharmaceutically acceptable salt thereof.
2. The polymer of claim 1, wherein B is an substituted or unsubstituted, branched or unbranched, aliphatic or heteroaliphatic moiety.
3. The polymer of claim 1, wherein B is

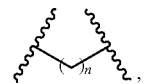

wherein n is an integer between 1 and 20, inclusive.

4. The polymer of claim 1, wherein B is

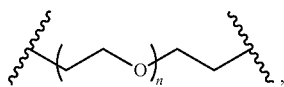

wherein n is an integer between 1 and 20, inclusive.

5. The polymer of claim 1, wherein B is

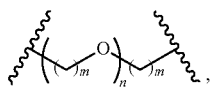

wherein n is an integer between 1 and 20, inclusive; and m is an integer between 1 and 6, inclusive.

6. The polymer of claim 1, wherein B is:

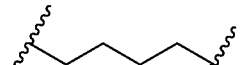

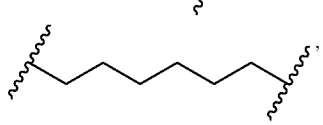

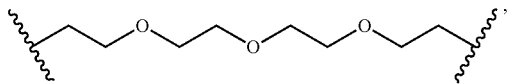

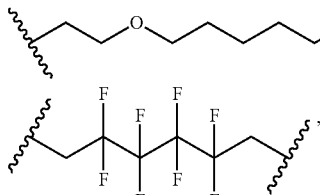

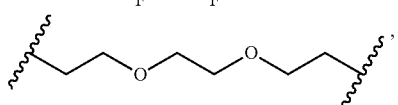

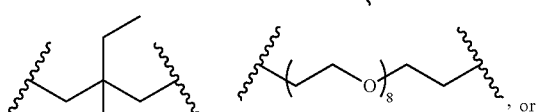

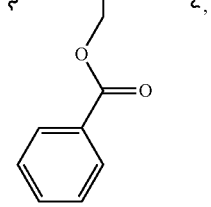

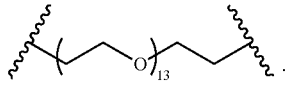

7. The polymer of claim 1, wherein X is NH or NMe.
8. The polymer of claim 1, wherein $R_3$ and $R_4$ are the same.
9. The polymer of claim 1, wherein $R_3$ and $R_4$ are different.
10. The polymer of claim 1, wherein $R_1$ is hydroxyalkyl.
11. The polymer of claim 10, wherein $R_1$ is of the formula:

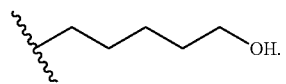

12. The polymer of claim 11, wherein each B is:

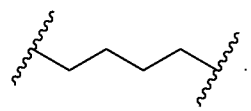

13. The polymer of claim 12, wherein X is NH.
14. The polymer of claim 13, wherein $R^3$ and $R^4$ are the same.
15. The polymer of claim 14, wherein $R_3$ and $R_4$ are selected from the group consisting of:

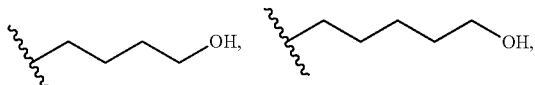

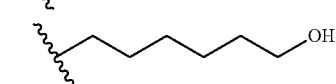

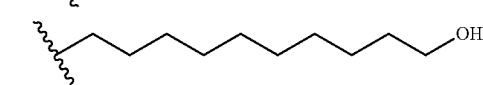

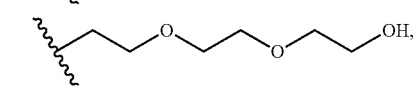

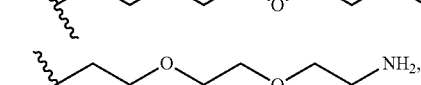

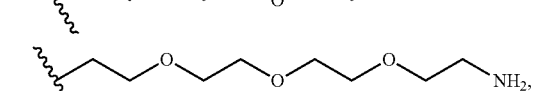

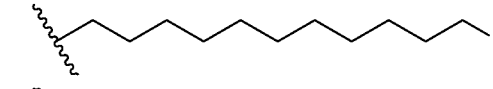

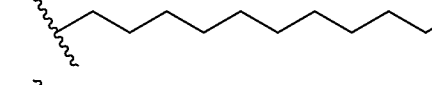

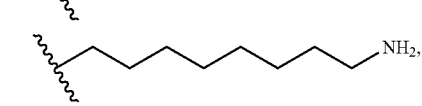

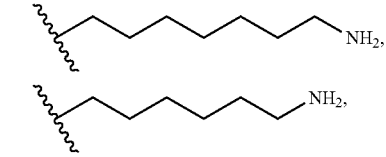

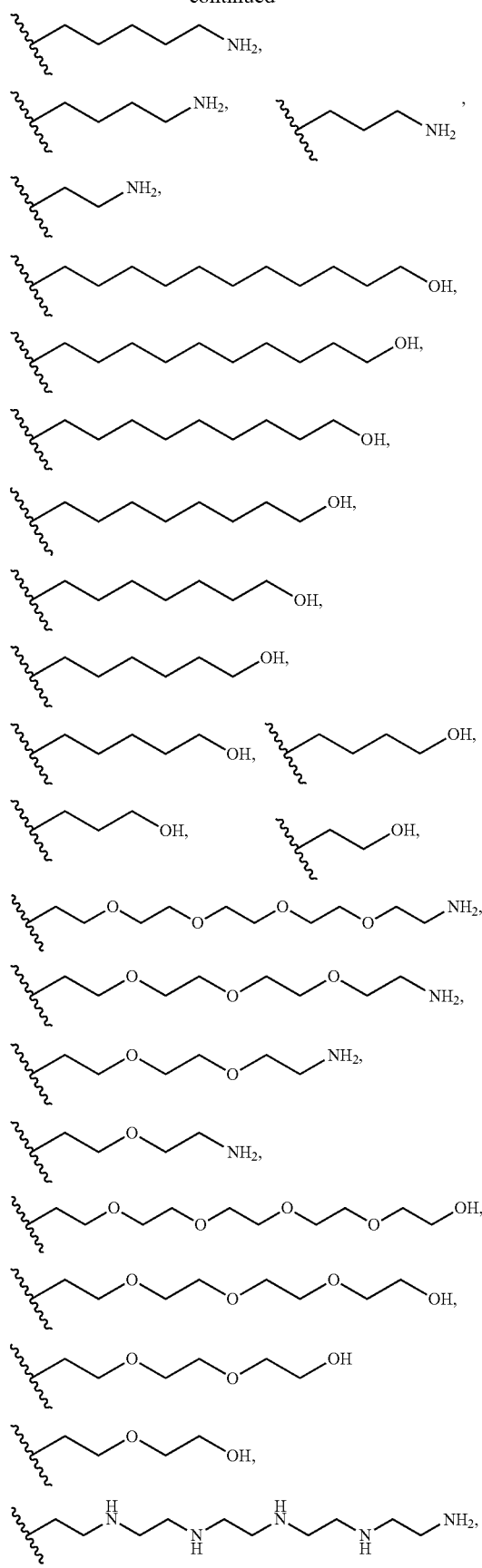
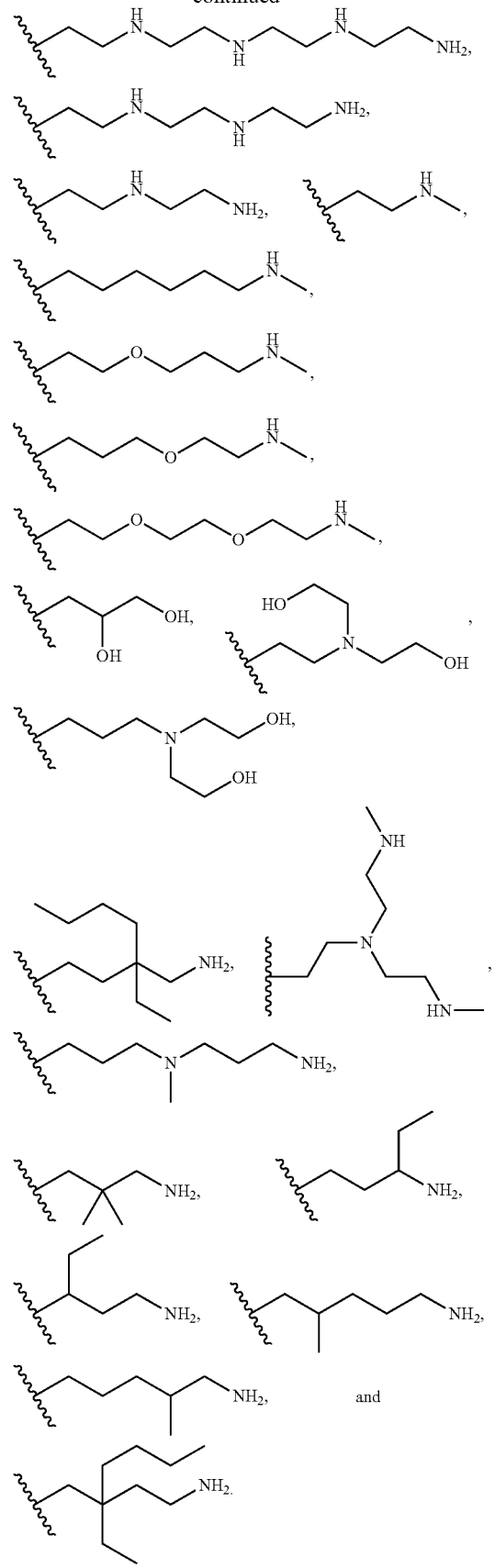

16. The polymer of claim 15, wherein each instance of $R_3$ and $R_4$ is of the formula:
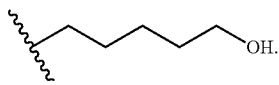
17. The polymer of claim 10, wherein $R_1$ is hydroxyC$_{1-6}$alkyl.
18. The polymer of claim 1, wherein $R_1$ is:
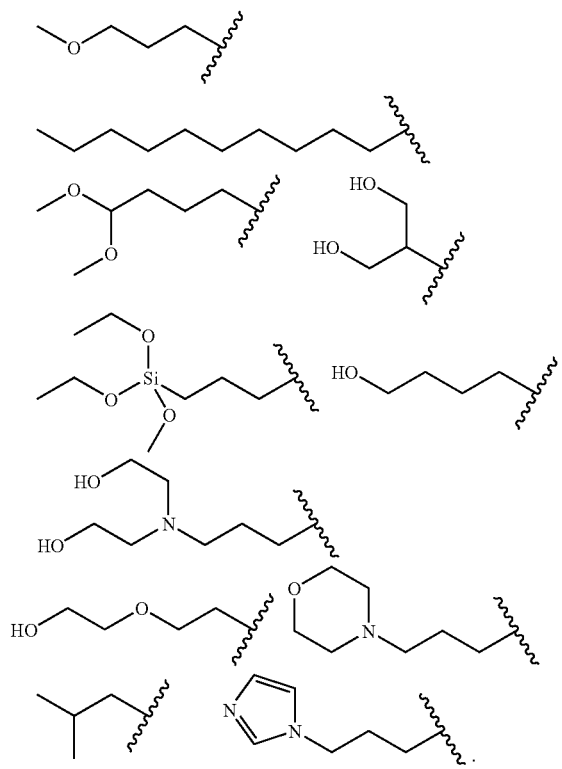
19. The polymer of claim 1, wherein $R_3$ and $R_4$ are
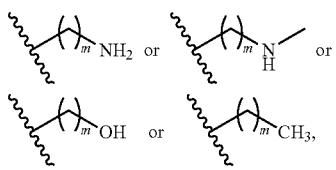
wherein m is an integer between 1 and 20, inclusive.
20. The polymer of claim 1, wherein $R_3$ and $R_4$ are selected from the group consisting of:
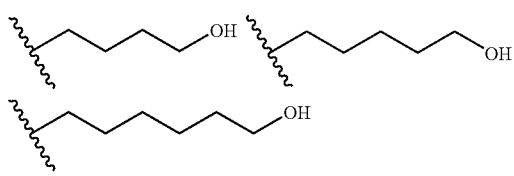
-continued
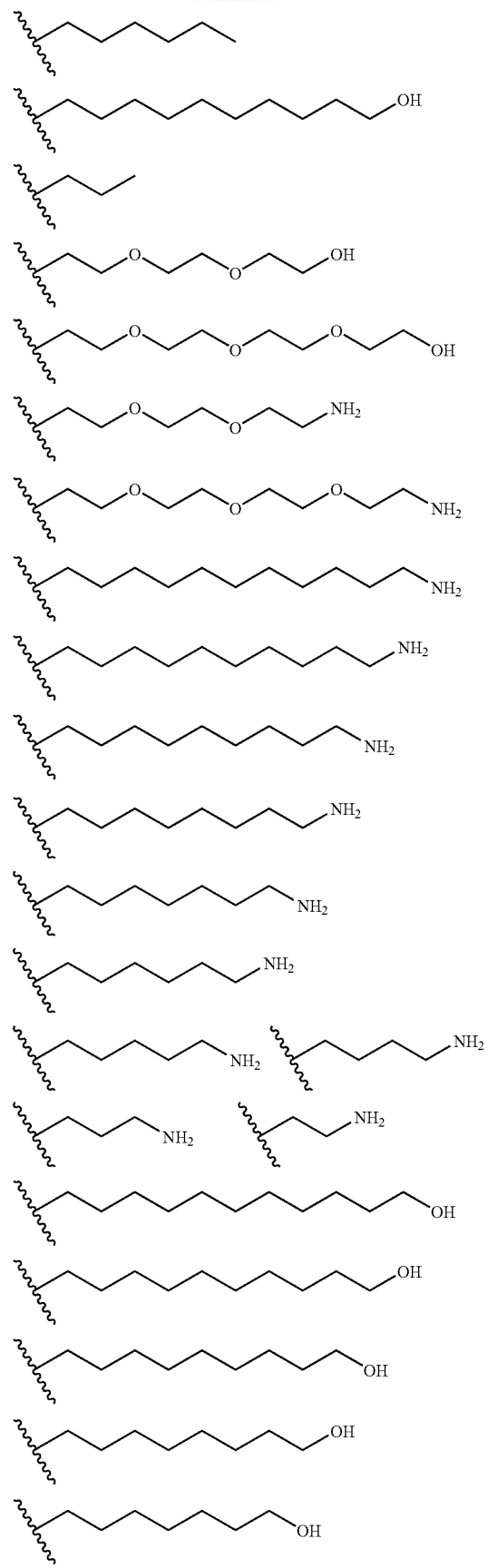

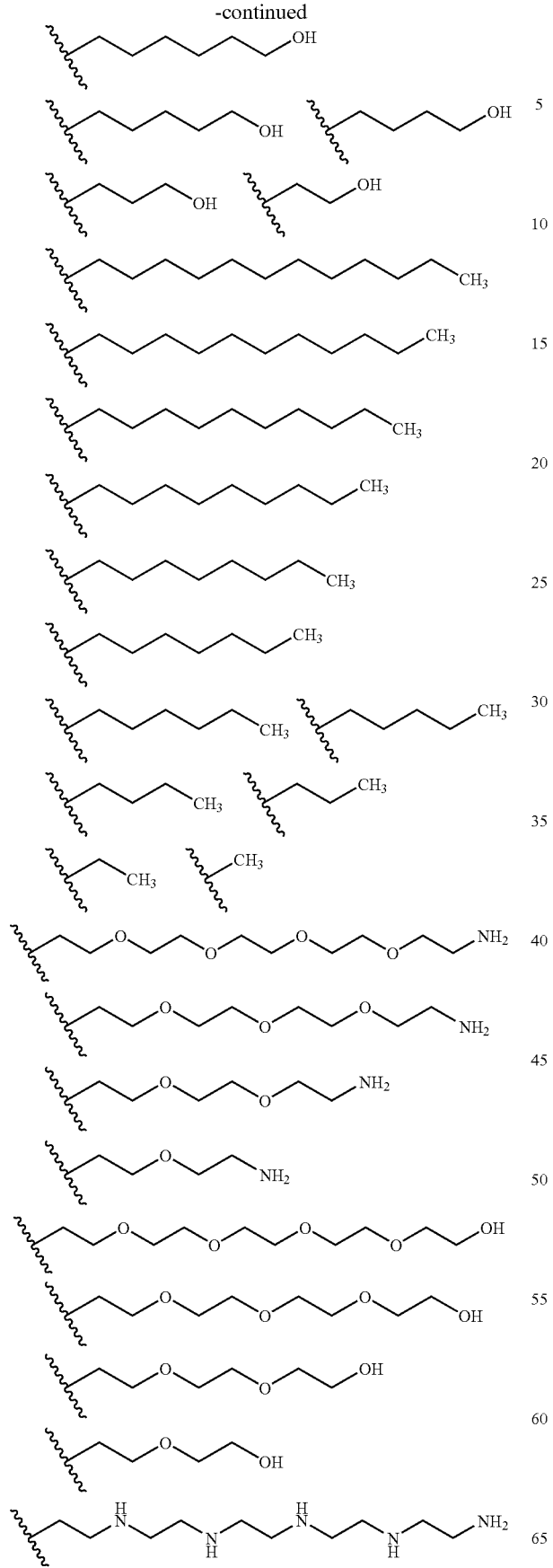
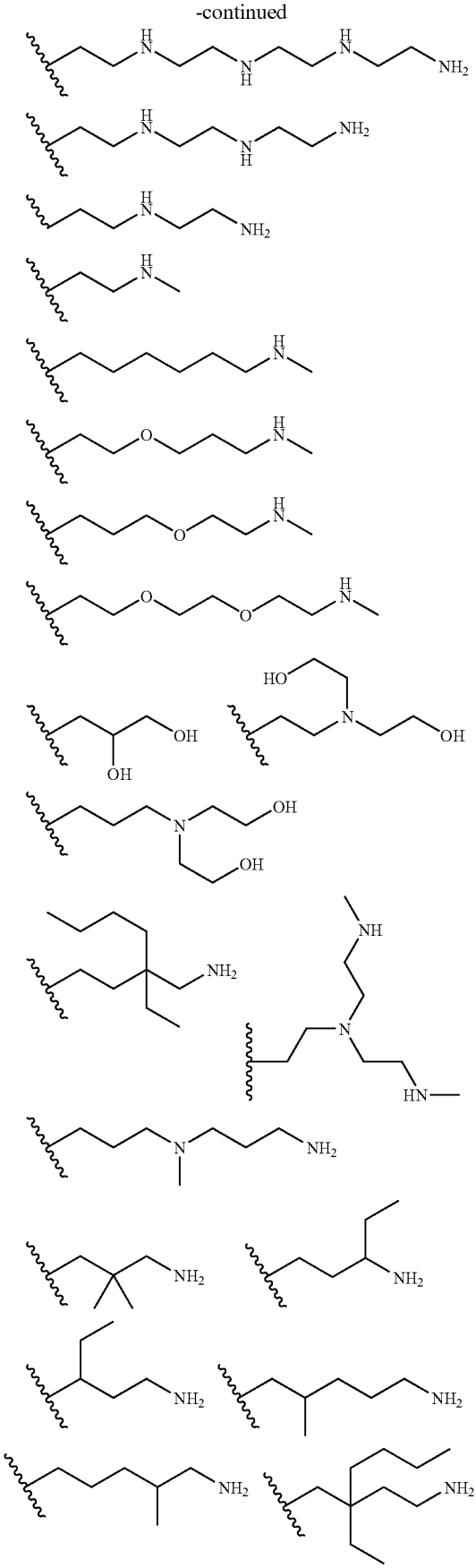

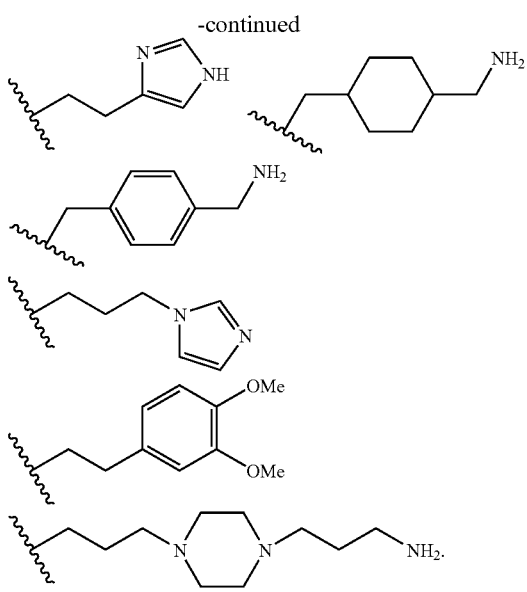

21. The polymer of claim 1, wherein the polymer has a molecular weight between 1,000 and 100,000 g/mol.

22. The polymer of claim 21, wherein the polymer has a molecular weight between 2,000 and 40,000 g/mol.

23. The polymer of claim 21, wherein the polymer has a molecular weight between 5,000 and 50,000 g/mol.

24. A pharmaceutical composition comprising a polynucleotide and a polymer of claim 1.

25. The pharmaceutical composition of claim 24, wherein the polynucleotide is an siRNA.

26. The pharmaceutical composition of claim 24, wherein the polynucleotide is RNA.

27. The pharmaceutical composition of claim 24, wherein the polynucleotide is DNA.

28. The pharmaceutical composition of claim 24, wherein the composition is in the form of nanoparticles comprising the polynucleotide and the polymer.

29. The pharmaceutical composition of claim 24, wherein the composition is in the form of microparticles comprising the polynucleotide and the polymer.

30. The pharmaceutical composition of claim 29, wherein the microparticles have a mean diameter of 1-10 micrometers.

31. The pharmaceutical composition of claim 29, wherein the microparticles have a mean diameter of less than 5 micrometers.

32. The pharmaceutical composition of claim 29, wherein the microparticles have a mean diameter of less than 1 micrometer.

33. A method of synthesizing an end-modified poly(β-amino ester) of claim 1, the method comprising steps of:
   providing an acrylate-terminated poly(beta-amino ester);
   providing an amine; and
   reacting the amine and the acrylate-terminated poly(beta-amino ester) under suitable conditions to form an end-modified poly(β-amino ester).

34. The method of claim 33, wherein the step of providing an acrylate-terminated poly(beta-amino ester) comprises reacting an amine with an excess of a bisacrylate under suitable conditions to form a poly(beta-amino ester).

35. The method of claim 33, wherein the step of reacting comprises reacting the amine and the acrylate-terminated poly(beta-amino ester) in an organic solvent.

36. The method of claim 33, wherein the organic solvent is selected from the group consisting of THF, diethyl ether, glyme, hexanes, methanol, ethanol, isopropanol, methylene chloride, chloroform, carbon tetrachloride, dimethylformamide, acetonitrile, benzene, DMSO, and toluene.

37. The method of claim 33, wherein the organic solvent is DMSO.

38. The method of claim 33, wherein the concentration of the amine is between approximately 0.01 M and 5 M.

39. The method of claim 33, wherein the concentration of the amine is between approximately 0.1 M and 2 M.

40. The method of claim 33, wherein the concentration of the amine is between approximately 1 M and 2 M.

41. The method of claim 33, wherein the concentration of the acrylate-terminated poly(beta-amino ester) is between approximately 0.01 M and 5 M.

42. The method of claim 33, wherein the concentration of the acrylate-terminated poly(beta-amino ester) is between approximately 0.1 M and 2 M.

43. The method of claim 33, wherein the concentration of the acrylate-terminated poly(beta-amino ester) is between approximately 1 M and 2 M.

44. The method of claim 33, wherein the step of reacting comprises reacting the amine and the acrylate-terminated poly(beta-amino ester) at a temperature between 20 and 50° C.

45. The method of claim 33, wherein the step of reacting comprises reacting the amine and the acrylate-terminated poly(beta-amino ester) at a temperature between 30 and 60° C.

46. The polymer of claim 1, wherein $R_3$ and $R_4$ are

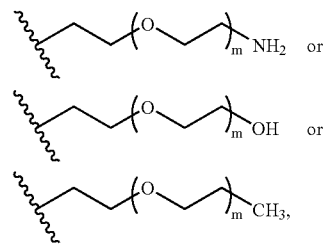

wherein m is an integer between 1 and 20, inclusive.

47. A method of encapsulating an agent in a matrix of end-modified poly(β-amino esters) of claim 1 to form microparticles, the method comprising steps of:
   providing an agent;
   providing an end-modified poly(β-amino ester) of claim 2; and
   contacting the agent and the end-modified poly(β-amino ester) under suitable conditions to form microparticles.

48. The method of claim 47 wherein the agent is a polynucleotide.

49. The method of claim 48 wherein the polynucleotide is DNA.

50. The method of claim 48 wherein the polynucleotide is RNA.

51. The method of claim 47 wherein the agent is a small molecule.

52. The method of claim 47 wherein the agent is a protein.

53. The method of claim 47 wherein the step of contacting comprises spray drying a mixture of the agent and the end-modified poly(β-amino ester).

54. The method of claim 47 wherein the step of contacting comprises double emulsion solvent evaporation techniques.

55. The method of claim 47 wherein the step of contacting comprises a phase inversion technique.

56. A pharmaceutical composition comprising nanoparticles containing a polynucleotide and a polymer of claim 1.

57. A pharmaceutical composition comprising nanoparticles containing a pharmaceutical agent and a polymer of claim 1.

58. A pharmaceutical composition comprising microparticles containing an agent encapsulated in a matrix of a polymer of claim 1.

59. The pharmaceutical composition of claim 58 wherein the microparticles have a mean diameter of 1-10 micrometers.

60. The pharmaceutical composition of claim 58 wherein the microparticles have a mean diameter of less than 5 micrometers.

61. The pharmaceutical composition of claim 58 wherein the microparticles have a mean diameter of less than 1 micrometer.

62. The pharmaceutical composition of claim 58 wherein the agent is a polynucleotide.

63. The pharmaceutical composition of claim 58 wherein the polynucleotide is DNA.

64. The pharmaceutical composition of claim 58 wherein the polynucleotide is RNA.

65. The pharmaceutical composition of claim 58 wherein the polynucleotide is an siRNA.

66. The pharmaceutical composition of claim 58 wherein the agent is a small molecule.

67. The pharmaceutical composition of claim 58 wherein the agent is a peptide.

68. The pharmaceutical composition of claim 58 wherein the agent is a protein.

\* \* \* \* \*

UNITED STATES PATENT AND TRADEMARK OFFICE
CERTIFICATE OF CORRECTION

PATENT NO.        : 8,071,082 B2
APPLICATION NO.   : 11/780754
DATED             : December 6, 2011
INVENTOR(S)       : Gregory T. Zugates et al.

It is certified that error appears in the above-identified patent and that said Letters Patent is hereby corrected as shown below:

In claim 1, at column 68, line 20, please change "$R_1$ hydrogen;" to --$R_1$ is hydrogen;--.

In claim 1, at column 68, line 37, please delete " 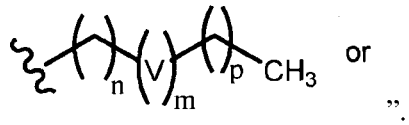 ".

In claim 1, at column 68, line 37, please change " 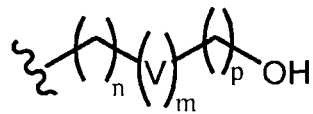 " to

-- 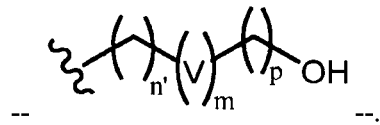 --.

In claim 1, at column 68, line 40, please change "  " to

-- 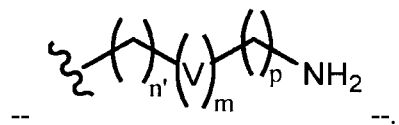 --.

In claim 1, at column 68, line 40, please change " 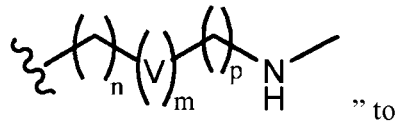 " to

-- 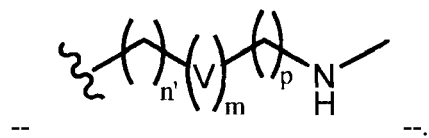 --.

Signed and Sealed this
Nineteenth Day of June, 2012

David J. Kappos
*Director of the United States Patent and Trademark Office*

CERTIFICATE OF CORRECTION (continued)
U.S. Pat. No. 8,071,082 B2

In claim 16, at column 73, line 5, please change " 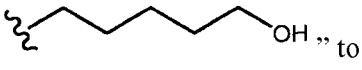 " to -- 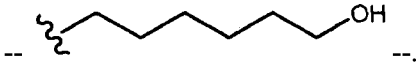 --.

In claim 19, at column 73, line 52, please delete " 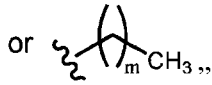 ".

In claim 20, at column 74, line 2, please delete " 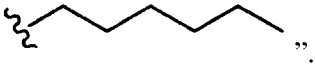 ".

In claim 20, at column 74, line 9, please delete " 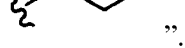 ".

In claim 20, at column 75, line 12, please delete "  ".

In claim 20, at column 75, line 15, please delete " 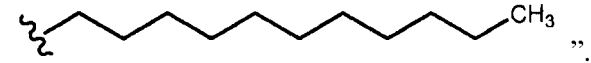 ".

In claim 20, at column 75, line 18, please delete "  ".

In claim 20, at column 75, line 21, please delete "  ".

In claim 20, at column 75, line 25, please delete "  ".

In claim 20, at column 75, line 27, please delete "  ".

In claim 20, at column 75, line 31, please delete "  ".

In claim 20, at column 75, line 31, please delete " 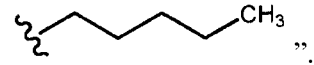 ".

In claim 20, at column 75, line 34, please delete "  ".

In claim 20, at column 75, line 34, please delete "  ".

CERTIFICATE OF CORRECTION (continued)
U.S. Pat. No. 8,071,082 B2

In claim 20, at column 75, line 37, please delete " 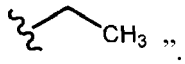 ".

In claim 20, at column 75, line 37, please delete " 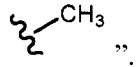 ".

In claim 20, at column 76, line 63, please change " 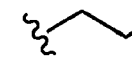 " to

-- 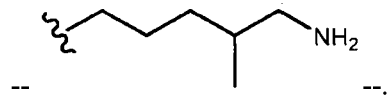 --.

In claim 20, at column 77, line 2, please delete " 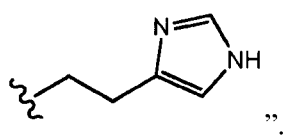 ".

In claim 20, at column 77, line 2, please delete " 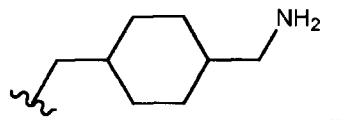 ".

In claim 20, at column 77, line 7, please delete " 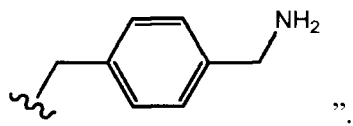 ".

In claim 20, at column 77, line 12, please delete " 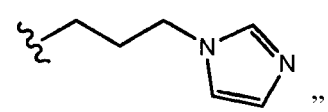 ".

In claim 20, at column 77, line 15, please delete " 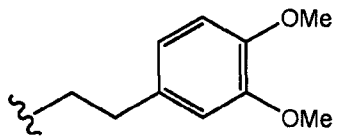 ".

In claim 20, at column 77, line 20, please delete " 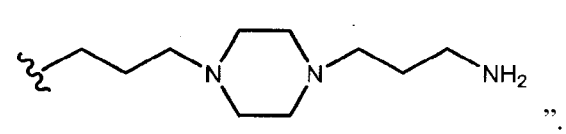 ".

In claim 46, at column 78, lines 38-42, please delete " 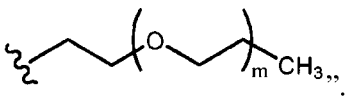.
In claim 47, at column 78, line 50, please change "claim 2" to --claim 1--.